United States Patent
Fremaux et al.

(10) Patent No.: US 12,297,448 B2
(45) Date of Patent: May 13, 2025

(54) METHODS AND STRAIN

(71) Applicant: DUPONT NUTRITION BIOSCIENCES APS, Kongens Lyngby (DK)

(72) Inventors: Christophe Fremaux, Poitiers (FR); Philippe Horvath, Chatellerault (FR); Patrick Boyaval, La Meziere (FR); Pascal Hols, Vedrin (BE); David Blandine, Floreffe (BE); Amandine Radziejwoski, Sterrebeek (BE); Laetitia Fontaine, Louvain-la-Neuve (BE); Frederic Toussaint, Rixensart (BE)

(73) Assignee: International N&H Denmark ApS, Kongens Lyngby (DK)

( * ) Notice: Subject to any disclaimer, the term of this patent is extended or adjusted under 35 U.S.C. 154(b) by 0 days.

(21) Appl. No.: 18/112,968

(22) Filed: Feb. 22, 2023

(65) Prior Publication Data
US 2023/0332183 A1  Oct. 19, 2023

Related U.S. Application Data

(63) Continuation of application No. 16/469,784, filed as application No. PCT/EP2017/083601 on Dec. 19, 2017, now abandoned.

(30) Foreign Application Priority Data

Dec. 19, 2016  (EP) .................... 16205055

(51) Int. Cl.
| | |
|---|---|
| C12N 15/74 | (2006.01) |
| C07K 7/00 | (2006.01) |
| C12N 15/03 | (2006.01) |
| C12N 15/90 | (2006.01) |
| C12Q 1/02 | (2006.01) |

(52) U.S. Cl.
CPC .............. C12N 15/902 (2013.01); C07K 7/00 (2013.01); C12Q 1/02 (2013.01)

(58) Field of Classification Search
CPC ........ C12N 1/20; C12N 15/74; C12N 15/902; C07K 14/195; C07K 7/00; C12Q 1/02
See application file for complete search history.

(56) References Cited

U.S. PATENT DOCUMENTS

| | | | |
|---|---|---|---|
| 8,663,655 B2 | 3/2014 | Boyaval et al. | |
| 9,340,585 B2 | 5/2016 | Gardan et al. | |
| 2011/0269233 A1 | 11/2011 | Malphettes et al. | |

FOREIGN PATENT DOCUMENTS

| | | |
|---|---|---|
| EP | 2248823 A1 | 10/2010 |
| WO | 2007129072 A2 | 11/2007 |
| WO | 2010149721 A1 | 12/2010 |
| WO | 2018114983 A1 | 6/2018 |

OTHER PUBLICATIONS

Bachmann et al., "Time-resolved genetic responses of Lactococcus lactis to a dairy environment", Environmental Microbiology, 2010, vol. 12, No. 5, pp. 1260-1270.
Bolotin et al., "The Complete Genome Sequence of the Lactic Acid Bacterium *Lactococcus lactis* ssp. lactis IL 1403", Cold Spring Harbor Laboratory Press, www.genome.org, 2001, pp. 731-753.
Campbell et al., "A competence regulon in *Streptococcus pneumoniae* revealed by genomic analysis", Molecular Microbiology, 1998, vol. 27, No. 5, pp. 929-939.
David et al., "Natural DNA transformation is functional in *Lactococcus lactis* subsp. *cremoris* 'rWV2", Appl. Environ. Microbial. 83(16), Aug. 2017, pp. 1-17.
Ercan et al., "Genome-Wide Transcriptional Responses to Carbon Starvation in Nongrowing Lactococcus lactis", Applied and Environmental Microbiology, 2015, vol. 81, No. 7, pp. 2554-2561.
Fontaine et al., "Development of a Versatile Procedure Based on Natural Transformation for Marker-Free Targeted Genetic Modification in *Streptococcus thermophilus*", Applied and Environmental Microbiology, 2010, vol. 76, No. 23, pp. 7870-7877.
Hewitt et al., "A new culture medium for the production of antigenic streptococcal haemolysin", J_ Pathol. Bacterial. 35, 1932, pp. 973-975.
Kranenburg et al., "Molecular characterization of the plasmid-encoded eps gene cluster essential for exopolysaccharide biosynthesis in Lactococcus lactis", Molecular Microbiology 1997, vol. 24, No. 2, pp. 387-397.
Lambert et al., "Cre-lox-Based System for Multiple Gene Deletions and Selectable-Marker Removal in Laclobacillus plantarum", Appl. Environ. Microbiol. 73(4), Feb. 2007, pp. 1126-1135.
Lee et al., "Identification of a New Regulator in *Streptococcus pneumoniae* Linking Quorum Sensing to Competence or Genetic Transformation", Journal of Bacteriology, 1999, vol. 181, No. 16, pp. 5004-5016.
Luo et al., "ComX is a unique link between multiple quorum sensing outputs and competence in *Streptococcus pneumoniae*", Molecular Microbiology, 2003, vol. 50, No. 2, pp. 623-633.
Martin-Galiano et al., "High-Efficiency Generation of Antiobiotic-Resistant Strains of *Streptococcus pneumoniae* Py PCR and Transformation", Antimicrobial Agents and Chemotherapy, 2003, vol. 47, No. 4, pp. 1257-1261.
Peterson et al., "Indentification of competence pheromone responsive genes in *Streptococcus pneumoniae* by use of DNA microarrays", Molecular Microbiology, 2004, vol. 51, No. 4, pp. 1051-1070.

(Continued)

*Primary Examiner* — Maryam Monshipouri

(57) ABSTRACT

The present invention relates to a method for transforming a strain of the *Lactococcus* genus through natural competence. The present invention further relates to strains obtained or obtainable by said method. The present invention also relates to a method for identifying a strain of the *Lactococcus* genus which is transformable through natural competence.

12 Claims, 8 Drawing Sheets

Specification includes a Sequence Listing.

(56) References Cited

OTHER PUBLICATIONS

Schmid et al., "Alternative sigma factor activates competence gene expression in Lactobacillus sakei", BMC Microbiology, 2012, vol. 12, No. 32, pp. 1-14.

Sissler et al., "An aminoacyl-IRNA synthetase paralog with a catalytic role in histidine biosynthesis", Proc. Nall. Acad. Sci., 96, Aug. 1999, pp. 8985-8990.

Terzaghi et al., "Improved Medium for Lactic Streptococci and Their Bacteriophages", Applied Microbiology, 1975, vol. 29, No. 6, pp. 807-813.

Updyke et al., "A Dehydrated Medium for the Preparation of Type Specific Extracts of Group A Streptococci", The communicable Disease Center, Public Health Service, 1953, pp. 117-118.

Van Kranenburg et al., "Molecular characterization of the plasmid-encoded eps gene cluster essential for exopolysaccharide biosynthesis in Lactococcus lactis", Mal. Microbial. 24(2), 1997, pp. 387-397.

Ward et al., "Two methods for the genetic differentiation of Lactococcus lactis ssp. lactis and cremoris based on differences in the 16S rRNA gene sequence", FEMS Microbiology Letters, 1998, vol. 166, pp. 15-20.

Wegmann et al., "Complete Genome Sequence of the Prototype Lactic Acid bacterium Lactococcus lactis subsp. cremoris MG1363", Journal of bacteriology, 2007, vol. 189, No. 8, pp. 3256-3270.

Wydau et al., "Conservation of Key Elements of Natural Competence in Lactococcus lactis ssp.", Federation of European Microbiological Societies, 2006, vol. 257, pp. 32-42.

Zaccaria et al., "Control of Competence for DNA Transformation in Streptococcus suis by Genetically Transferable Dherotypes", PLOS One, 2014, vol. 9, Issue 6, e99394.

Aspiras et al., ComX activity of Streptococcus mutans growing in biofilms, FEMS Microbiology Letters 238 (2004), p. 167-174.

Blomqvist et al., Natural Genetic Transformation: a Novel Tool for Efficient Genetic Engineering of the Dairy Bacterium Streptococcus thermophilus. Applied and Environmental Microbiology, Oct. 2006, p. 6751-6756.

Dufour et al., Regulation of the Competence Pathway as a Novel Role Associated with a Streptococcal Bacteriocin. Journal of Bacteriology, vol. 193, No. 23, Dec. 2011, p. 6552-6559.

Gen Bank: AJ890878.1, Mar. 13, 2006.

Guo et al., Growth Phase and pH Influence Peptide Signaling for Competence Development in Streptococcus mutans. Journal of Bacteriology, vol. 196, No. 2, Jan. 2014 , p. 227-236.

Martin et al., Independent evolution of competence regulatory cascades in streptococci? Trends in Microbiology, vol. 14 No. 8, 2006, p. 339-345.

Mulder, J., Activation, regulation and physiology of natural competence in Lactococcus latis, University of Groningen, 2021, 241 pages.

Price et al., From meadows to milk to mucosa—adaptation of Streptococcus and Lactococcus species to their nutritional environments. FEMS Microbial Rev 36 (2012), p. 949-971.

Wahl et al., Control of Natural Transformation in Salivarius Streptococci through Specific Degradation of ax by the MecA-ClpCP Protease Complex. Journal of Bacteriology, Aug. 2014 vol. 196 No. 15, p. 2807-2816.

Melanie Blokesch, Natural competence for transformation, Current Biology, 2016, R1126-R1132, vol. 26, Issue 21.

Lev Rabinovich et al., Prophage Excision Activates Listeria Competence Genes that Promote Phagosomal Escape and Virulence, Cell. Aug. 17, 2012, pp. 792-802, vol. 150(4).

Bolotin, Alexander et al., Genetic and Biochemical Characterization of a High-Affinity Betaine Uptake System (BusA) in Lactococcus lactis Reveals a New Functional Organization within Bacterial ABC Transporters, American Society for Microbiology, 1999, pp. 6238-6246, vol. 181, No. 20.

Claverys, Jean-Pierre, et al., Bacterial 'competence' genes: signatures of active transformation, or only remnants?, Trends in Microbiology, 2003, vol. 11 (4), pp. 161-165.

Dubnau, Dayid, Genetic Competence in Bacillus subtilis, Microbiological Reviews, 1991, pp. 395-424, vol. 55, No. 3.

Finkel, Steven E. et al., DNA as a Nutrient: Novel Role for Bacterial Competence Gene Homologs, Journal of Bacteriology, 2001, pp. 6288-6293, vol. 183, No. 21.

Fontaine, Laetitia et al., A Novel Pheromone Quorum-Sensing System Controls the Development of Natural Competence in Streptococcus thermophilus and Streptococcus salivarius, Journal of Bacteriology, 2010, pp. 1444-1454, vol. 192, No. 5.

Luo, Ping et al., Transient Association of an Alternative Sigma Factor, ComX, with RNA Polymerase during the Period of Competence for Genetic Transformation in Streptococcus pneumoniae, Journal of Bateriology, 2003, pp. 349-358, vol. 185, No. 1.

Mulder, Joyce et al., Unleashing Natural Competence in Lactococcus lactis by Induction of the Competence Regulator ComX, Applied and Environmental Microgiology, 2017, 13 pages, vol. 83, Issue 20.

Todd, E. W. et al., A New Culture Medium For The Production Of Antigenic Streptococcal Haemolysin, Journal of Pathol. Bacteriol, pp. 973-974, vol. 35.

Vanhooff, Virginie et al., Self-control in DNA site-specific recombination mediated by the tyrosine recombinase Tnpl, Molecular Microbiology, 2006, vol. 60 (3), pp. 617-629.

|  |  | Dairy / Model | Dairy | Plant | Dairy / Model | Maize |
|---|---|---|---|---|---|---|
|  |  | MG1363 | SK11 | KW2 | IL1403 | SL12651 SL12653 |
| Reg | comX | + | * | + | + | + |
| Pilus assembly | comGA | + | Tn | + | + | + |
|  | comGB | + | * | + | + | + |
|  | comGC | + | + | + | + | + |
|  | comGD | + | * | + | + | + |
|  | comGE | + | + | + | + | + |
|  | comGF | + | + | + | + | + |
|  | comGG | + | + | + | + | + |
|  | comC | + | * | + | + | + |
| DNA uptake | comFA | + | * | + | + | + |
|  | comFC | + | + | + | + | + |
|  | comEA | + | * | + | + | + |
|  | comEC | * | Tn | + | + | + |
| DNA protection & recombination | ssbB | + | + | + | + | + |
|  | coiA | * | + | + | + | + |
|  | dprA | + | + | + | * | + |
|  | recA | + | + | + | + | + |

```
                         10        20        30        40        50        60
                 ....|....|....|....|....|....|....|....|....|....|....|....|
MG1363           ATGCCTACAATTAACCAATTGGTACGCAAACCTCGTCGTGCTCAAGTGACTAAATCTAAA
MG1363_StrR      ........................................G...................
KW2              ............................................................
KW2_transformant ------------------------------..............................
                                                @

70        80        90       100       110       120
                 ....|....|....|....|....|....|....|....|....|....|....|....|
MG1363           TCACCAGCAATGAACGTTGGCTACAACAGCCGTAAAAAAGTACAAACTAAACTTGCAAGC
MG1363_StrR      ............................................................
KW2              ............................................................
KW2_transformant ............................................................

130       140       150       160       170       180
                 ....|....|....|....|....|....|....|....|....|....|....|....|
MG1363           CCACAAAAACGTGGAGTAGCAACTCGTGTTGGTACAATGACTCCTAAAAAACCTAACTCA
MG1363_StrR      ..................................................T.........
KW2              ..............................................T.............
KW2_transformant ..............................................T...T.........
                                                                #         $ 190       200       210       220       230       240
                 ....|....|....|....|....|....|....|....|....|....|....|....|
MG1363           GCGCTTCGTAAATTCGCGCGTGTACGTCTTTCAAACCTTATGGAAGTAACAGCGTACATC
MG1363_StrR      ............................................................
KW2              ............................................................
KW2_transformant ............................................................

250       260       270       280       290       300
                 ....|....|....|....|....|....|....|....|....|....|....|....|
MG1363           CCAGGTATCGGACACAACCTCCAAGAACACAGTGTTGTACTTCTTCGTGGTGGACGTGTA
MG1363_StrR      ............................................................
KW2              ............................................................
KW2_transformant ............................................................

310       320       330       340       350       360
                 ....|....|....|....|....|....|....|....|....|....|....|....|
MG1363           AAAGACCTTCCAGGGGTACGTTACCATATCGTTCGTGGTGCACTTGATACAGCAGGTGTC
MG1363_StrR      ............................................................
KW2              ............................................................
KW2_transformant ............................................................

370       380       390       400       410
                 ....|....|....|....|....|....|....|....|....|....|....|....
MG1363           GCTGACCGTAAACAAAGCCGTTCTAAATACGGTGCTAAAAAACCAAAAGCTTAA
MG1363_StrR      ......................................................
KW2              ......................................................
KW2_transformant ...................------------------------------------
```

FIG. 4

SEQUENCE LISTING

```
Sequence total quantity: 96
SEQ ID NO: 1            moltype = DNA  length = 492
FEATURE                 Location/Qualifiers
source                  1..492
                        mol_type = unassigned DNA
                        organism = Lactococcus lactis
SEQUENCE: 1
ataacatatt acttggaaga agaggatttt gaaaatcttt tttcagaaat gaaacctata   60
gttatgaaat taatgaaaca aattcgcatt agaacatgaa aaatagagga ttatcttcaa   120
gagggatga ttattttaca tcttctatta gaagagcaga acgatggtca aaagctgcat   180
acaaaattta aggtaaagta tcatcaaaga ttaatagatg aattaagacg aagttatgca   240
aagaaacgaa gccatgacca ttttataggt ttagatgttt atgaatgctc agactggata   300
aattcaggtg atactagtcc agataatgaa gtggtcttca atcatttgct ggcagaagta   360
tatgaaggtt tgagcgcaca ttatcaagac ttactacttc gacaaatgcg aggagaagaa   420
ctaactcgca tgcaacggta tcgccttcgt gaaaaaataa aggccatctt attttcagaa   480
gacgaagagt ga                                                      492

SEQ ID NO: 2            moltype = AA  length = 163
FEATURE                 Location/Qualifiers
source                  1..163
                        mol_type = protein
                        organism = Lactococcus lactis
SEQUENCE: 2
MTYYLEEEDF ENLFSEMKPI VMKLMKQIRI RTWKIEDYLQ EGMIILHLLL EEQNDGQKLH    60
TKFKVKYHQR LIDELRRSYA KKRSHDHFIG LDVYECSDWI NSGDTSPDNE VVFNHLLAEV   120
YEGLSAHYQD LLLRQMRGEE LTRMQRYRLR EKIKAILFSE DEE                     163

SEQ ID NO: 3            moltype = DNA  length = 492
FEATURE                 Location/Qualifiers
source                  1..492
                        mol_type = unassigned DNA
                        organism = Lactococcus lactis
SEQUENCE: 3
atgacatatt acctggaaga aaatgaattc gaaggtttat tttctggaat gaaaccaatc   60
atcagaaaat tgatgaaaca aattcgaatc aaagcatggg acatagagga ttattatcaa   120
gaaggaatga ttattttgca tcaccttta gaagaaaatc acccatccac taatatttat   180
acaaagttca aagtaaaata tcatcaacat ttgattgatg aactacgcca tagctacgcc   240
aaaaaacggc ttcatgacca ttttgtaggt ctggacattt atgaatgttc ggactggata   300
gatgcaggag gaagtacccc tgaaagcgag cttgtgttca atcatctttt agcagaagtt   360
tatgaaggat tgagcgccca ctatcaggaa ttactcgtgc gtcaaatgag aggagaagaa   420
ctcacgcgaa tggaacgcta tcggctaaga gaaaaaatca aaaatatact attttctcga   480
gatgatgatt aa                                                      492

SEQ ID NO: 4            moltype = AA  length = 163
FEATURE                 Location/Qualifiers
source                  1..163
                        mol_type = protein
                        organism = Lactococcus lactis
SEQUENCE: 4
MTYYLEENEF EGLFSGMKPI IRKLMKQIRI KAWDIEDYYQ EGMIILHHLL EENHPSTNIY    60
TKFKVKYHQH LIDELRHSYA KKRLHDHFVG LDIYECSDWI DAGGSTPESE LVFNHLLAEV   120
YEGLSAHYQE LLVRQMRGEE LTRMERYRLR EKIKNILFSR DDD                     163

SEQ ID NO: 5            moltype = DNA  length = 492
FEATURE                 Location/Qualifiers
source                  1..492
                        mol_type = unassigned DNA
                        organism = Lactococcus lactis
SEQUENCE: 5
atgatgaca ttcaagaaaa atacggttta gaattcaacg aattattctc tgagatgcgg    60
ccgataattt ataaattgat gaagcaattg cacatcaaca catgggatta cgatgattac   120
ttccaagagg gaatgattac actacatgaa ttgctgcaga aaattacaaa tttagatcat   180
gtacatacga aatttaaagt ggcttaccat cagcacttaa ttgacgaaat tcgccatatt   240
aaagcacgaa aaagaggttt tgatcagctc catccgatca atgtttatga ctgcgcagat   300
tggattggct caaaccttgc tacacctgaa agcgagatag ttttcaacca tctactagaa   360
```

```
gaagtttatg ataaactttc aacacactat aaagaactgt tggtaaagca aatgcatggg   420
gaacatctta cgagaatgca gaagtatcgt ttaaaggaaa aaattaaagc gatttttattt 480
gatgaagact aa                                                      492
```

```
SEQ ID NO: 6              moltype = AA    length = 163
FEATURE                   Location/Qualifiers
source                    1..163
                          mol_type = protein
                          organism = Lactococcus lactis
SEQUENCE: 6
MDDIQEKYGL EFNELFSEMR PIIYKLMKQL HINTWDYDDY FQEGMITLHE LLQKITNLDH    60
VHTKFKVAYH QHLIDEIRHI KARKRGFDQL HPINVYDCAD WIGSNLATPE SEIVFNHLLE   120
EVYDKLSTHY KELLVKQMHG EHLTRMQKYR LKEKIKAILF DED                    163
```

```
SEQ ID NO: 7              moltype = DNA    length = 405
FEATURE                   Location/Qualifiers
source                    1..405
                          mol_type = unassigned DNA
                          organism = Lactococcus raffinolactis
SEQUENCE: 7
atggataaaa ttgaaaccat acttaaaagt attgaaccga ttattatgaa ctgtcggaaa    60
aaaactaaaa ttccttcctg ggaattagac gactatatgc aggaagggat gattattgct   120
ttagagatgt accatcaact cttattagat ccaccagatg atgactttaa cttctatgtc   180
tatttcaaag tcaggtattc ttgtttctta attgatcact atcgcaaagc tatggcagtc   240
aagagaaaat tcgaccagct tgactattgt gaacttctg agtctgttaa tcttttttgat   300
cacaaacaaa atgtgtctga aaacgtcatg tataacttgt tgtgtcaaga aatacacttg   360
gttttatccc cggaggagct caagcttttt gaggcactta tttga                  405
```

```
SEQ ID NO: 8              moltype = AA    length = 134
FEATURE                   Location/Qualifiers
source                    1..134
                          mol_type = protein
                          organism = Lactococcus raffinolactis
SEQUENCE: 8
MDKIETILKS IEPIIMNCRK KTKIPSWELD DYMQEGMIIA LEMYHQLLLD PPDDDFNFYV    60
YFKVRYSCFL IDHYRKAMAV KRKFDQLDYC ELSESVNLFD HKQNVSENVM YNLLCQEIHL   120
VLSPEELKLF EALI                                                    134
```

```
SEQ ID NO: 9              moltype = DNA    length = 480
FEATURE                   Location/Qualifiers
source                    1..480
                          mol_type = unassigned DNA
                          organism = Lactococcus plantarum
SEQUENCE: 9
atggatagca tagaaatgat gcttcaaaat attgagccaa ttattatgaa ttgtagtaaa    60
acaactagga ttccatcttg ggagctagat gattacatgc aggaggggat gattattgca   120
ctggaaatgt atcaaaatag acataacatc aataacgttt aacgcgtttta tttctatgtc   180
tatttttaaag tcaggtattc ctgttaccctg atagatagtt ttagaaaggc taacgcatat  240
aaaagaaaat ttgatcaacc attatattgt gaaatatctg aagcctttcaa cctttatgat  300
caccaccaaa atgttgcaga caatgtctgt tatcagctat gcaagttga aattcttgag   360
atattaacac cagatgaagc tgattttattt atgaccttga aaaatggtgg aaagtagag   420
agaaatataaa agtatagatt aaagaaaaaa attattgatt atcttaaaga catgttatga  480
```

```
SEQ ID NO: 10             moltype = AA    length = 159
FEATURE                   Location/Qualifiers
source                    1..159
                          mol_type = protein
                          organism = Lactococcus plantarum
SEQUENCE: 10
MDSIEMMLQN IEPIIMNCSK TTRIPSWELD DYMQEGMIIA LEMYQNRHNI NNGNAFNFYV    60
YFKVRYSCYL IDSFRKANAY KRKFDQPLYC EISEAFNLYD HHQNVADNVC YQLLQVEILE   120
ILTPDEADLF MTLKNGGKVE RNKKYRLKKK IIDYLKDML                         159
```

```
SEQ ID NO: 11             moltype = DNA    length = 480
FEATURE                   Location/Qualifiers
source                    1..480
                          mol_type = unassigned DNA
                          organism = Lactococcus piscium
SEQUENCE: 11
atggagactt tagaagccat gctcaaaaac attgaaccta ttattatgaa ttgtcaaaag    60
atggcaaaaa taccttcctg ggatattgac gattatatgc aggaggggag gatcattgca   120
ttagacttgt ataatcagct agcagaaaga atggagacgg atgaggtgaa cttttacgtc   180
tacttcaaag tcagatatac ctgtttcttg attgatactt accgtaagac aaatgccttt   240
aaaagaaaat ttgaccaacc gatttactta gatgtatcca agcatttaa tctgtatgat   300
cataagcaga atgtcgctga taatgtcatg tatactttat tgcatcagga gattctagac   360
atcttaacgc ctgtagaaat tcaaacgcta acgcactaa aaggggaga aaggtcgac    420
cgcaataaaa aattttaggat taaaaagaag attatcaact atattaatca gattttctag  480
```

```
SEQ ID NO: 12             moltype = AA    length = 159
```

| FEATURE | Location/Qualifiers |
|---|---|
| source | 1..159<br>mol_type = protein<br>organism = Lactococcus piscium |

SEQUENCE: 12

```
METLEAMLKN IEPIIMNCQK MAKIPSWDID DYMQEGRIIA LDLYNQLAER METDEVNFYV      60
YFKVRYTCFL IDTYRKTNAF KRKFDQPIYL DVSEAFNLYD HKQNVADNVM YTLLHQEILD     120
ILTPVEIQTL NALKRGEKVD RNKKFRIKKK IINYINQIF                            159
```

| SEQ ID NO: 13 | moltype = DNA length = 486 |
|---|---|
| FEATURE | Location/Qualifiers |
| source | 1..486<br>mol_type = unassigned DNA<br>organism = Lactococcus garvieae |

SEQUENCE: 13

```
atggagcata atttagatat ggagcagctg aagaaatttt tcattctgt ccaacatatt      60
gtgtggaaga acagtcgttt gattccgata aatttttgga cgtttgatga ctatcagcag    120
gaagggcgct tggtattata cgatttgctg ggagatgtga tgacgcaaag gaacttattt    180
tgccatttta aggtacgcta taagcagaga cttattgata ttaaaagaag ggagcgggct    240
tttaaaaggg gttttgattg cgggactggc ttagatatat acgaatattc tgatgctcta    300
aaggggaaag cagccagtcc agaacatatc ctgatttctg aagtttact tgaagaagtt     360
tttgaaaaact taaatttacg ctaccgacgg ctccctcaaaa gttacctcgc cggcgatgaa  420
ttgcaccgta tggaaaagta tcgtttgaag gaaaaaataa cgaatatatt atgaacag     480
cagtga                                                               486
```

| SEQ ID NO: 14 | moltype = AA length = 161 |
|---|---|
| FEATURE | Location/Qualifiers |
| source | 1..161<br>mol_type = protein<br>organism = Lactococcus garvieae |

SEQUENCE: 14

```
MEHNLDMEQL EEIFHSVQHI VWKNSRLIPI NFWTFDDYQQ EGRLVLYDLL GDGVTQRNLF      60
CHFKVRYKQR LIDIKRRERA FKRGFDCGTG LDIYEYSDAL KGKAASPEHI LISGSLLEEV    120
FENLNLRYRR LLKSYLAGDE LHRMEKYRLK EKITNILYEQ Q                        161
```

| SEQ ID NO: 15 | moltype = DNA length = 489 |
|---|---|
| FEATURE | Location/Qualifiers |
| source | 1..489<br>mol_type = unassigned DNA<br>organism = Lactococcus garvieae |

SEQUENCE: 15

```
atggcagaaa ataatttaga taaagaacag cttgaagagt tattccattc acttcaacat     60
attgtttgga agaacagtca tttaattaaa ataaattttt ggacaatgga tgattatcag    120
caagaagggc gactggtttt ataccagtta cttgaagatg gcgtgacaca ggaaaaacta    180
ttttgccatt ttaaagtgcg atataagcaa cggttgattg atataaaaag acgagaaaga    240
gcatttaagc ggggttttga ttgtgggggct ggtttagata tatgagta ttctgatgcc     300
ctgaaaggca aagctaccag tcctgaatat aacttaattt cagttactt acttgaagag    360
gttcatcaaa gtttgagttt gagataccgc aatttattgg agaatcatct gtcaggagtg   420
gagttgcatc gaatggaaaa ataccgtttaa aaggaaaaaa tcaagaaat actctatgaa    480
gaagaatga                                                            489
```

| SEQ ID NO: 16 | moltype = AA length = 162 |
|---|---|
| FEATURE | Location/Qualifiers |
| source | 1..162<br>mol_type = protein<br>organism = Lactococcus garvieae |

SEQUENCE: 16

```
MAENNLDKEQ LEELFHSLQH IVWKNSHLIK INFWTMDDYQ QEGRLVLYQL LEDGVTQEKL      60
FCHFKVRYKQ RLIDIKRRER AFKRGFDCGA GLDIYEYSDA LKGKATSPEY NLISVTLLEE    120
VHQSLSLRYR NLLENHLSGV ELHRMEKYRL KEKIKRILYE EE                       162
```

| SEQ ID NO: 17 | moltype = DNA length = 486 |
|---|---|
| FEATURE | Location/Qualifiers |
| source | 1..486<br>mol_type = unassigned DNA<br>organism = Lactococcus garvieae |

SEQUENCE: 17

```
atggagcata atttagatat ggagcagctg aagagatat tcattctgt tcaacatatt       60
gtatggaaga atagtcgttt gattccgata aatttttgga cgatagtga ctatcagcag    120
gaagggcgtt tggtattata tgatttactt gaggatggtg tgacacaaag aaaacttttt    180
tgccatttta agtacgttta aagcagaga cttattgata ttaaaagaag ggagcgggct     240
tttaaaaggg gttttgactg tgggactggg ctagatattt acgaatattc agatgcttta    300
aaaggaaaag tagccagtcc agaacatact ctgatttctg cagtttgct tgaagaagtt    360
ttagaaaaact taaatttacg ctaccgtgct cttcttaaaa gttaccttgc tggtgatgaa  420
ctgcatcgaa tggaaaaaca tcgtttgaaa gaaaaaataa taaaatatt atgatgaa     480
cagtga                                                               486
```

| SEQ ID NO: 18 | moltype = AA length = 161 |
|---|---|
| FEATURE | Location/Qualifiers |

| | | |
|---|---|---|
| source | 1..161 | |
| | mol_type = protein | |
| | organism = Lactococcus garvieae | |
| SEQUENCE: 18 | | |

MEHNLDMEQL EEIFHSVQHI VWKNSRLIPI NFWTIDDYQQ EGRLVLYDLL EDGVTQRKLF 60
CHFKVRYKQR LIDIKRRERA FKRGFDCGTG LDIYEYSDAL KGKVASPEHT LISGSLLEEV 120
LENLNLRYRA LLKSYLAGDE LHRMEKHRLK EKIIKILYDE Q 161

| | | |
|---|---|---|
| SEQ ID NO: 19 | moltype = DNA length = 438 | |
| FEATURE | Location/Qualifiers | |
| source | 1..438 | |
| | mol_type = unassigned DNA | |
| | organism = Lactococcus fujiensis | |
| SEQUENCE: 19 | | | ttgaaaccga tcgtttcaaa atctatgaga acattaaaaa tcaattttg gactacagag 60
gattatcatc aagagggtct aattacatta aatgaaatat taaattcagg atgtaaggag 120
tcacaactat acattcactt taaagtcaaa tatcgacaaa agctaataga cgtgattaga 180
aaatcacagg cgcaaaaaag aatctgggat aatgcagaga gtattgatgt ttacgaatct 240
gaaaatcaaa ttaattccag taactcaaac cccgaagaca taatagtcta tgacagtctt 300
gtaaaggaag taataacaaa attaacacct tcataccgga aactactgaa acgacatcta 360
agaggtgagg atgtgacaag gatggaaaaa tacagactga aggaacgaat caaacaaatt 420
ttatttgatg gtgattga 438

| | | |
|---|---|---|
| SEQ ID NO: 20 | moltype = AA length = 145 | |
| FEATURE | Location/Qualifiers | |
| source | 1..145 | |
| | mol_type = protein | |
| | organism = Lactococcus fujiensis | |
| SEQUENCE: 20 | | |

MKPIVSKSMR TLKINFWTTE DYHQEGLITL NEILNSGCKE SQLYIHFKVK YRQKLIDVIR 60
KSQAQKRIWD NAESIDVYES ENQINSSNSN PEDIIVYDSL VKEVITKLTP SYRKLLKRHL 120
RGEDVTRMEK YRLKERIKQI LFDGD 145

| | | |
|---|---|---|
| SEQ ID NO: 21 | moltype = DNA length = 480 | |
| FEATURE | Location/Qualifiers | |
| source | 1..480 | |
| | mol_type = unassigned DNA | |
| | organism = Lactococcus chungangensis | |
| SEQUENCE: 21 | | | atggataaga ttgaaaccat acttaaaaat attgaaccga ttatcatgaa ctgtcgaaaa 60
aaaactaaca tcccttcctg gcaattagac gactatctcc aggaaggcat gattattgct 120
ctagagatgt atcatcaact tttattagac ccaccagatg atgactttaa cttctatgtt 180
tatttcaaag tgagatattc ttgtttcttg attgatcagt atcggagaaa catggctatc 240
aaaagaaaat tcgaccagat tgactattgt gaactatctg aggcgtttta tcttttgat 300
caaaatcaag atgtctctga aaacgtcatg tataatttgt tatgtcaaga aatacacttg 360
cttctatctc tgaagaacgg agagcttttt gaggcactta aaaatggaca aagattgac 420
cgtaatcaaa agtttcgtat caagaagaaa attattgaat atattaagag gttttggtga 480

| | | |
|---|---|---|
| SEQ ID NO: 22 | moltype = AA length = 159 | |
| FEATURE | Location/Qualifiers | |
| source | 1..159 | |
| | mol_type = protein | |
| | organism = Lactococcus chungangensis | |
| SEQUENCE: 22 | | |

MDKIETILKN IEPIIMNCRK KTNIPSWQLD DYLQEGMIIA LEMYHQLLLD PPDDDFNFYV 60
YFKVRYSCFL IDQYRRNMAV KRKFDQIDYC ELSEAFYLFD QNQDVSENVM YNLLCQEIHL 120
LLSPEERELF EALKNGQKID RNQKFRIKKK IIEYIKRFW 159

| | | |
|---|---|---|
| SEQ ID NO: 23 | moltype = DNA length = 414 | |
| FEATURE | Location/Qualifiers | |
| source | 1..414 | |
| | mol_type = unassigned DNA | |
| | organism = Lactococcus lactis | |
| SEQUENCE: 23 | | | atgcctacaa ttaaccaatt ggtacgcaaa cctcgtcgtg ctcaagtgac taaatctaaa 60
tcaccagcaa tgaacgttgg ctacaacagc cgtaaaaaag tacaaactaa acttgcaagc 120
ccacaaaaac gtggagtagc aactcgtgtt ggtacaatga ctcctaaaaa acctaactca 180
gcgcttcgta aattcgcgcg tgtacgtctt caaaccttaa tggaagtaac agcgtacatc 240
ccaggtatcg gacacaacct ccaagaacac agtgttgtac ttcttcgtgg tggacgtatc 300
aaagaccttc caggggtacg ttaccatatc gttcgtggtg cacttgatac agcaggtgtc 360
gctgaccgta acaaaagccg ttctaaatac ggtgctaaaa aaccaaaagc ttaa 414

| | | |
|---|---|---|
| SEQ ID NO: 24 | moltype = DNA length = 414 | |
| FEATURE | Location/Qualifiers | |
| source | 1..414 | |
| | mol_type = unassigned DNA | |
| | organism = Lactococcus lactis | |
| SEQUENCE: 24 | | | atgcctacaa ttaaccaatt ggtacgcaaa cctcgtcggg ctcaagtgac taaatctaaa 60

```
tcaccagcaa tgaacgttgg ctacaacagc cgtaaaaaag tacaaactaa acttgcaagc    120
ccacaaaaac gtggagtagc aactcgtgtt ggtacaatga ctcctataaa acctaactca    180
gcgcttcgta aattcgcgcg tgtacgtctt tcaaaccttg tggaagtaac agcgtacatc    240
ccaggtatcg gacacaacct ccaagaacac agtgttgtac ttcttcgtgg tggacgtgta    300
aaagaccttc caggggtacg ttaccatatc gttcgtggtg cacttgatac agcaggtgtc    360
gctgaccgta aacaaagccg ttctaaatac ggtgctaaaa aaccaaaagc ttaa          414

SEQ ID NO: 25              moltype = DNA  length = 414
FEATURE                    Location/Qualifiers
source                     1..414
                           mol_type = unassigned DNA
                           organism = Lactococcus lactis
SEQUENCE: 25
atgcctacaa ttaaccaatt ggtacgcaaa cctcgtcgtg ctcaagtgac taaatctaaa     60
tcaccagcaa tgaacgttgg ctacaacagc cgtaaaaaag tacaaactaa acttgcaagc    120
ccacaaaaac gtggagtagc aactcgtgtt ggtactatga ctcctaaaaa acctaactca    180
gcgcttcgta aattcgcgcg tgtacgtctt tcaaaccttg tggaagtaac agcgtacatc    240
ccaggtatcg gacacaacct ccaagaacac agtgttgtac ttcttcgtgg tggacgtgta    300
aaagaccttc caggggtacg ttaccatatc gttcgtggtg cacttgatac agcaggtgtc    360
gctgaccgta aacaaagccg ttctaaatac ggtgctaaaa aaccaaaagc ttaa          414

SEQ ID NO: 26              moltype = DNA  length = 26
FEATURE                    Location/Qualifiers
misc_feature               1..26
                           note = Oligonucleotide primer
source                     1..26
                           mol_type = other DNA
                           organism = synthetic construct
SEQUENCE: 26
aaaagagctc aattatgaaa aagagg                                          26

SEQ ID NO: 27              moltype = DNA  length = 25
FEATURE                    Location/Qualifiers
misc_feature               1..25
                           note = Oligonucleotide primer
source                     1..25
                           mol_type = other DNA
                           organism = synthetic construct
SEQUENCE: 27
aaaactgcag ttaatcatca tctcg                                           25

SEQ ID NO: 28              moltype = DNA  length = 28
FEATURE                    Location/Qualifiers
misc_feature               1..28
                           note = Oligonucleotide primer
source                     1..28
                           mol_type = other DNA
                           organism = synthetic construct
SEQUENCE: 28
aaaagagctc ataaaaggag aactttcc                                        28

SEQ ID NO: 29              moltype = DNA  length = 25
FEATURE                    Location/Qualifiers
misc_feature               1..25
                           note = Oligonucleotide primer
source                     1..25
                           mol_type = other DNA
                           organism = synthetic construct
SEQUENCE: 29
aaaactgcag tcactcttcg tcttc                                           25

SEQ ID NO: 30              moltype = DNA  length = 29
FEATURE                    Location/Qualifiers
misc_feature               1..29
                           note = Oligonucleotide primer
source                     1..29
                           mol_type = other DNA
                           organism = synthetic construct
SEQUENCE: 30
atatcaattg gtcctcggga tatgataag                                       29

SEQ ID NO: 31              moltype = DNA  length = 19
FEATURE                    Location/Qualifiers
misc_feature               1..19
                           note = Oligonucleotide primer
source                     1..19
                           mol_type = other DNA
                           organism = synthetic construct
SEQUENCE: 31
```

```
gactttgaac ctcaactcc                                                 19

SEQ ID NO: 32          moltype = DNA  length = 32
FEATURE                Location/Qualifiers
misc_feature           1..32
                       note = Oligonucleotide primer
source                 1..32
                       mol_type = other DNA
                       organism = synthetic construct
SEQUENCE: 32
atagtctcga gtttaagcaa ttgaatcgct ag                                  32

SEQ ID NO: 33          moltype = DNA  length = 42
FEATURE                Location/Qualifiers
misc_feature           1..42
                       note = Oligonucleotide primer
source                 1..42
                       mol_type = other DNA
                       organism = synthetic construct
SEQUENCE: 33
gcaaaaagtt tccaaatttc atactagaat atacgcaatt tg                       42

SEQ ID NO: 34          moltype = DNA  length = 42
FEATURE                Location/Qualifiers
misc_feature           1..42
                       note = Oligonucleotide primer
source                 1..42
                       mol_type = other DNA
                       organism = synthetic construct
SEQUENCE: 34
caaattgcgt atattctagt atgaaatttg gaactttttt gc                       42

SEQ ID NO: 35          moltype = DNA  length = 34
FEATURE                Location/Qualifiers
misc_feature           1..34
                       note = Oligonucleotide primer
source                 1..34
                       mol_type = other DNA
                       organism = synthetic construct
SEQUENCE: 35
gcgaaaggat ccctattagg tatattccat gtgg                                34

SEQ ID NO: 36          moltype = DNA  length = 37
FEATURE                Location/Qualifiers
misc_feature           1..37
                       note = Oligonucleotide primer
source                 1..37
                       mol_type = other DNA
                       organism = synthetic construct
SEQUENCE: 36
gctccctcga gggcggctct gttggattaa tatatgg                             37

SEQ ID NO: 37          moltype = DNA  length = 44
FEATURE                Location/Qualifiers
misc_feature           1..44
                       note = Oligonucleotide primer
source                 1..44
                       mol_type = other DNA
                       organism = synthetic construct
SEQUENCE: 37
ctttatgttt ttggcggatc tcatactaga atatacgcaa tttg                     44

SEQ ID NO: 38          moltype = DNA  length = 44
FEATURE                Location/Qualifiers
misc_feature           1..44
                       note = Oligonucleotide primer
source                 1..44
                       mol_type = other DNA
                       organism = synthetic construct
SEQUENCE: 38
caaattgcgt atattctagt atgagatccg ccaaaaacat aaag                     44

SEQ ID NO: 39          moltype = DNA  length = 31
FEATURE                Location/Qualifiers
misc_feature           1..31
                       note = Oligonucleotide primer
source                 1..31
                       mol_type = other DNA
                       organism = synthetic construct
```

```
SEQUENCE: 39
gcgaaaggat ccttacaatt tgggctttcc g                              31

SEQ ID NO: 40           moltype = DNA  length = 31
FEATURE                 Location/Qualifiers
misc_feature            1..31
                        note = Oligonucleotide primer
source                  1..31
                        mol_type = other DNA
                        organism = synthetic construct
SEQUENCE: 40
aaaacccggg tttaagcaat tgaatcgcta g                              31

SEQ ID NO: 41           moltype = DNA  length = 30
FEATURE                 Location/Qualifiers
misc_feature            1..30
                        note = Oligonucleotide primer
source                  1..30
                        mol_type = other DNA
                        organism = synthetic construct
SEQUENCE: 41
aaaacccggg aaataaatgg ctacaaaatt                                30

SEQ ID NO: 42           moltype = DNA  length = 29
FEATURE                 Location/Qualifiers
misc_feature            1..29
                        note = Oligonucleotide primer
source                  1..29
                        mol_type = other DNA
                        organism = synthetic construct
SEQUENCE: 42
aaaacggccg ttacaatttg ggctttccg                                 29

SEQ ID NO: 43           moltype = DNA  length = 31
FEATURE                 Location/Qualifiers
misc_feature            1..31
                        note = Oligonucleotide primer
source                  1..31
                        mol_type = other DNA
                        organism = synthetic construct
SEQUENCE: 43
atagtctcga gaaataaatg gctacaaaat t                              31

SEQ ID NO: 44           moltype = DNA  length = 46
FEATURE                 Location/Qualifiers
misc_feature            1..46
                        note = Oligonucleotide primer
source                  1..46
                        mol_type = other DNA
                        organism = synthetic construct
SEQUENCE: 44
ctttatgttt ttggcggatc tcatactaga ctatacgcaa ataatc              46

SEQ ID NO: 45           moltype = DNA  length = 46
FEATURE                 Location/Qualifiers
misc_feature            1..46
                        note = Oligonucleotide primer
source                  1..46
                        mol_type = other DNA
                        organism = synthetic construct
SEQUENCE: 45
gattatttgc gtatagtcta gtatgagatc cgccaaaaac ataaag              46

SEQ ID NO: 46           moltype = DNA  length = 42
FEATURE                 Location/Qualifiers
misc_feature            1..42
                        note = Oligonucleotide primer
source                  1..42
                        mol_type = other DNA
                        organism = synthetic construct
SEQUENCE: 46
agcttcctaa tacaacacaa ttaatattgt gttgtattat tg                  42

SEQ ID NO: 47           moltype = DNA  length = 42
FEATURE                 Location/Qualifiers
misc_feature            1..42
                        note = Oligonucleotide primer
source                  1..42
                        mol_type = other DNA
```

```
                              organism = synthetic construct
SEQUENCE: 47
aattcaataa tacaacacaa tattaattgt gttgtattag ga                    42

SEQ ID NO: 48         moltype = DNA  length = 19
FEATURE               Location/Qualifiers
misc_feature          1..19
                      note = Oligonucleotide primer
source                1..19
                      mol_type = other DNA
                      organism = synthetic construct
SEQUENCE: 48
atgcctacaa ttaaccaat                                              19

SEQ ID NO: 49         moltype = DNA  length = 17
FEATURE               Location/Qualifiers
misc_feature          1..17
                      note = Oligonucleotide primer
source                1..17
                      mol_type = other DNA
                      organism = synthetic construct
SEQUENCE: 49
caccgtattt agaacgg                                                17

SEQ ID NO: 50         moltype = DNA  length = 19
FEATURE               Location/Qualifiers
misc_feature          1..19
                      note = Oligonucleotide primer
source                1..19
                      mol_type = other DNA
                      organism = synthetic construct
SEQUENCE: 50
atgcctacta ttaaccaat                                              19

SEQ ID NO: 51         moltype = DNA  length = 17
FEATURE               Location/Qualifiers
misc_feature          1..17
                      note = Oligonucleotide primer
source                1..17
                      mol_type = other DNA
                      organism = synthetic construct
SEQUENCE: 51
taccgtattt agaacgg                                                17

SEQ ID NO: 52         moltype = DNA  length = 21
FEATURE               Location/Qualifiers
misc_feature          1..21
                      note = Oligonucleotide primer
source                1..21
                      mol_type = other DNA
                      organism = synthetic construct
SEQUENCE: 52
agtagtatca gcactgacag c                                           21

SEQ ID NO: 53         moltype = DNA  length = 19
FEATURE               Location/Qualifiers
misc_feature          1..19
                      note = Oligonucleotide primer
source                1..19
                      mol_type = other DNA
                      organism = synthetic construct
SEQUENCE: 53
acacctttgt tcttgaagg                                              19

SEQ ID NO: 54         moltype = DNA  length = 30
FEATURE               Location/Qualifiers
misc_feature          1..30
                      note = Oligonucleotide primer
source                1..30
                      mol_type = other DNA
                      organism = synthetic construct
SEQUENCE: 54
aaagagctca aataaaaat gaaattatgg                                   30

SEQ ID NO: 55         moltype = DNA  length = 29
FEATURE               Location/Qualifiers
misc_feature          1..29
                      note = Oligonucleotide primer
source                1..29
```

```
                              mol_type = other DNA
                              organism = synthetic construct
SEQUENCE: 55
aaagctagcg ggaaaaaatt gtgaattac                                          29

SEQ ID NO: 56         moltype = DNA   length = 32
FEATURE               Location/Qualifiers
misc_feature          1..32
                      note = Oligonucleotide primer
source                1..32
                      mol_type = other DNA
                      organism = synthetic construct
SEQUENCE: 56
aaaaactagt gcagtttaaa ttcggtcctc gg                                      32

SEQ ID NO: 57         moltype = DNA   length = 31
FEATURE               Location/Qualifiers
misc_feature          1..31
                      note = Oligonucleotide primer
source                1..31
                      mol_type = other DNA
                      organism = synthetic construct
SEQUENCE: 57
aaaaactagt gtacagtcgg cattatctca t                                       31

SEQ ID NO: 58         moltype = DNA   length = 20
FEATURE               Location/Qualifiers
misc_feature          1..20
                      note = Oligonucleotide primer
source                1..20
                      mol_type = other DNA
                      organism = synthetic construct
SEQUENCE: 58
ctttaatgat ggaatgattg                                                    20

SEQ ID NO: 59         moltype = DNA   length = 47
FEATURE               Location/Qualifiers
misc_feature          1..47
                      note = Oligonucleotide primer
source                1..47
                      mol_type = other DNA
                      organism = synthetic construct
SEQUENCE: 59
ctattaatct tatcatatcc cgaggatcca tataactata tgaaacc                      47

SEQ ID NO: 60         moltype = DNA   length = 26
FEATURE               Location/Qualifiers
misc_feature          1..26
                      note = Oligonucleotide primer
source                1..26
                      mol_type = other DNA
                      organism = synthetic construct
SEQUENCE: 60
tcctcgggat atgataagat taatag                                             26

SEQ ID NO: 61         moltype = DNA   length = 27
FEATURE               Location/Qualifiers
misc_feature          1..27
                      note = Oligonucleotide primer
source                1..27
                      mol_type = other DNA
                      organism = synthetic construct
SEQUENCE: 61
tctcatatta taaagccag tcattag                                             27

SEQ ID NO: 62         moltype = DNA   length = 51
FEATURE               Location/Qualifiers
misc_feature          1..51
                      note = Oligonucleotide primer
source                1..51
                      mol_type = other DNA
                      organism = synthetic construct
SEQUENCE: 62
ctaatgactg gcttttataa tatgagactt agaaaaatct aaatatggtt g                 51

SEQ ID NO: 63         moltype = DNA   length = 24
FEATURE               Location/Qualifiers
misc_feature          1..24
                      note = Oligonucleotide primer
```

```
source                  1..24
                        mol_type = other DNA
                        organism = synthetic construct
SEQUENCE: 63
gaagattttt aatttcaagt gtag                                              24

SEQ ID NO: 64           moltype = DNA   length = 20
FEATURE                 Location/Qualifiers
misc_feature            1..20
                        note = Oligonucleotide primer
source                  1..20
                        mol_type = other DNA
                        organism = synthetic construct
SEQUENCE: 64
tcagtaccga aaaacgaatg                                                   20

SEQ ID NO: 65           moltype = DNA   length = 19
FEATURE                 Location/Qualifiers
misc_feature            1..19
                        note = Oligonucleotide primer
source                  1..19
                        mol_type = other DNA
                        organism = synthetic construct
SEQUENCE: 65
atttaccagt tccgttagg                                                    19

SEQ ID NO: 66           moltype = DNA   length = 20
FEATURE                 Location/Qualifiers
misc_feature            1..20
                        note = Oligonucleotide primer
source                  1..20
                        mol_type = other DNA
                        organism = synthetic construct
SEQUENCE: 66
taacaatgat acagaagatg                                                   20

SEQ ID NO: 67           moltype = DNA   length = 46
FEATURE                 Location/Qualifiers
misc_feature            1..46
                        note = Oligonucleotide primer
source                  1..46
                        mol_type = other DNA
                        organism = synthetic construct
SEQUENCE: 67
ctattaatct tatcatatcc cgaggatatt tttgtcttgt actagg                      46

SEQ ID NO: 68           moltype = DNA   length = 47
FEATURE                 Location/Qualifiers
misc_feature            1..47
                        note = Oligonucleotide primer
source                  1..47
                        mol_type = other DNA
                        organism = synthetic construct
SEQUENCE: 68
ctaatgactg gctttttataa tatgagagag agaaaaaaat tactgac                    47

SEQ ID NO: 69           moltype = DNA   length = 20
FEATURE                 Location/Qualifiers
misc_feature            1..20
                        note = Oligonucleotide primer
source                  1..20
                        mol_type = other DNA
                        organism = synthetic construct
SEQUENCE: 69
aaaatctgtt agaactgttg                                                   20

SEQ ID NO: 70           moltype = DNA   length = 20
FEATURE                 Location/Qualifiers
misc_feature            1..20
                        note = Oligonucleotide primer
source                  1..20
                        mol_type = other DNA
                        organism = synthetic construct
SEQUENCE: 70
aagataaggc agttgaaatg                                                   20

SEQ ID NO: 71           moltype = DNA   length = 20
FEATURE                 Location/Qualifiers
misc_feature            1..20
```

```
                        note      = Oligonucleotide primer
source                  1..20
                        mol_type  = other DNA
                        organism  = synthetic construct
SEQUENCE: 71
tcaccatgtg aataaagtcc                                                    20

SEQ ID NO: 72           moltype = DNA   length = 19
FEATURE                 Location/Qualifiers
misc_feature            1..19
                        note      = Oligonucleotide primer
source                  1..19
                        mol_type  = other DNA
                        organism  = synthetic construct
SEQUENCE: 72
caaaaatgtg aagcttatc                                                     19

SEQ ID NO: 73           moltype = DNA   length = 42
FEATURE                 Location/Qualifiers
misc_feature            1..42
                        note      = Oligonucleotide primer
source                  1..42
                        mol_type  = other DNA
                        organism  = synthetic construct
SEQUENCE: 73
ctattaatct tatcatatcc cgaggatgca taattcgatt tc                           42

SEQ ID NO: 74           moltype = DNA   length = 45
FEATURE                 Location/Qualifiers
misc_feature            1..45
                        note      = Oligonucleotide primer
source                  1..45
                        mol_type  = other DNA
                        organism  = synthetic construct
SEQUENCE: 74
taatgactgg cttttataat atgagactat ttatctgctc atttc                        45

SEQ ID NO: 75           moltype = DNA   length = 19
FEATURE                 Location/Qualifiers
misc_feature            1..19
                        note      = Oligonucleotide primer
source                  1..19
                        mol_type  = other DNA
                        organism  = synthetic construct
SEQUENCE: 75
gagcttttt caaatcttc                                                      19

SEQ ID NO: 76           moltype = DNA   length = 18
FEATURE                 Location/Qualifiers
misc_feature            1..18
                        note      = Oligonucleotide primer
source                  1..18
                        mol_type  = other DNA
                        organism  = synthetic construct
SEQUENCE: 76
gaagtgatga atgagatg                                                      18

SEQ ID NO: 77           moltype = DNA   length = 19
FEATURE                 Location/Qualifiers
misc_feature            1..19
                        note      = Oligonucleotide primer
source                  1..19
                        mol_type  = other DNA
                        organism  = synthetic construct
SEQUENCE: 77
ctttctcatc aattgagac                                                     19

SEQ ID NO: 78           moltype = DNA   length = 19
FEATURE                 Location/Qualifiers
misc_feature            1..19
                        note      = Oligonucleotide primer
source                  1..19
                        mol_type  = other DNA
                        organism  = synthetic construct
SEQUENCE: 78
ctttgggttc taatttatc                                                     19

SEQ ID NO: 79           moltype = DNA   length = 44
FEATURE                 Location/Qualifiers
```

```
misc_feature              1..44
                          note = Oligonucleotide primer
source                    1..44
                          mol_type = other DNA
                          organism = synthetic construct
SEQUENCE: 79
ctattaatct tatcatatcc cgaggacgtt ggtgtatatt ttac              44

SEQ ID NO: 80             moltype = DNA  length = 46
FEATURE                   Location/Qualifiers
misc_feature              1..46
                          note = Oligonucleotide primer
source                    1..46
                          mol_type = other DNA
                          organism = synthetic construct
SEQUENCE: 80
ctaatgactg gcttttataa tatgagatag aaataaagga aaggac            46

SEQ ID NO: 81             moltype = DNA  length = 19
FEATURE                   Location/Qualifiers
misc_feature              1..19
                          note = Oligonucleotide primer
source                    1..19
                          mol_type = other DNA
                          organism = synthetic construct
SEQUENCE: 81
ttgctttaag gatagtttc                                          19

SEQ ID NO: 82             moltype = DNA  length = 20
FEATURE                   Location/Qualifiers
misc_feature              1..20
                          note = Oligonucleotide primer
source                    1..20
                          mol_type = other DNA
                          organism = synthetic construct
SEQUENCE: 82
agaagccaat aatgacgatg                                         20

SEQ ID NO: 83             moltype = DNA  length = 22
FEATURE                   Location/Qualifiers
misc_feature              1..22
                          note = Oligonucleotide primer
source                    1..22
                          mol_type = other DNA
                          organism = synthetic construct
SEQUENCE: 83
agaattctga tgatgcacag tc                                      22

SEQ ID NO: 84             moltype = DNA  length = 27
FEATURE                   Location/Qualifiers
misc_feature              1..27
                          note = Oligonucleotide primer
source                    1..27
                          mol_type = other DNA
                          organism = synthetic construct
SEQUENCE: 84
agcgccgcgg tgggatcctc tagagtc                                 27

SEQ ID NO: 85             moltype = DNA  length = 31
FEATURE                   Location/Qualifiers
misc_feature              1..31
                          note = Oligonucleotide primer
source                    1..31
                          mol_type = other DNA
                          organism = synthetic construct
SEQUENCE: 85
ctgcaggcat gcacatcatc aacttgaagg g                            31

SEQ ID NO: 86             moltype = DNA  length = 30
FEATURE                   Location/Qualifiers
misc_feature              1..30
                          note = Oligonucleotide primer
source                    1..30
                          mol_type = other DNA
                          organism = synthetic construct
SEQUENCE: 86
cccaccgcgg tggagatacg aacaaattag                              30

SEQ ID NO: 87             moltype = DNA  length = 27
```

```
FEATURE                 Location/Qualifiers
misc_feature            1..27
                        note = Oligonucleotide primer
source                  1..27
                        mol_type = other DNA
                        organism = synthetic construct
SEQUENCE: 87
gatagtaact ccttaattttt tatttgc                                              27

SEQ ID NO: 88           moltype = DNA   length = 58
FEATURE                 Location/Qualifiers
misc_feature            1..58
                        note = Oligonucleotide primer
source                  1..58
                        mol_type = other DNA
                        organism = synthetic construct
SEQUENCE: 88
gcaaataaaa attaaggagt tactatcatg acatattact tggaagaaga ggattttg            58

SEQ ID NO: 89           moltype = DNA   length = 45
FEATURE                 Location/Qualifiers
misc_feature            1..45
                        note = Oligonucleotide primer
source                  1..45
                        mol_type = other DNA
                        organism = synthetic construct
SEQUENCE: 89
ccttcaagtt gatgatgtgc atgcctgcag tcactcttcg tcttc                          45

SEQ ID NO: 90           moltype = DNA   length = 27
FEATURE                 Location/Qualifiers
misc_feature            1..27
                        note = Oligonucleotide primer
source                  1..27
                        mol_type = other DNA
                        organism = synthetic construct
SEQUENCE: 90
tgaccatgtt acacaagcct atatcct                                              27

SEQ ID NO: 91           moltype = DNA   length = 56
FEATURE                 Location/Qualifiers
misc_feature            1..56
                        note = Oligonucleotide primer
source                  1..56
                        mol_type = other DNA
                        organism = synthetic construct
SEQUENCE: 91
cgcccttatg ggatttatct tccttacttc gtttctttgc ataacttcgt cttaat              56

SEQ ID NO: 92           moltype = DNA   length = 23
FEATURE                 Location/Qualifiers
misc_feature            1..23
                        note = Oligonucleotide primer
source                  1..23
                        mol_type = other DNA
                        organism = synthetic construct
SEQUENCE: 92
taaggaagat aaatcccata agg                                                  23

SEQ ID NO: 93           moltype = DNA   length = 23
FEATURE                 Location/Qualifiers
misc_feature            1..23
                        note = Oligonucleotide primer
source                  1..23
                        mol_type = other DNA
                        organism = synthetic construct
SEQUENCE: 93
ttcacgttac taaagggaat gta                                                  23

SEQ ID NO: 94           moltype = DNA   length = 57
FEATURE                 Location/Qualifiers
misc_feature            1..57
                        note = Oligonucleotide primer
source                  1..57
                        mol_type = other DNA
                        organism = synthetic construct
SEQUENCE: 94
tctcacattcc cttagtaac gtgaaccatg accatttat aggtttagat gtttatg              57
```

```
SEQ ID NO: 95              moltype = DNA  length = 24
FEATURE                    Location/Qualifiers
misc_feature               1..24
                           note = Oligonucleotide primer
source                     1..24
                           mol_type = other DNA
                           organism = synthetic construct
SEQUENCE: 95
cggtgttcct ccatatatct acgc                                              24

SEQ ID NO: 96              moltype = DNA  length = 27
FEATURE                    Location/Qualifiers
misc_feature               1..27
                           note = Oligonucleotide primer
source                     1..27
                           mol_type = other DNA
                           organism = synthetic construct
SEQUENCE: 96
cgctaaactc aacaggtgat ccgattg                                           27
```

METHODS AND STRAIN

CROSS-REFERENCE TO RELATED APPLICATIONS

This application is a continuation of U.S. patent application Ser. No. 16/469,784, filed Jun. 14, 2019, which is a § 371 U.S. national stage patent application of PCT Patent Application No. PCT/EP2017/083601, filed Dec. 19, 2017, which claims priority to European Patent Application No. 16205055.3, filed Dec. 19, 2016, the contents of each which are hereby incorporated by reference in their entireties.

REFERENCE TO A SEQUENCE LISTING

The contents of the electronic submission of the text file Sequence Listing, named "NB41019USCNT_SequenceListing.xml" was created on Jun. 21, 2023, and is 119 KB in size, which is hereby incorporated by reference in its entirety.

FIELD OF THE INVENTION

The present invention relates to a method for transforming a strain of the *Lactococcus* genus through natural competence. The present invention further relates to strains obtained or obtainable by said method. The present invention also relates to a method for identifying a strain of the *Lactococcus* genus which is transformable through natural competence.

BACKGROUND TO THE INVENTION

*Lactococcus lactis* is one of the most important lactic acid bacteria used in the dairy industry, in particular as a main dairy starter species in various cheese preparations (e.g. gouda, cheddar, brie, parmesan, roquefort) and fermented milk products (e.g. buttermilk, sour cream). Other applications of *L. lactis* bacteria include as a host for heterologous protein production or as a delivery platform for therapeutic molecules. While the growth and fermentation properties of *L. lactis* have been gradually improved by selection and classical methods, there is great potential for further improvement through natural processes or by genetic engineering. Of particular interest are methods to naturally transform *L. lactis* without the use of genetic engineering, thereby generating new non-GMO strains with useful industrial properties.

*Lactococcus raffinolactis* is present in a wide range of environments, such as foods (meat, fish, milk, vegetable), animals, and plant materials. In the dairy environment, this species has been found in raw milks (cow, ewe, goat, and camel), natural dairy starter cultures, and a great variety of cheeses. The prevalence of this bacterium in foods even if with a "nondominant" status compared to other lactococci could make it a candidate for future development of starter cultures.

DNA acquisition by natural transformation is widespread among prokaryotes and has been identified in over 80 species. Various functions are attributed to competence for natural transformation: genome plasticity, DNA repair, and/or nutrition. In Gram-positive bacteria, competence for natural transformation has been well-characterized in *Bacillus subtilis* and in various species of the genus *Streptococcus* (e.g. *S. pneumoniae*, *S. mutans*, and *S. thermophilus*).

In streptococci, competence for DNA transformation is induced in response to secreted signalling peptides referred to as competence pheromones/alarmones. The production of this class of cell-to-cell communication molecules is initiated in response to specific environmental stresses or conditions and allows the coordination of physiological functions (e.g. competence, predation, biofilm formation). Above a threshold concentration, competence pheromones activate the master regulator ComX (alternative sigma factor ax), which ultimately leads to a transcriptional reprogramming of cells (globally known as late competence phase) including the induction of genes strictly required for DNA transformation. ComX binds to a specific DNA sequence named Com-box or Cin-box, which is located at least in the vicinity of promoters of late competence (com) genes/operons responsible for DNA uptake (e.g.; comG, comF and comE operons), DNA protection (e.g. ssb) and DNA recombination (e.g. recA, dprA, coiA), and positively controls their expression.

The early steps leading to competence activation (early competence phase) differs among bacteria. In streptococci, two major peptide-based signaling pathways—i.e. ComCDE and ComRS—have been identified so far. In *mitis* and *anginosus* groups of streptococci (*S. pneumoniae* as paradigm), the competence signaling peptide (CSP, or mature ComC) triggers a phosphorylation cascade mediated by the two-component system ComD-ComE, leading to the transcriptional activation of comX. In *salivarius, mutans, pyogenes, bovis* and suis groups of streptococci, another regulation mechanism is operational (*S. thermophilus* as paradigm). This system involves the ComX-induction peptide (XIP, or mature ComS) which is internalized by the oligopeptide transporter Opp, binds to and activates the regulator ComR, and in turn induces comX transcription.

Orthologues of comX and of all late com genes essential for natural transformation have been identified in the genome of *L. lactis*, although some are present as putative pseudogenes in different strains (Wydau et al., 2006).

Specific growth conditions have been reported to activate com genes in *Lactococcus lactis*. For example, the promoter of comX was shown to be induced during cheese-making conditions in strain MG5267 (an MG1363 derivative) which belongs to the subspecies *cremoris* (Bachmann et al. 2010).

In the *L. lactis* subspecies (subsp.) *lactis*, carbon starvation was shown to activate six late com genes in strain IL1403 of dairy origin (i.e. comX, comEA, comGA, comGB, radA, and nucA) and most of the late essential com genes in strain KF147 of plant origin (i.e. comX, comC, coiA, and operons comG, comE, comF) (Ercan et al., 2015). However, when the authors attempted to validate functional natural transformation in KF147, they were unsuccessful.

Wydau et al. reported that all the well-established late genes/operons display an upstream and conserved Com-box, suggesting that they are similarly controlled by ComX as reported in streptococci. However, the authors did not comment on whether comX over-expression in IL1403 induced natural competence. Indeed, the authors neither report any experiment evaluating natural competence in this strain nor suggest any experimental conditions appropriate for inducing natural competence. Thus, as noted in the recent literature (see Ercan et al., 2015) [i.e., 9 years after Wydau et al.], there is no experimental evidence for successful transformation of any species of the genus *Lactococcus* by natural competence, and even less of IL1403.

Accordingly, there remains a need for a method for naturally transforming *Lactococcus* strains using natural competence. In addition, since some strains of the *Lactococcus* genus may not encode a full set of functional late com genes, there is a need for a method for identifying *Lactococcus* strains which can be transformed by natural competence.

SUMMARY OF THE INVENTION

In a first aspect, the present invention provides a method for transforming a strain of the *Lactococcus* genus with an exogenous DNA polynucleotide comprising the steps of:
  (a) providing a strain of the *Lactococcus* genus, wherein said strain is transformable through natural competence;
  (b) modulating the production of a ComX protein in said strain;
  (c) contacting said strain of step (b) with an exogenous DNA polynucleotide in a medium and incubating the resulting mixture for integration of the exogenous DNA polynucleotide into the genome of said strain; and
  (d) selecting a strain which has integrated the exogenous DNA polynucleotide into its genome.

In one embodiment, the step of modulating the production of a ComX protein is performed by expressing a comX gene in said strain or increasing the expression of a comX gene in said strain.

In a further embodiment, the comX gene is an exogenous comX gene. Said exogenous comX gene may be transferred into said strain by conjugation, transduction, or transformation. Said exogenous comX gene may be operably linked to transcription regulator(s).

In an alternative embodiment, said comX gene is the endogenous comX gene of said strain.

In one embodiment, when said comX gene is the endogenous comX gene of said strain, the method comprises:
  (a) providing a strain of the *Lactococcus* genus, wherein said strain is transformable through natural competence;
  (b) modulating the production of a ComX protein, by expressing the endogenous comX gene or increasing the expression of the endegenous comX of said strain;
  (c) contacting said strain of step (b) with an exogenous DNA polynucleotide in a medium and incubating the resulting mixture for integration of the exogenous DNA polynucleotide into the genome of said strain; and
  (d) selecting a strain which has integrated the exogenous DNA polynucleotide into its genome,
  wherein step (c) is carried out after step (b) or wherein step (b) and step (c) are carried out simultaneously.

In some embodiments, said ComX protein has the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, or has at least 90% identity or at least 90% similarity to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 or SEQ ID NO:22. In some embodiments, said ComX protein has the amino acid sequence of SEQ ID NO:2, SEQ ID NO:4, SEQ ID NO:6, or has at least 90% identity or at least 90% similarity to the amino acid sequence of SEQ ID NO:2, SEQ ID NO:4 or SEQ ID NO:6.

In some embodiments, said comX gene has the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, or has at least 90% identity to the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19 or SEQ ID NO:21.

In some embodiments, said comX gene has the nucleotide sequence of SEQ ID NO:1, SEQ ID NO:3, SEQ ID NO:5, or has at least 90% identity to the nucleotide sequence of SEQ ID NO:1, SEQ ID NO:3 or SEQ ID NO:5.

In some embodiments, the medium of step (c) is a chemically defined medium. In a preferred embodiment the chemically defined medium (CDM) comprises 0.5 g/L $NH_4Cl$, 9.0 g/L $KH_2PO_4$, 7.5 g/L $K_2HPO_4$, 0.2 g/L $MgCl_2$, 5 mg/L $FeCl_2$, 50 mg/L $CaCl_2$, 5 mg/L $ZnSO_4$, 2.5 mg/L $CoCl_2$, 0.05 g/L tyrosine, 0.1 g/L asparagine, 0.1 g/L cysteine, 0.1 g/L glutamine, 0.1 g/L isoleucine, 0.1 g/L leucine, 0.1 g/L methionine, 0.1 g/L tryptophan, 0.1 g/L valine, 0.1 g/L histidine, 0.2 g/L arginine, 0.2 g/L glycine, 0.2 g/L lysine, 0.2 g/L phenylalanine, 0.2 g/L threonine, 0.3 g/L alanine, 0.3 g/L proline, 0.3 g/L serine, 10 mg/L paraaminobenzoic acid, 10 mg/L biotin, 1 mg/L folic acid, 1 mg/L nicotinic acid, 1 mg/L panthotenic acid, 1 mg/L riboflavin, 1 mg/L thiamine, 2 mg/L pyridoxine, 1 mg/L cyanocobalamin, 5 mg/L orotic acid, 5 mg/L 2-deoxythymidine, 5 mg/L inosine, 2.5 mg/L dl-6,8-thioctic acid, 5 mg/L pyridoxamine, 10 mg/L adenine, 10 mg/L guanine, 10 mg/L uracil, 10 mg/L xanthine, and 5 g/L glucose.

In some embodiments, prior to step (c) said strain is incubated in a pre-culture medium, preferably wherein the pre-culture medium is a complex medium, more preferably wherein the pre-culture medium is M17G or THBG.

In some embodiments of the present invention, said strain is incubated with the exogenous DNA polynucleotide for around 4 to 8 hours at around 30° C. and said medium of step (c) is supplemented with an osmo-stablizer, preferably wherein the osmo-stablizer is glycerol or mannitol, more preferably wherein the osmo-stabilizer is 5% [v/v] glycerol or 5% [w/v] mannitol.

In some embodiments, said exogenous DNA polynucleotide is from a strain of the *Lactococcus lactis* species.

In some embodiments, said exogenous DNA polynucleotide is from a strain of the *Lactococcus* raffinolactis species.

In some embodiments, said strain of step (a) is a *Lactoccocus lactis* subsp. *cremoris* strain.

In another aspect, the present invention provides a strain of the *Lactococcus* genus obtained or obtainable by the method of the first aspect of the present invention.

In one embodiment, said strain of the *Lactococcus* genus is a strain of the *Lactococcus lactis* or *Lactococcus raffinolactis* species.

In a further aspect, the present invention provides a method for identifying a strain of the *Lactococcus* genus which is transformable through natural competence comprising the steps of:
  (a) providing a strain of the *Lactococcus* genus species;
  (b) transforming said strain with a plasmid expressing a comX gene having at least 90% identity, preferably having 100% identity, to the endogenous comX gene of said strain;
  (c) contacting said strain obtained in step (b) with an exogenous DNA polynucleotide encoding a marker gene in a medium and incubating the resulting mixture for integration of the exogenous DNA polynucleotide into the genome of said strain; and
  (d) determining the rate of recombination events;
wherein a rate of at least $1\times10^{-6}$ transformants per µg of DNA is indicative of a strain which is transformable through natural competence.

In a particular embodiment of method for transforming a strain of the *Lactococcus* genus of the present invention, said strain of step (a) is identified using the method for identifying a strain of the *Lactococcus* genus which is transformable through natural competence according to the present invention. In some embodiments of the present invention, said strain of step (a) is identified using Assay A.

DESCRIPTION OF THE DRAWINGS

FIG. 1: Table showing the status of genes involved in natural competence for *L lactis* strains MG1363, SK11, KW2, IL 1403, SL 12651 and SL 12653.

Late com genes in the complete genomes of strains MG1363, SK11, and KW2 of *Lactococcus lactis* subsp. *cremoris* and of strain IL 1403, SL 12651 and SL 12653 of *Lactococcus lactis* subsp. *lactis*. Origin is indicated above strain names. Gene-associated function in DNA transformation is indicated on the left. Reg. denotes regulation. The complete and incomplete status of late genes is based on blastp and tblastn homology searches (blast.ncbi.nlm.nih.gov/Blast.cgi) using orthologues of *S. pneumoniae* TIGR4 and *S. thermophilus* LMD-9 and default parameters. + denotes the presence of a complete gene; * denotes the presence of an incomplete gene due to nucleotide(s) exchange, insertion or deletion resulting in a premature stop codon; and Tn denotes a disrupted gene by the insertion of at least one transposon.

Figure 2:
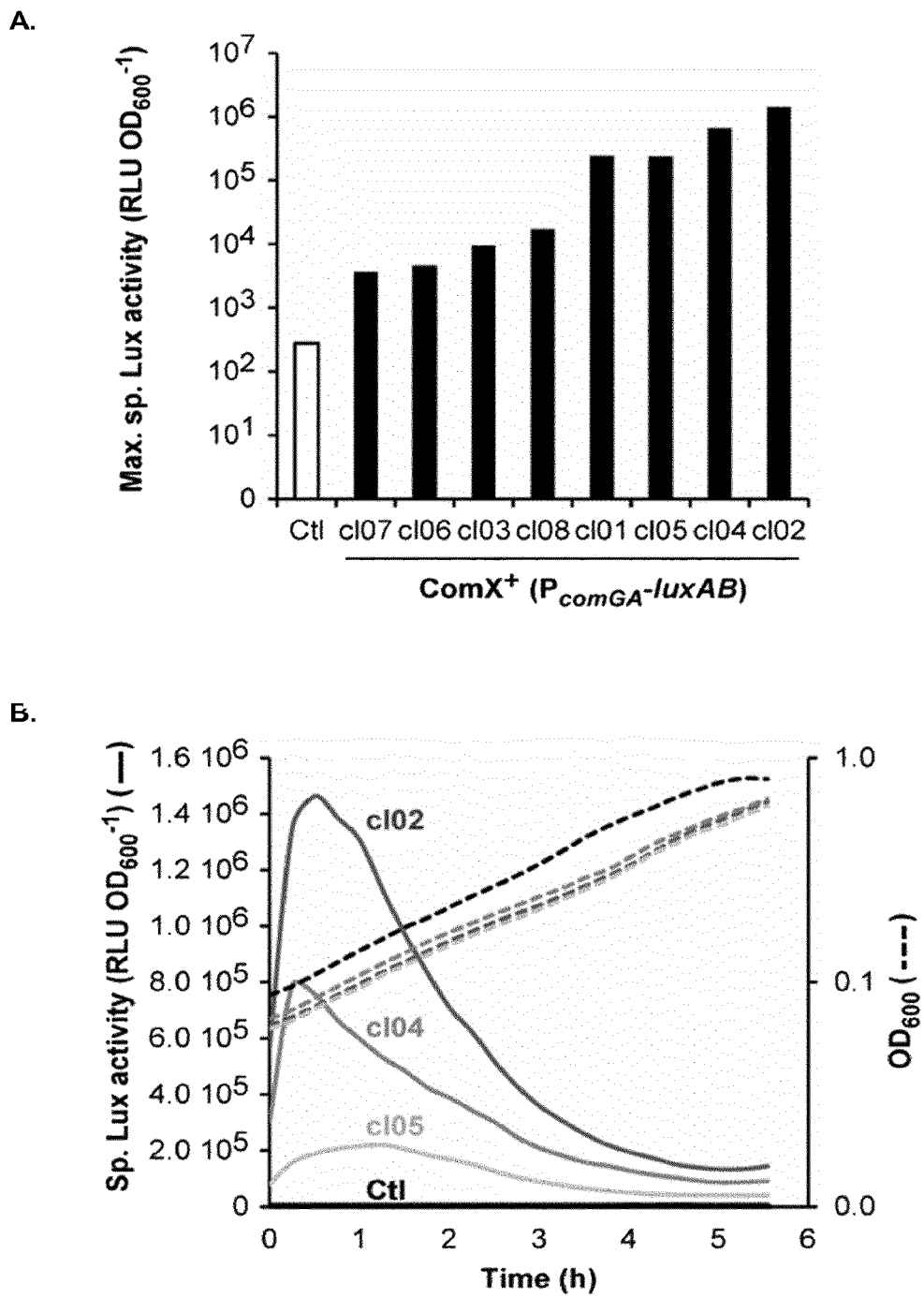
Figure 2:
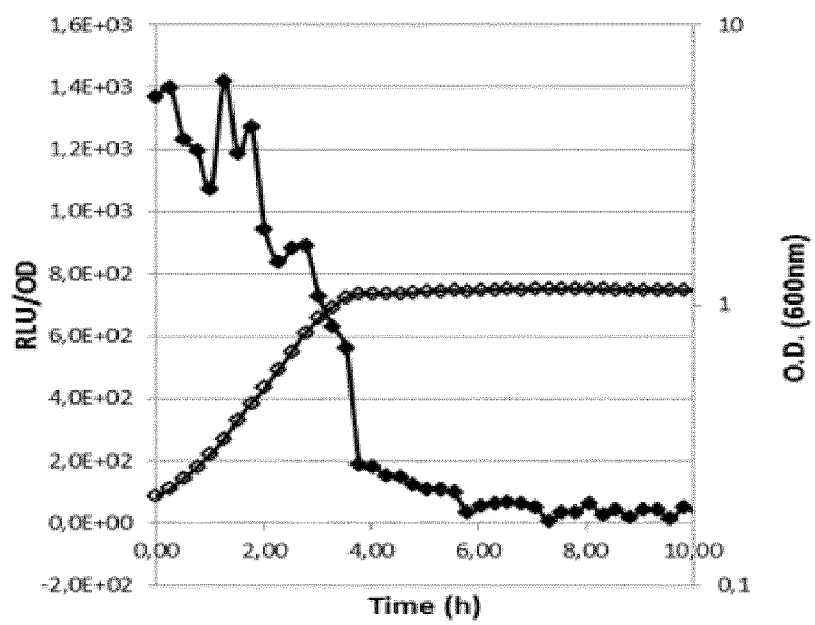
Figure 2:
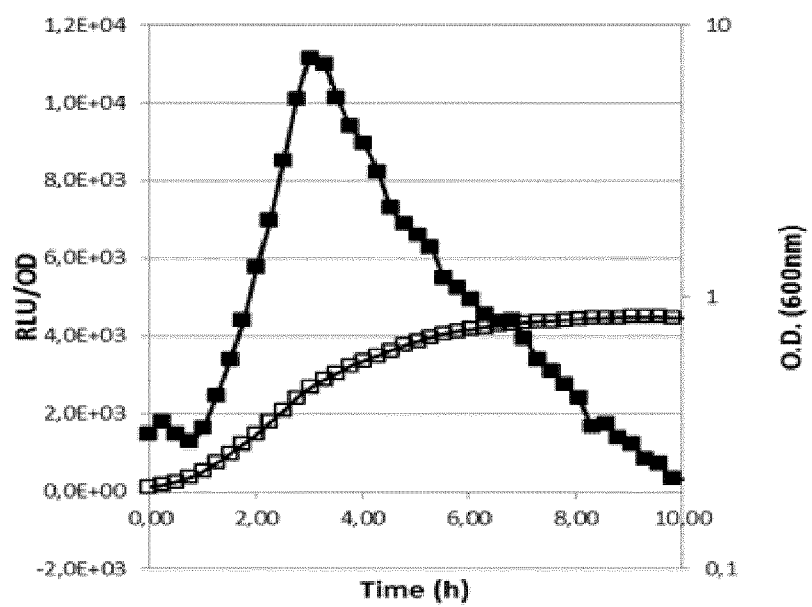

FIG. 2: Graphs displaying the results of luciferase assays which demonstrate the activation of a reporter construct comprising the late promoter $P_{comGA}$ driven by constitutive comX overexpression (A) Maximum specific luciferase (Lux) activity (RLU $OD_{600}^{-1}$) emitted by eight independent clones (cl01 to cl08) of the KW2-derived reporter strain (BLD101, $P_{comGA[MG]-lux}AB$) carrying plasmid pGhP32comX$_{MG}$ compared to the control strain (Ctl) carrying the empty vector pG+host9. (B) Kinetics of specific Lux activity (solid line) during growth (RLU/OD600; dotted line) for the control strain (Ctl; black lines) and three selected clones (BLD101 [pGhP32comX$_{MG}$], cl02, cl04 and cl05; gray lines). (C) Kinetics of specific luciferase activity (closed symbols) during growth (RLU/OD600; open symbols) of the MG1363+pGhP32comX$_{MG}$-P$_{comGA[MG]}$-luc, grown in M17G at 30° C. (D) Kinetics of specific luciferase activity (closed symbols) during growth (RLU/OD600; open symbols) of IL1403+pGhP32comX$_{IO}$-P$_{comGA[IO]}$-luc strains, grown in M17G at 30° C.

Figure 3:
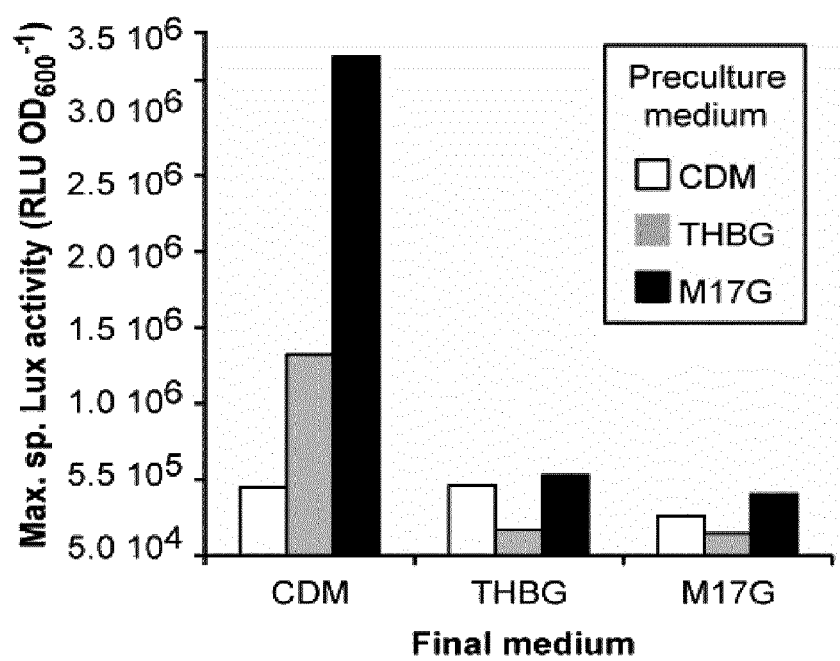

FIG. 3: Graphs displaying the results of luciferase assays which demonstrate the impact of growth medium on $P_{comGA}$ activation Maximum specific Lux activity of BLD101 [pGhP32comX$_{MG}$] cl02 grown in different final culture media (CDM, THBG, and M17G) according to preculture conditions (CDM, THBG, and M17G). Overnight precultures were 10-fold diluted in the pre-culture medium and grown for 2 hours. Then, cells were washed twice in distilled water and the $OD_{600}$ was adjusted to 0.05 in the final growth medium before measuring growth and luciferase activity. One representative experiment of two independent replicates.

Figure 4:
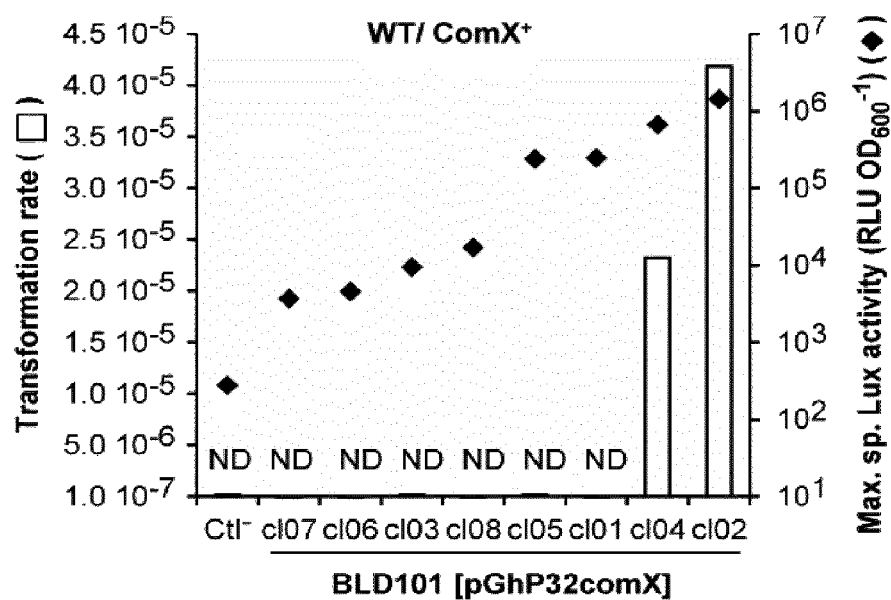

FIG. 4: Results of a transformation assay implemented on a *L. lactis* subsp. *cremoris* KW2 constitutively expressing comX contacted with a DNA consisting of a mutated allele of the rpsL gene as exogenous DNA polynucleotide (A) Alignment of the rpsL gene sequences of strain MG1363, a spontaneous streptomycin-resistant clone of strain MG1363, strain KW2 and a KW2-derived transformant obtained using the method of the invention (partial sequence). The arobase, pound and dollar signs below the alignment indicate the positions of nucleotide differences existing between the rpsL sequences. The dollar sign at position 167 indicates the point mutation (A→T; strA1 allele) responsible for the streptomycin-resistance phenotype; the pound sign at position 156 highlights a nucleotide that is naturally different between MG1363 and KW2 (T in KW2, A in MG1363); the arobase sign at position 39 indicates a silent nucleotide substitution (T→G) which is found in the streptomycin-resistant clone derived from MG1363. (B) DNA transformation with the strA1 allele was assessed for *L. lactis* strains constitutively expressing ComX. Transformation rate (white bars) and maximum specific luciferase (Lux) activity (black diamonds, RLU $OD_{600}^{-1}$, as reported in FIG. 2) of eight clones (cl01 to cl08) of the reporter strain (BLD101, $P_{comGA[MG]}$-luxAB) carrying plasmid pGhP32comX$_{MG}$ compared to the negative control strain (Ctl-) carrying the empty vector (BLD101 [pG+host9]).

Figure 5:
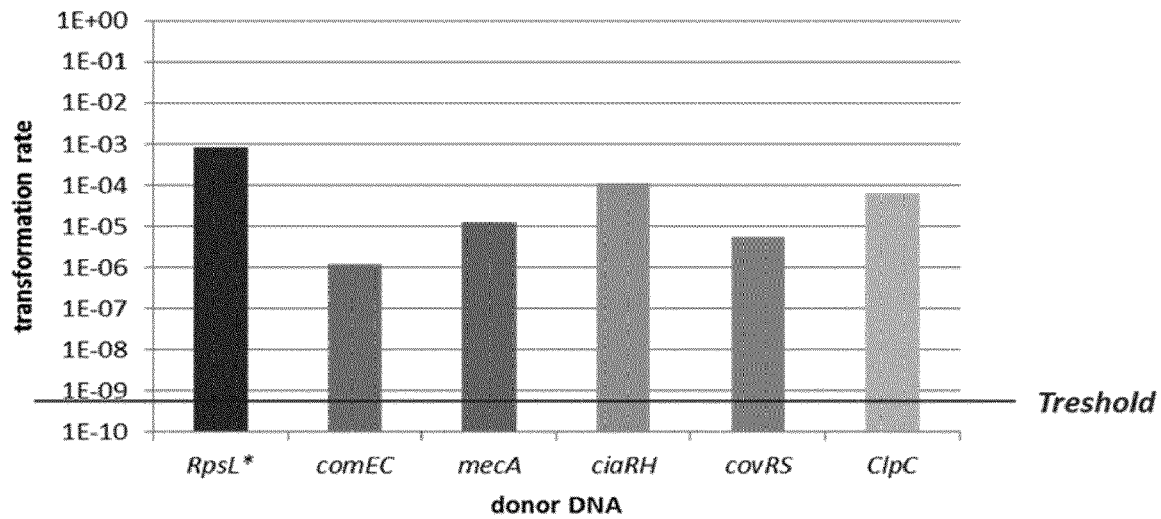

FIG. 5: Graphs displaying the results of transformation rate of the KW2 derivative BLD101 [pGhP32comX$_{MG}$] obtained with overlap PCR products (comEC, mecA, ciaRH, covRS and clpC) and strA1 (rpsL*)-donor DNA.

The threshold represents the theoretical transformation rate to obtain only one transformant.

Figure 6:
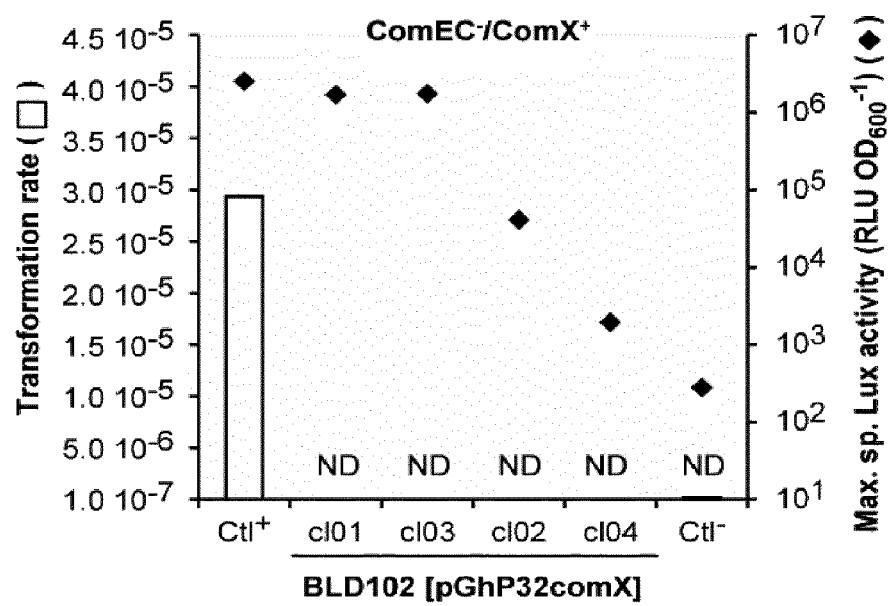

FIG. 6: Graphs depicting the results of transformation assays for a *L. lactis* subsp. *cremoris* deleted in its comEC gene and constitutively expressing comX.

DNA transformation with the strA1 allele was assessed for *L. lactis* strains constitutively expressing comX. Transformation rate (white bars) and maximum specific luciferase (Lux) activity (RLU $OD_{600}^{-1}$) of four clones (cl01 to cl04) of the ComEC-deficient reporter strain (BLD102, $P_{comGA[MG]}$-luxAB) carrying plasmid pGhP32comX$_{MG}$ compared to the positive (Ctl+, BLD101 [pGhP32comX$_{MG}$] cl02) and negative (Ctl-, BLD101 [pG+host9]) control strains. Transformability was assessed according to the standard protocol described in Materials and Methods using strA1-carrying PCR products as donor DNA. ND denotes a transformation rate below the detection level of spontaneous $Str^r$ mutants ($<10^{-7}$). One representative experiment of two independent replicates.

Figure 7:
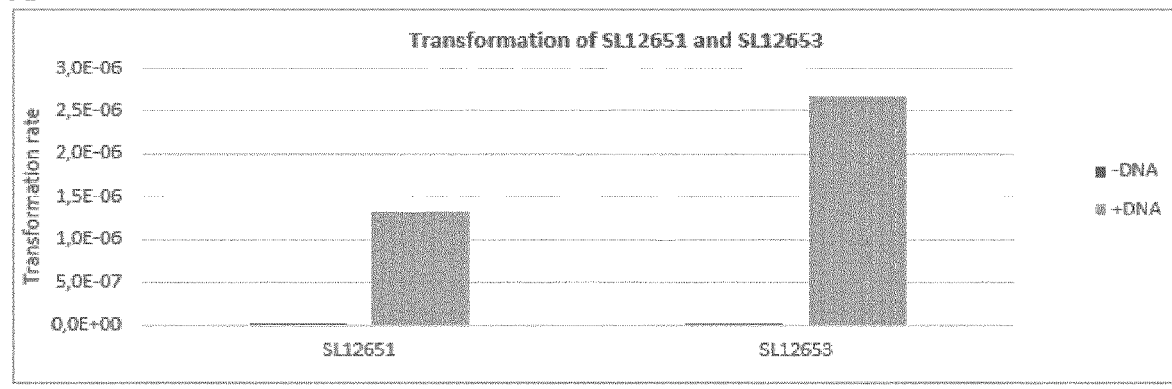
Figure 7:
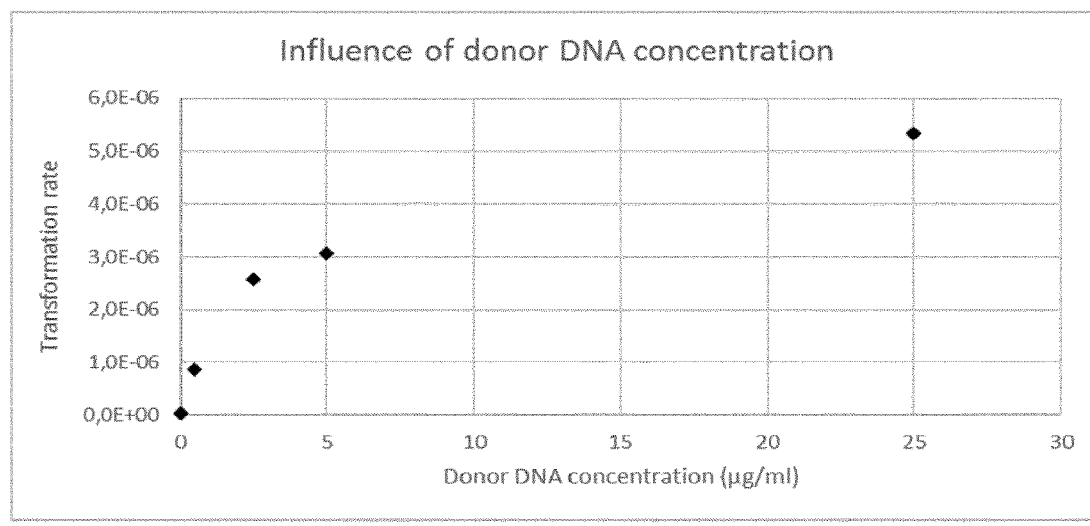
Figure 7:
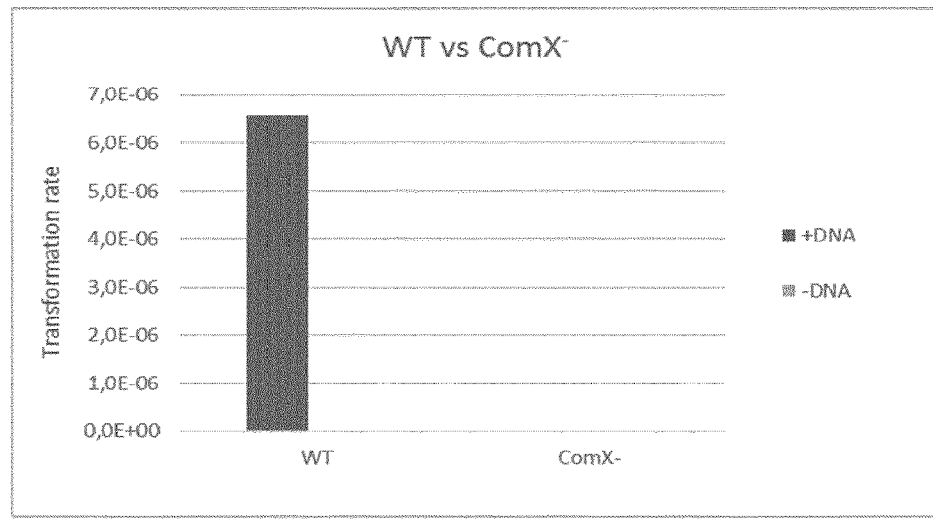

FIG. 7: Graphs displaying natural competence in *Lactococcus lactis* subsp. *lactis* SL12651 and 12653 strains.

(A) Transformation rate of *L. lactis* subsp. *lactis* SL12651 and 12653 strains in M17G medium, with rpsL* donor DNA (+DNA) or without donor DNA (-DNA); (B) DNA transformation with increasing initial concentration of donor DNA assessed in SL12653 strain; (C) Comparison of transformation rates between wild-type (WT) SL12653 strain and a SL12653 strain deleted for the comX gene (ComX-); transformation rate of three clones of the ComX-deficient strain compared to the WT strain, in presence (+DNA) or in absence (-DNA) of donor DNA.

DETAILED DESCRIPTION

The present invention is based on the observation that overexpression of ComX in a strain of the *Lactococcus* genus allowed to transform this strain by natural competence. Using this approach a *L. lactis* strain was generated by natural transformation with an exogenous DNA polynucleotide. Importantly, these results are the first demonstration of transformation of a *L. lactis* strain by natural competence. Further, existence of natural competence in the *Lactococcus* genus has been confirmed in two strains of the *Lactococcus raffinolactis* species and two *Lactococcus lactis* species.

The practice of the present invention will employ, unless otherwise indicated, conventional techniques of molecular biology, biochemistry, microbiology, bacteriology, and related fields, which are within the capabilities of a person of ordinary skill in the art. Such techniques are explained in the literature.

Thus, the present invention provides a method for transforming a strain of the *Lactococcus* genus with an exogenous DNA polynucleotide comprising the steps of:
 (a) providing a strain of the *Lactococcus* genus, wherein said strain is transformable through natural competence;
 (b) modulating the production of a ComX protein in said strain;
 (c) contacting said strain of step (b) with an exogenous DNA polynucleotide in a medium and incubating the resulting mixture for integration of the exogenous DNA polynucleotide into the genome of said strain; and
 (d) selecting a strain which has integrated the exogenous DNA polynucleotide into its genome.

As detailed below, step (b) and step c) can be carried out sequentially [i.e., step (b) and then step (c)] or in another embodiment step (b) and step (c) can be carried out simultaneously.

*Lactococcus* Genus

The present invention relates to a method for transforming a strain of the *Lactococcus* genus, a Gram-positive bacterium. *Lactococcus* strains are known as lactic acid bacteria (LAB) for their ability to convert carbohydrate to lactic acid. A strain of the *Lactococcus* genus and *Lactococcus* strain are used herein interchangeably.

The *Lactococcus* genus comprises, but is not limited to the following species: *Lactococcus chungangensis, Lactococcus fujiensis, Lactococcus garvieae, Lactococcus lactis, Lactococcus piscium, Lactococcus plantarum* and *Lactococcus raffinolactis*. Any strain of one of these species may be used in the current invention, provided that this strain is transformable through natural competence as defined herein.

In a particular embodiment, said strain of the *Lactococcus* genus of step a) is a strain of the *Lactococcus lactis* species or a strain of the *Lactococcus raffinolactis* species.

*Lactococcus lactis*

In a particular embodiment, said strain of the *Lactococcus* genus of step a) is a strain of the *Lactococcus lactis* species. The species *Lactococcus lactis* comprises several subspecies. Thus, when the strain of the *Lactococcus* genus of step a) is a strain of the *Lactococcus lactis* species, said strain is selected in the group consisting of *Lactococcus lactis* subsp. *cremoris, Lactococcus lactis* subsp. *hordniae, Lactococcus lactis* subsp. *lactis* and *Lactococcus lactis* subsp. *tructae*. As used herein a strain of the *Lactococcus lactis* species is understood to be a genetic variant or subtype of any *L. lactis* species or subspecies. The different *Lactococcus lactis* subspecies disclosed here, and in particular the *lactis* and the *cremoris* subspecies, are defined herein based on DNA sequences coding for 16S ribosomal RNA [Ward et al., 1998].

In a particular aspect, the present invention provides a method for transforming a strain of the *Lactococcus lactis* species with an exogenous DNA polynucleotide comprising the steps of:
 (a) providing a strain of the *Lactococcus lactis* species, wherein said strain is transformable through natural competence;
 (b) modulating the production of a ComX protein in said strain;
 (c) contacting said strain of step (b) with an exogenous DNA polynucleotide in a medium and incubating the resulting mixture for integration of the exogenous DNA polynucleotide into the genome of said strain; and
 (d) selecting a strain which has integrated the exogenous DNA polynucleotide into its genome.

In a preferred embodiment, the strain of step (a) is a *Lactococcus lactis* subsp. *cremoris* strain or a *Lactococcus lactis* subsp. *lactis* strain. Both subspecies have been identified and characterised with full genome sequences—see, e.g., Wegmann et al. (2007) *J. Bacteriol.* 189:3256-3270 and Bolotin et al. (2001) *Genome Res.* 11:731-753. With regards to the dairy industry, *L. lactis* subsp. *lactis* (previously known as *Streptococcus lactis*) is preferred for making soft cheese while *L. lactis* subsp. *cremoris* (previously known as *Streptococcus cremoris*) is preferred for hard cheese production.

In a preferred embodiment, the strain of step (a) is *Lactococcus lactis* subsp. *cremoris* strain.

In another preferred embodiment, the strain of step (a) is *Lactococcus lactis* subsp. *lactis* strain.

*Lactococcus raffinolactis*

In a particular embodiment, said strain of the *Lactococcus* genus of step a) is a strain of the *Lactococcus raffinolactis* species.

In a particular aspect, the present invention provides a method for transforming a strain of the *Lactococcus raffinolactis* species with an exogenous DNA polynucleotide comprising the steps of:
 (a) providing a strain of the *Lactococcus raffinolactis* species, wherein said strain is transformable through natural competence;
 (b) modulating the production of a ComX protein in said strain;
 (c) contacting said strain of step (b) with an exogenous DNA polynucleotide in a medium and incubating the resulting mixture for integration of the exogenous DNA polynucleotide into the genome of said strain; and
 (d) selecting a strain which has integrated the exogenous DNA polynucleotide into its genome.

*Lactococcus plantarum*

In a particular embodiment, said strain of the *Lactococcus* genus of step a) is a strain of the *Lactococcus plantarum* species.

In a particular aspect, the present invention provides a method for transforming a strain of the *Lactococcus plantarum* species with an exogenous DNA polynucleotide comprising the steps of:
 (a) providing a strain of the *Lactococcus plantarum* species, wherein said strain is transformable through natural competence;
 (b) modulating the production of a ComX protein in said strain;
 (c) contacting said strain of step (b) with an exogenous DNA polynucleotide in a medium and incubating the resulting mixture for integration of the exogenous DNA polynucleotide into the genome of said strain; and (d) selecting a strain which has integrated the exogenous DNA polynucleotide into its genome.

*Lactococcus piscium*

In a particular embodiment, said strain of the *Lactococcus* genus of step a) is a strain of the *Lactococcus piscium* species.

In a particular aspect, the present invention provides a method for transforming a strain of the *Lactococcus piscium* species with an exogenous DNA polynucleotide comprising the steps of:
  (a) providing a strain of the *Lactococcus piscium* species, wherein said strain is transformable through natural competence;
  (b) modulating the production of a ComX protein in said strain;
  (c) contacting said strain of step (b) with an exogenous DNA polynucleotide in a medium and incubating the resulting mixture for integration of the exogenous DNA polynucleotide into the genome of said strain; and
  (d) selecting a strain which has integrated the exogenous DNA polynucleotide into its genome.

*Lactococcus garvieae*

In a particular embodiment, said strain of the *Lactococcus* genus of step a) is a strain of the *Lactococcus garvieae* species.

In a particular aspect, the present invention provides a method for transforming a strain of the *Lactococcus garvieae* species with an exogenous DNA polynucleotide comprising the steps of:
  (a) providing a strain of the *Lactococcus garvieae* species, wherein said strain is transformable through natural competence;
  (b) modulating the production of a ComX protein in said strain;
  (c) contacting said strain of step (b) with an exogenous DNA polynucleotide in a medium and incubating the resulting mixture for integration of the exogenous DNA polynucleotide into the genome of said strain; and
  (d) selecting a strain which has integrated the exogenous DNA polynucleotide into its genome.

*Lactococcus fujiensis*

In a particular embodiment, said strain of the *Lactococcus* genus of step a) is a strain of the *Lactococcus fujiensis* species.

In a particular aspect, the present invention provides a method for transforming a strain of the *Lactococcus fujiensis* species with an exogenous DNA polynucleotide comprising the steps of:
  (a) providing a strain of the *Lactococcus fujiensis* species, wherein said strain is transformable through natural competence;
  (b) modulating the production of a ComX protein in said strain;
  (c) contacting said strain of step (b) with an exogenous DNA polynucleotide in a medium and incubating the resulting mixture for integration of the exogenous DNA polynucleotide into the genome of said strain; and
  (d) selecting a strain which has integrated the exogenous DNA polynucleotide into its genome.

*Lactococcus chungangensis*

In a particular embodiment, said strain of the *Lactococcus* genus of step a) is a strain of the *Lactococcus chungangensis* species.

In a particular aspect, the present invention provides a method for transforming a strain of the *Lactococcus chunganensis* species with an exogenous DNA polynucleotide comprising the steps of:
  (a) providing a strain of the *Lactococcus chungangensis* species, wherein said strain is transformable through natural competence;
  (b) modulating the production of a ComX protein in said strain;
  (c) contacting said strain of step (b) with an exogenous DNA polynucleotide in a medium and incubating the resulting mixture for integration of the exogenous DNA polynucleotide into the genome of said strain; and
  (d) selecting a strain which has integrated the exogenous DNA polynucleotide into its genome.

DNA Acquisition

Bacteria may naturally acquire exogenous DNA via one of three possible mechanisms: transformation, conjugation, or transduction.

As used herein the term "transformation" refers to the uptake of exogenous genetic material (e.g. a DNA polynucleotide) from the external medium. Since transformation requires that genetic material cross the bacterial cell wall and membrane and the uptake of exogenous genetic material is energetically costly, the process is tightly regulated. Accordingly, bacterial cells may only be transformed under certain conditions. Bacterial cells which are in a transformable state are said to be competent.

Competence may be artificially induced in the laboratory, e.g. by electroporation or exposure to divalent cations (e.g. $CaCl_2$) and heat shock. Alternatively, some species of bacteria express a proteinaceous machinery that provides natural competence; this system of natural competence has been widely studied in streptococci.

As used herein the term "conjugation" refers to the transfer of genetic material between bacterial cells.

As used herein the term "transduction" refers to the transfer of genetic material from a virus (e.g. a bacteriophage) or a viral vector into bacterial cell.

ComX Protein

The method of the present invention comprises the step of modulating the production of a ComX protein in said strain.

ComX protein is an alternative sigma factor, also known as $\sigma^x$, which acts as master regulator for the late com genes and is responsible for transcriptional reprogramming of cells including the induction of genes strictly required for DNA transformation (Lee et al., 1989; Petersen et al. 2004).

ComX may bind to a specific target sequence (or box) termed the Com-box (or Cin-box). Com-boxes are located in the vicinity of the promoters of late competence (com) genes/operons responsible for DNA uptake (e.g., comG, comF, and comE operons), DNA protection (e.g. ssb) and DNA recombination (e.g. recA, dprA, coiA), and positively controls their expression (Campbell et al., 1998; Luo and Morrison, 2003).

The production of the ComX protein in a strain of interest may be increased relatively to an appropriate control strain, i.e., the *Lactococcus* strain in which the production of the ComX protein has not been modulated. ComX protein may be produced (expressed) following modulation as compared to an appropriate control strain, i.e., the *Lactococcus* strain in which the ComX protein is not produced.

In some embodiments, the production of the ComX protein is constitutive or inducible.

The production of ComX protein may be monitored using any method known in the art. For example, by western blotting using an antibody specific for the ComX protein. Alternatively, comX gene mRNA transcript levels may be measured by qPCR.

Alternatively, the ComX protein may be monitored using a reporter construct polynucleotide, e.g. as described in the Example 1 and Materials and Methods. The reporter construct polynucleotide may comprise genes encoding one or more reporter proteins, preferably the genes encoding the reporter proteins are operably linked to a promoter comprising a Com-box sequence. The reporter proteins may be LuxAB or Luc. Accordingly, ComX expression (and activity) may be detected and measured using a luciferase assay (Fontaine et al., 2010).

In some embodiments of the method of the present invention, the step of modulating the production of a ComX protein is performed by expressing a comX gene in said strain or increasing the expression of a comX gene in said strain. In a particular embodiment, the step of modulating the production of a ComX protein is performed by expressing a comX gene in said strain in some growth conditions, whereas said strain does not express the ComX protein outside of these growth conditions. In a particular embodiment, the step of modulating the production of a ComX protein is performed by increasing the expression of a comX gene in said strain in some growth conditions.

The comX gene may be an exogenous comX gene. As used herein an "exogenous comX gene" is understood to be a comX gene which is brought into the cytoplasm of the *Lactococcus* strain of step a), in order to be expressed. The exogenous comX gene may have the same sequence as the comX gene found in the genome of the *Lactococcus* strain of step a) or may have a different sequence from the comX gene found in the genome of the *Lactococcus* strain of step a). When different, the comX gene may be derived from a strain of a different species, a different subspecies or a different strain of *Lactococcus*.

The exogenous comX gene may be integrated within the genome of said *Lactococcus* strain.

Alternatively, the exogenous comX gene may be located within a vector. The vector may be selected from a plasmid, a viral vector (e.g. a phage), a cosmid, or a bacterial artificial chromosome.

Said plasmid may be transferred into said *Lactococcus* strain by conjugation, transformation or transduction. Said plasmid may be auto-replicative in the transformed *Lactococcus* strain or not.

The exogenous comX gene may be operably linked to transcription regulator(s). The exogenous comX gene may be located in a linear or circular polynucleotide.

Alternatively, in some embodiments of the method of the present invention, the comX gene is the endogenous comX gene of said *Lactococcus* strain. As used herein "the endogenous comX gene of said strain" is understood to be a comX gene that is naturally present in the genome of said strain.

In some embodiments, said comX gene is a *Lactococcus* comX gene. In an embodiment, said comX gene is a *Lactococcus lactis* comX gene. In a particular embodiment, said comX gene is a *Lactococcus lactis* subsp. *lactis* comX gene. In a particular embodiment, said comX gene is a *Lactococcus lactis* subsp. *cremoris* comX gene.

The comX gene may comprise or consist of a nucleotide sequence selected from the group consisting of:

SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19; SEQ ID NO:21;

a nucleotide sequence having at least 90%, at least 91%, at least 92%, at least 93%, at least 94%, at least 95%, at least 96%, at least 97%, at least 98%, or at least 99% identity to the nucleotide sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19; SEQ ID NO:21;

a variant of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21 encoding respectively a ComX protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 or SEQ ID NO:22; and a variant of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21 encoding respectively a functional ComX protein having at least 90% identity or at least 90% similarity to a ComX protein of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 or SEQ ID NO:22.

[SEQ ID NO: 1]
```
ATAACATATTACTTGGAAGAAGAGGATTTTGAAAATCTTTTTTCAGAAATGAAACCTATAGTTATGAA

ATTAATGAAACAAATTCGCATTAGAACATGGAAAATAGAGGATTATCTTCAAGAGGGGATGATTATTT

TACATCTTCTATTAGAAGAGCAGAACGATGGTCAAAAGCTGCATACAAAATTTAAGGTAAAGTATCAT

CAAAGATTAATAGATGAATTAAGACGAAGTTATGCAAAGAAACGAAGCCATGACCATTTTATAGGTTT

AGATGTTTATGAATGCTCAGACTGGATAAATTCAGGTGATACTAGTCCAGATAATGAAGTGGTCTTCA

ATCATTTGCTGGCAGAAGTATATGAAGGTTTGAGCGCACATTATCAAGACTTACTACTTCGACAAATG

CGAGGAGAAGAACTAACTCGCATGCAACGGTATCGCCTTCGTGAAAAAATAAAGGCCATCTTATTTTC

AGAAGACGAAGAGTGA
```

-continued

[SEQ ID NO: 2]
MTYYLEEEDFENLFSEMKPIVMKLMKQIRIRTWKIEDYLQEGMIILHLLLEEQNDGQKLHTKFKVKYH
QRLIDELRRSYAKKRSHDHFIGLDVYECSDWINSGDTSPDNEVVFNHLLAEVYEGLSAHYQDLLLRQM
RGEELTRMQRYRLREKIKAILFSEDEE

[SEQ ID NO: 3]
ATGACATATTACCTGGAAGAAAATGAATTCGAAGGTTTATTTTCTGGAATGAAACCAATCATCAGAAA
ATTGATGAAACAAATTCGAATCAAAGCATGGGACATAGAGGATTATTATCAAGAAGGAATGATTATT
TGCATCACCTTTTAGAAGAAAATCACCCATCCACTAATATTTATACAAAGTTCAAAGTAAAATATCAT
CAACATTTGATTGATGAACTACGCCATAGCTACGCCAAAAAACGGCTTCATGACCATTTTGTAGGTCT
GGACATTTATGAATGTTCGGACTGGATAGATGCAGGAGGAAGTACCCCTGAAAGCGAGCTTGTGTTCA
ATCATCTTTTAGCAGAAGTTTATGAAGGATTGAGCGCCCACTATCAGGAATTACTCGTGCGTCAAATG
AGAGGAGAAGAACTCACGCGAATGGAACGCTATCGGCTAAGAGAAAAAATCAAAAATATACTATTTTC
TCGAGATGATGATTAA

[SEQ ID NO: 4]
MTYYLEENEFEGLFSGMKPIIRKLMKQIRIKAWDIEDYYQEGMIILHHLLEENHPSTNIYTKFKVKYH
QHLIDELRHSYAKKRLHDHFVGLDIYECSDWIDAGGSTPESELVFNHLLAEVYEGLSAHYQELLVRQM
RGEELTRMERYRLREKIKNILFSRDDD

[SEQ ID NO: 5]
ATGGATGACATTCAAGAAAAATACGGTTTAGAATTCAACGAATTATTCTCTGAGATGCGGCCGATAAT
TTATAAATTGATGAAGCAATTGCACATCAACACATGGGATTACGATGATTACTTCCAAGAGGGAATGA
TTACACTACATGAATTGCTGCAGAAAATTACAAATTTAGATCATGTACATACGAAATTTAAAGTGGCT
TACCATCAGCACTTAATTGACGAAATTCGCCATATTAAAGCACGAAAAAGAGGTTTTGATCAGCTCCA
TCCGATCAATGTTTATGACTGCGCAGATTGGATTGGCTCAAACCTTGCTACACCTGAAAGCGAGATAG
TTTTCAACCATCTACTAGAAGAAGTTTATGATAAACTTTCAACACACTATAAAGAACTGTTGGTAAAG
CAAATGCATGGGAACATCTTACGAGAATGCAGAAGTATCGTTTAAAGGAAAAAATTAAAGCGATTTT
ATTTGATGAAGACTAA

[SEQ ID NO: 6]
MDDIQEKYGLEFNELFSEMRPIIYKLMKQLHINTWDYDDYFQEGMITLHELLQKITNLDHVHTKFKVA
YHQHLIDEIRHIKARKRGFDQLHPINVYDCADWIGSNLATPESEIVFNHLLEEVYDKLSTHYKELLVK
QMHGEHLTRMQKYRLKEKIKAILFDED

[SEQ ID NO: 7]
ATGGATAAAATTGAAACCATACTTAAAAGTATTGAACCGATTATTATGAACTGTCGGAAAAAAACTAA
AATTCCTTCCTGGGAATTAGACGACTATATGCAGGAAGGGATGATTATTGCTTTAGAGATGTACCATC
AACTCTTATTAGATCCACCAGATGATGACTTTAACTTCTATGTCTATTTCAAAGTCAGGTATTCTTGT
TTCTTAATTGATCACTATCGCAAAGCTATGGCAGTCAAGAGAAAATTCGACCAGCTTGACTATTGTGA
ACTTTCTGAGTCTGTTAATCTTTTTGATCACAAACAAAATGTGTCTGAAAACGTCATGTATAACTTGT
TGTGTCAAGAAATACACTTGGTTTTATCCCCGGAGGAGCTCAAGCTTTTTGAGGCACTTATTTGA

[SEQ ID NO: 8]
MDKIETILKSIEPIIMNCRKKTKIPSWELDDYMQEGMIIALEMYHQLLLDPPDDDFNFYVYFKVRYSC
FLIDHYRKAMAVKRKFDQLDYCELSESVNLFDHKQNVSENVMYNLLCQEIHLVLSPEELKLFEALI

[SEQ ID NO: 9]
ATGGATAGCATAGAAATGATGCTTCAAAATATTGAGCCAATTATTATGAATTGTAGTAAAACAACTAG
GATTCCATCTTGGGAGCTAGATGATTACATGCAGGAGGGATGATTATTGCACTGGAAATGTATCAAA
ATAGACATAACATCAATAACGGTAACGCGTTTAATTTCTATGTCTATTTTAAAGTCAGGTATTCCTGT

-continued

TACCTGATAGATAGTTTTAGAAAGGCTAACGCATATAAAAGAAAATTTGATCAACCATTATATTGTGA

AATATCTGAAGCCTTCAACCTTTATGATCACCACCAAAATGTTGCAGACAATGTCTGTTATCAGCTAT

TGCAAGTTGAAATTCTTGAGATATTAACACCAGATGAAGCTGATTTATTTATGACCTTGAAAATGGT

GGGAAAGTAGAGAGAAATAAAAAGTATAGATTAAAGAAAAAAATTATTGATTATCTTAAAGACATGTT

ATGA

[SEQ ID NO: 10]
MDSIEMMLQNIEPIIMNCSKTTRIPSWELDDYMQEGMIIALEMYQNRHNINNGNAFNFYVYFKVRYSC

YLIDSFRKANAYKRKFDQPLYCEISEAFNLYDHHQNVADNVCYQLLQVEILEILTPDEADLFMTLKNG

GKVERNKKYRLKKKIIDYLKDML

[SEQ ID NO: 11]
ATGGAGACTTTAGAAGCCATGCTCAAAAACATTGAACCTATTATTATGAATTGTCAAAAGATGGCAAA

AATACCTTCCTGGGATATTGACGATTATATGCAGGAGGGGAGGATCATTGCATTAGACTTGTATAATC

AGCTAGCAGAAAGAATGGAGACGGATGAGGTGAACTTTTACGTCTACTTCAAAGTCAGATATACCTGT

TTCTTGATTGATACTTACCGTAAGACAAATGCCTTTAAAAGAAAATTTGACCAACCGATTTACTTAGA

TGTATCCGAAGCATTTAATCTGTATGATCATAAGCAGAATGTCGCTGATAATGTCATGTATACTTTAT

TGCATCAGGAGATTCTAGACATCTTAACGCCTGTAGAAATTCAAACGCTAAACGCACTAAAAAGGGGA

GAAAAGGTCGACCGCAATAAAAAATTTAGGATTAAAAAGAAGATTATCAACTATATTAATCAGATTTT

CTAG

[SEQ ID NO: 12]
METLEAMLKNIEPIIMNCQKMAKIPSWDIDDYMQEGRIIALDLYNQLAERMETDEVNFYVYFKVRYTC

FLIDTYRKTNAFKRKFDQPIYLDVSEAFNLYDHKQNVADNVMYTLLHQEILDILTPVEIQTLNALKRG

EKVDRNKKFRIKKKIINYINQIF

[SEQ ID NO: 13]
ATGGAGCATAATTTAGATATGGAGCAGCTGGAAGAAATTTTTCATTCTGTCCAACATATTGTGTGGAA

GAACAGTCGTTTGATTCCGATAAATTTTTGGACGTTTGATGACTATCAGCAGGAAGGGCGCTTGGTAT

TATACGATTTGCTGGGAGATGGTGTGACGCAAAGGAACTTATTTTGCCATTTTAAGGTACGCTATAAG

CAGAGACTTATTGATATTAAAAGAAGGGAGCGGGCTTTTAAAAGGGGTTTTGATTGCGGGACTGGCTT

AGATATATACGAATATTCTGATGCTCTAAAGGGGAAAGCAGCCAGTCCAGAACATATCCTGATTTCTG

GAAGTTTACTTGAAGAAGTTTTTGAAAACTTAAATTTACGCTACCGACGGCTCCTCAAAAGTTACCTC

GCCGGCGATGAATTGCACCGTATGGAAAAGTATCGTTTGAAGGAAAAAATAACGAATATATTATATGA

ACAGCAGTGA

[SEQ ID NO 14]
MEHNLDMEQLEEIFHSVQHIVWKNSRLIPINFWTFDDYQQEGRLVLYDLLGDGVTQRNLFCHFKVRYK

QRLIDIKRRERAFKRGFDCGTGLDIYEYSDALKGKAASPEHILISGSLLEEVFENLNLRYRRLLKSYL

AGDELHRMEKYRLKEKITNILYEQQ

[SEQ ID NO: 15]
ATGGCAGAAAATAATTTAGATAAAGAACAGCTTGAAGAGTTATTCCATTCACTTCAACATATTGTTTG

GAAGAACAGTCATTTAATTAAAATAAATTTTTGGACAATGGATGATTATCAGCAAGAAGGGCGACTGG

TTTTATACCAGTTACTTGAAGATGGCGTGACACAGGAAAAACTATTTTGCCATTTTAAAGTGCGATAT

AAGCAACGGTTGATTGATATAAAAAGACGAGAAAGAGCATTTAAGCGGGGTTTTGATTGTGGGGCTGG

TTTAGATATATATGAGTATTCTGATGCCCTGAAAGGCAAAGCTACCAGTCCTGAATATAACTTAATTT

CAGTTACTTTACTTGAAGAGGTTCATCAAAGTTTGAGTTTGAGATACCGCAATTTATTGGAGAATCAT

CTGTCAGGAGTGGAGTTGCATCGAATGGAAAAATACCGTTTAAAGGAAAAAATCAAGAGAATACTCTA

TGAAGAAGAATGA

[SEQ ID NO: 16]
MAENNLDKEQLEELFHSLQHIVWKNSHLIKINFWTMDDYQQEGRLVLYQLLEDGVTQEKLFCHFKVRY

KORLIDIKRRERAFKRGFDCGAGLDIYEYSDALKGKATSPEYNLISVTLLEEVHQSLSLRYRNLLENH

LSGVELHRMEKYRLKEKIKRILYEEE

[SEQ ID NO: 17]
ATGGAGCATAATTTAGATATGGAGCAGCTGGAAGAGATATTTCATTCTGTTCAACATATTGTATGGAA

GAATAGTCGTTTGATTCCGATAAATTTTTGGACGATAGATGACTATCAGCAGGAAGGGCGTTTGGTAT

TATATGATTTACTTGAGGATGGTGTGACACAAAGAAAACTTTTTTGCCATTTTAAAGTACGTTATAAG

CAGAGACTTATTGATATTAAAAGAAGGGAGCGGGCTTTTAAAAGGGGTTTTGACTGTGGGACTGGGCT

AGATATTTACGAATATTCAGATGCTTTAAAAGGAAAAGTAGCCAGTCCAGAACATACTCTGATTTCTG

GCAGTTTGCTTGAAGAAGTTTTAGAAAACTTAAATTTACGCTACCGTGCTCTTCTTAAAAGTTACCTT

GCTGGTGATGAACTGCATCGAATGGAAAAACATCGTTTGAAAGAAAAAATAATAAAAATATTATATGA

TGAACAGTGA

[SEQ ID NO: 18]
MEHNLDMEQLEEIFHSVQHIVWKNSRLIPINFWTIDDYQQEGRLVLYDLLEDGVTQRKLFCHFKVRYK

QRLIDIKRRERAFKRGFDCGTGLDIYEYSDALKGKVASPEHTLISGSLLEEVLENLNLRYRALLKSYL

AGDELHRMEKHRLKEKIIKILYDEQ

[SEQ ID NO: 19]
TTGAAACCGATCGTTTCAAAATCTATGAGAACATTAAAAATCAATTTTTGGACTACAGAGGATTATCA

TCAAGAGGGTCTAATTACATTAAATGAAATATTAAATTCAGGATGTAAGGAGTCACAACTATACATTC

ACTTTAAAGTCAAATATCGACAAAAGCTAATAGACGTGATTAGAAATCACAGGCGCAAAAAAGAATC

TGGGATAATGCAGAGAGTATTGATGTTTACGAATCTGAAAATCAAATTAATTCCAGTAACTCAAACCC

CGAAGACATAATAGTCTATGACAGTCTTGTAAAGGAAGTAATAACAAAATTAACACCTTCATACCGGA

AACTACTGAAACGACATCTAAGAGGTGAGGATGTGACAAGGATGGAAAAATACAGACTGAAGGAACGA

ATCAAACAAATTTTATTTGATGGTGATTGA

[SEQ ID NO: 20]
MKPIVSKSMRTLKINFWTTEDYHQEGLITLNEILNSGCKESQLYIHFKVKYRQKLIDVIRKSQAQKRI

WDNAESIDVYESENQINSSNSNPEDIIVYDSLVKEVITKLTPSYRKLLKRHLRGEDVTRMEKYRLKER

IKQILFDGD

[SEQ ID NO: 21]
ATGGATAAGATTGAAACCATACTTAAAAATATTGAACCGATTATCATGAACTGTCGAAAAAAAACTAA

CATCCCTTCCTGGCAATTAGACGACTATCTCCAGGAAGGCATGATTATTGCTCTAGAGATGTATCATC

AACTTTTATTAGACCCACCAGATGATGACTTTAACTTCTATGTTTATTTCAAAGTGAGATATTCTTGT

TTCTTGATTGATCAGTATCGGAGAAACATGGCTGTCAAAAGAAAATTCGACCAGATTGACTATTGTGA

ACTATCTGAGGCGTTTTATCTTTTTGATCAAAATCAAGATGTCTCTGAAAACGTCATGTATAATTTGT

TATGTCAAGAAATACACTTGCTTCTATCTCCTGAAGAACGAGAGCTTTTTGAGGCACTTAAAAATGGA

CAGAAGATTGACCGTAATCAAAAGTTTCGTATCAAGAAGAAAATTATTGAATATATTAAGAGGTTTTG

GTGA

[SEQ ID NO: 22]
MDKIETILKNIEPIIMNCRKKTNIPSWQLDDYLQEGMIIALEMYHQLLLDPPDDDFNFYVYFKVRYSC

FLIDQYRRNMAVKRKFDQIDYCELSEAFYLFDQNQDVSENVMYNLLCQEIHLLLSPEERELFEALKNG

QKIDRNQKFRIKKKIIEYIKREW

In some embodiments, said comX gene has the nucleotide sequence of SEQ ID NO:1 or SEQ ID NO:3 or SEQ ID NO:5 or has at least 90%, at least 91%, at least 92%, at least 93%, at least 94%, at least 95%, at least 96%, at least 97%, at least 98%, or at least 99% identity to the nucleotide sequence of SEQ ID NO:1 or SEQ ID NO:3 or SEQ ID NO:5 or is a variant of SEQ ID NO:1 or SEQ ID NO:3 or SEQ ID NO:5 encoding respectively the ComX protein of SEQ ID NO:2, SEQ ID NO:4 or SEQ ID NO:6 or is a variant of SEQ ID NO:1 or SEQ ID NO:3 or SEQ ID NO:5 encoding respectively a functional ComX protein having at least 90% identity or at least 90% similarity to a ComX protein of SEQ ID NO:2, SEQ ID NO:4 or SEQ ID NO:6. In a particular embodiment, said comX gene is used when the Lactococcus strain in step a) is a Lactococcus lactis strain.

In a particular embodiment, when the strain of step a) is a Lactococcus lactis subsp. lactis strain, the comX gene comprises the nucleotide sequence of SEQ ID NO:1, any sequence having at least 90%, at least 91%, at least 92%, at least 93%, at least 94%, at least 95%, at least 96%, at least 97%, at least 98%, or at least 99% identity to SEQ ID NO:1, a variant of SEQ ID NO:1 encoding the ComX protein of SEQ ID NO:2 or a variant of SEQ ID NO:1 encoding a functional ComX protein having at least 90% identity or at least 90% similarity to a ComX protein of SEQ ID NO:2.

In a particular embodiment, when the strain of step a) is a Lactococcus lactis subsp. cremoris strain, the comX gene comprises the nucleotide sequence of SEQ ID NO:3 or SEQ ID NO:5, any sequence having at least 90%, at least 91%, at least 92%, at least 93%, at least 94%, at least 95%, at least 96%, at least 97%, at least 98%, or at least 99% identity to SEQ ID NO:3 or SEQ ID NO:5 or a variant of SEQ ID NO:3 or SEQ ID NO:5 encoding respectively the ComX protein of SEQ ID NO:4 or SEQ ID NO:6 or a variant of SEQ ID NO:3 or SEQ ID NO:5 encoding respectively a functional ComX protein having at least 90% identity or at least 90% similarity to a ComX protein of SEQ ID NO:4 or SEQ ID NO:6.

In some embodiments, said comX gene has the nucleotide sequence of SEQ ID NO:7 or has at least 90%, at least 91%, at least 92%, at least 93%, at least 94%, at least 95%, at least 96%, at least 97%, at least 98%, or at least 99% identity to the nucleotide sequence of SEQ ID NO:7 or is a variant of SEQ ID NO:7 encoding the ComX protein of SEQ ID NO:8, or is a variant of SEQ ID NO:7 encoding a functional ComX protein having at least 90% identity or at least 90% similarity to a ComX protein of SEQ ID NO:8. In a particular embodiment, said comX gene is used when the Lactococcus strain in step a) is a Lactococcus raffinolactis strain.

In some embodiments, said comX gene has the nucleotide sequence of SEQ ID NO:9 or has at least 90%, at least 91%, at least 92%, at least 93%, at least 94%, at least 95%, at least 96%, at least 97%, at least 98%, or at least 99% identity to the nucleotide sequence of SEQ ID NO:9 or is a variant of SEQ ID NO:9 encoding the ComX protein of SEQ ID NO:10, or is a variant of SEQ ID NO:9 encoding a functional ComX protein having at least 90% identity or at least 90% similarity to a ComX protein of SEQ ID NO:10. In a particular embodiment, said comX gene is used when the Lactococcus strain in step a) is a Lactococcus plantarum strain.

In some embodiments, said comX gene has the nucleotide sequence of SEQ ID NO:11 or has at least 90%, at least 91%, at least 92%, at least 93%, at least 94%, at least 95%, at least 96%, at least 97%, at least 98%, or at least 99% identity to the nucleotide sequence of SEQ ID NO:11 or is a variant of SEQ ID NO:11 encoding the ComX protein of SEQ ID NO:12, or is a variant of SEQ ID NO:11 encoding a functional ComX protein having at least 90% identity or at least 90% similarity to a ComX protein of SEQ ID NO:12. In a particular embodiment, said comX gene is used when the Lactococcus strain in step a) is a Lactococcus piscium strain.

In a particular embodiment, said comX gene has the nucleotide sequence of SEQ ID NO:13 or SEQ ID NO:15 or SEQ ID NO:17, any sequence having at least 90%, at least 91%, at least 92%, at least 93%, at least 94%, at least 95%, at least 96%, at least 97%, at least 98%, or at least 99% identity to SEQ ID NO:13 or SEQ ID NO:15 or SEQ ID NO:17 or a variant of SEQ ID NO:13 or SEQ ID NO:15 or SEQ ID NO:17 encoding respectively the ComX protein of SEQ ID NO:14 or SEQ ID NO:16 or SEQ ID NO:18 or a variant of SEQ ID NO:13 or SEQ ID NO:15 or SEQ ID NO:17 encoding respectively a functional ComX protein having at least 90% identity or at least 90% similarity to a ComX protein of SEQ ID NO:14 or SEQ ID NO:16 or SEQ ID NO:18. In a particular embodiment, said comX gene is used when the Lactococcus strain in step a) is a Lactococcus garvieae strain.

In some embodiments, said comX gene has the nucleotide sequence of SEQ ID NO:19 or has at least 90%, at least 91%, at least 92%, at least 93%, at least 94%, at least 95%, at least 96%, at least 97%, at least 98%, or at least 99% identity to the nucleotide sequence of SEQ ID NO:19 or is a variant of SEQ ID NO:19 encoding the ComX protein of SEQ ID NO:20, or is a variant of SEQ ID NO:19 encoding a functional ComX protein having at least 90% identity or at least 90% similarity to a ComX protein of SEQ ID NO:20. In a particular embodiment, said comX gene is used when the Lactococcus strain in step a) is a Lactococcus fujiensis strain.

In some embodiments, said comX gene has the nucleotide sequence of SEQ ID NO:21 or has at least 90%, at least 91%, at least 92%, at least 93%, at least 94%, at least 95%, at least 96%, at least 97%, at least 98%, or at least 99% identity to the nucleotide sequence of SEQ ID NO:21 or is a variant of SEQ ID NO:21 encoding the ComX protein of SEQ ID NO:22, or is a variant of SEQ ID NO:21 encoding a functional ComX protein having at least 90% identity or at least 90% similarity to a ComX protein of SEQ ID NO:22. In a particular embodiment, said comX gene is used when the Lactococcus strain in step a) is a Lactococcus chungangensis strain.

By way of example and for the avoidance of doubt, in particular embodiments, where a comX gene is specified as having a particular nucleotide sequence, it is understood that the comX gene comprises said nucleotide sequence. In particular other embodiments, where a comX gene is specified as having a particular nucleotide sequence, it is understood that the comX gene consists of said nucleotide sequence.

In some embodiments, variants as defined herein of comX genes are selected from the list of DNA sequences disclosed in Table 1 below:

TABLE 1

| Strain | Accession number | Position of comX, from start to stop |
| --- | --- | --- |
| Lactococcus lactis Al06 | CP009472.1 | From 2260881 to 2261372 (reverse) |
| Lactococcus lactis Bpl1 | JRFX01000055.1 | From 34668 to 35159 (forward) |

TABLE 1-continued

| Strain | Accession number | Position of comX, from start to stop |
|---|---|---|
| *Lactococcus lactis* Ll1596 | LDEK01000015.1 | From 33401 to 33892 (forward) |
| *Lactococcus lactis* subsp. *cremoris* A17 | JQIC01000009.1 | From 6445 to 6936 (reverse) |
| *Lactococcus lactis* subsp. *cremoris* A76 | CP003132.1 | From 2293232 to 2293723 (reverse) |
| *Lactococcus lactis* subsp. *cremoris* AM2 | LITE01000081.1 | From 9954 to 10444 (forward) |
| *Lactococcus lactis* subsp. *cremoris* B40 | LITC01000320.1 | From 10186 to 10677 (forward) |
| *Lactococcus lactis* subsp. *cremoris* DPC6856 | LAVW01000168.1 | From 445 to 936 (reverse) |
| *Lactococcus lactis* subsp. *cremoris* GE214 | AZSI01000020.1 | From 186 to 677 (reverse) |
| *Lactococcus lactis* subsp. *cremoris* HP | JAUH01000192.1 | From 40 to 531 (reverse) |
| *Lactococcus lactis* subsp. *cremoris* IBB477 | JMMZ01000035.1 | From 92323 to 92814 (reverse) |
| *Lactococcus lactis* subsp. *cremoris* KW10 | LIYF01000023.1 | From 40421 to 40912 (forward) |
| *Lactococcus lactis* subsp. *cremoris* KW2 | CP004884.1 | From 2276371 to 2276862 (reverse) |
| *Lactococcus lactis* subsp. *cremoris* LMG6897 | LISZ01000238.1 | From 10034 to 10525 (forward) |
| *Lactococcus lactis* subsp. *cremoris* Mast36 | JZUI01000076.1 | From 310 to 801 (reverse) |
| *Lactococcus lactis* subsp. *cremoris* MG1363 | AM406671.1 | From 2376782 to 2377273 (reverse) |
| *Lactococcus lactis* subsp. *cremoris* NBRC 100676 | BCVK01000073.1 | From 9879 to 10370 (forward) |
| *Lactococcus lactis* subsp. *cremoris* NZ9000 | CP002094.1 | From 2377598 to 2378089 (reverse) |
| *Lactococcus lactis* subsp. *cremoris* SK11 | CP000425.1 | From 2283008 to 2283498 (reverse) |
| *Lactococcus lactis* subsp. *cremoris* TIFN1 | ASXF01000005.1 | From 5621 to 6112 (forward) |
| *Lactococcus lactis* subsp. *cremoris* TIFN3 | ATBE01000400.1 | From 431 to 922 (reverse) |
| *Lactococcus lactis* subsp. *cremoris* TIFN5 | ATBC01000090.1 | From 315 to 809 (reverse) |
| *Lactococcus lactis* subsp. *cremoris* TIFN6 | ATBB01000278.1 | From 265 to 756 (forward) |
| *Lactococcus lactis* subsp. *cremoris* TIFN7 | ATBA01000081.1 | From 5620 to 6111 (forward) |
| *Lactococcus lactis* subsp. *cremoris* UC509.9 | CP003157.1 | From 2107522 to 2108013 (reverse) |
| *Lactococcus lactis* subsp. *cremoris* V4 | LIYG01000005.1 | From 8625 to 9116 (forward) |
| *Lactococcus lactis* subsp. *hordniae* NBRC 100931 | BCVL01000030.1 | From 70 to 561 (reverse) |
| *Lactococcus lactis* subsp. *lactis* 1AA59 | AZQT01000035.1 | From 118 to 609 (reverse) |
| *Lactococcus lactis* subsp. *lactis* 511 | JNLP01000001.1 | From 1703029 to 1703520 (reverse) |
| *Lactococcus lactis* subsp. *lactis* A12 | LT599049.1 | From 2415707 to 2416198 (reverse) |
| *Lactococcus lactis* subsp. *lactis* ATCC 19435 | LKLC01000004.1 | From 32310 to 32801 (forward) |
| *Lactococcus lactis* subsp. *lactis* bv. *diacetylactis* DRA4 | LIWD01000119.1 | From 147 to 638 (reverse) |
| *Lactococcus lactis* subsp. *lactis* CV56 | CP002365.1 | From 2213300 to 2213791 (reverse) |
| *Lactococcus lactis* subsp. *lactis* DPC6853 | LAVD01000101.1 | From 544 to 1035 (reverse) |
| *Lactococcus lactis* subsp. *lactis* E34 | LKLD01000014.1 | From 197 to 688 (reverse) |
| *Lactococcus lactis* subsp. *lactis* Il1403 | AE005176.1 | From 2223528 to 2224019 (reverse) |
| *Lactococcus lactis* subsp. *lactis* IO-1 DNA | AP012281.1 | From 2287126 to 2287617 (reverse) |
| *Lactococcus lactis* subsp. *lactis* JCM 7638 | BBAP01000017.1 | From 34164 to 34656 (forward) |
| *Lactococcus lactis* subsp. *lactis* K231 | LKLE01000041.1 | From 32159 to 32650 (forward) |
| *Lactococcus lactis* subsp. *lactis* K337 | LKLF01000041.1 | From 34909 to 35400 (forward) |
| *Lactococcus lactis* subsp. *lactis* KF134 | LKLJ01000010.1 | From 34939 to 35430 (forward) |
| *Lactococcus lactis* subsp. *lactis* KF147 | CP001834.1 | From 2446402 to 2446893 (reverse) |
| *Lactococcus lactis* subsp. *lactis* KF201 | LKLM01000024.1 | From 28747 to 29238 (forward) |
| *Lactococcus lactis* subsp. *lactis* KF24 | LKLH01000011.1 | From 34116 to 34607 (forward) |
| *Lactococcus lactis* subsp. *lactis* KF282 | LKLN01000033.1 | From 170 to 661 (reverse) |
| *Lactococcus lactis* subsp. *lactis* KLDS 4.0325 | CP006766.1 | From 2407603 to 2408094 (reverse) |
| *Lactococcus lactis* subsp. *lactis* LMG 7760 | JQCM01000018.1 | From 37736 to 38227 (forward) |
| *Lactococcus lactis* subsp. *lactis* LMG8526 | LKLQ01000046.1 | From 38499 to 38993 (forward) |
| *Lactococcus lactis* subsp. *lactis* NCDO 2118 | CP009054.1 | From 2402923 to 2403414 (reverse) |
| *Lactococcus lactis* subsp. *lactis* S0 | CP010050.1 | From 2359456 to 2359947 (reverse) |
| *Lactococcus lactis* subsp. *lactis* UC317 | LKLY01000004.1 | From 36130 to 36621 (forward) |
| *Lactococcus lactis* WG2 | LXWJ01000007.1 | From 37921 to 38412 (forward) |
| *Lactococcus raffinolactis* NBRC 100932 | BCVN01000102.1 | From 139 to 617 (forward) |
| *Lactococcus piscium* CNCM I-4031 | FLZT01000001.1 | From 149 to 628 (forward) |
| *Lactococcus piscium* MKFS47 | LN774769.1 | From 1708720 to 1709199 (forward) |
| *Lactococcus garvieae* 122061 | AP017373.1 | From 1356405 to 1356890 (forward) |
| *Lactococcus garvieae* 8831 | AFCD01000005.1 | From 510 to 995 (forward) |
| *Lactococcus garvieae* Lg-ilsanpaik-gs201105 | JPUJ01000002.1 | From 180817 to 181302 (reverse) |
| *Lactococcus garvieae* LG9 | AGQY01000137.1 | From 5631 to 6116 (reverse) |
| *Lactococcus garvieae* M79 | FOTJ01000023.1 | From 3224 to 3709 (forward) |
| *Lactococcus garvieae* NBRC 100934 | BBJW01000010.1 | From 105946 to 106431 (reverse) |
| *Lactococcus garvieae* PAQ102015-99 | LXWL01000009.1 | From 238437 to 238922 (reverse) |
| *Lactococcus garvieae* TB25 | AGQX01000090.1 | From 28088 to 28573 (reverse) |
| *Lactococcus garvieae* TRF1 | AVFE01000015.1 | From 42141 to 42626 (reverse) |

As used herein a comX gene is understood to be a gene that encodes a functional ComX protein in the strain where it is expressed. By "functional ComX protein" it is meant a protein which induces or is able to induce the expression of genes regulated by the Corn-box, and at least one of the late competence genes selected from comEA, comFA, comGA, dprA, coiA, ssbA, radA, radC, recA, and recX.

The ComX protein may have the amino acid sequence of SEQ ID NO:2, SEQ ID NO: 4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 or SEQ ID NO:22, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 or SEQ ID NO:22, or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20 or SEQ ID NO:22.

In some embodiments, the ComX protein may have the amino acid sequence of SEQ ID NO:2, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:2 or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:2. In a particular embodiment, said ComX protein is used when the *Lactococcus* strain in step a) is a *Lactococcus lactis* subsp. *lactis* strain.

In some embodiments, the ComX protein may have the amino acid sequence of SEQ ID NO:4 or SEQ ID NO:6, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:4 or SEQ ID NO:6 or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:4 or SEQ ID NO:6. In a particular embodiment, said ComX protein is used when the *Lactococcus* strain in step a) is a *Lactococcus lactis* subsp. *cremoris* strain.

In some embodiments, the ComX protein may have the amino acid sequence of SEQ ID NO:8, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:8 or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:8. In a particular embodiment, said ComX protein is used when the *Lactococcus* strain in step a) is a *Lactococcus raffinolactis* strain.

In some embodiments, the ComX protein may have the amino acid sequence of SEQ ID NO:10, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:10 or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:10. In a particular embodiment, said ComX protein is used when the *Lactococcus* strain in step a) is a *Lactococcus plantarum* strain.

In some embodiments, the ComX protein may have the amino acid sequence of SEQ ID NO:12, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:12 or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:12. In a particular embodiment, said ComX protein is used when the *Lactococcus* strain in step a) is a *Lactococcus piscium* strain.

In some embodiments, the ComX protein may have the amino acid sequence of SEQ ID NO:14, SEQ ID NO:16 or SEQ ID NO:18, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:14, SEQ ID NO:16 or SEQ ID NO:18 or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:14, SEQ ID NO:16 or SEQ ID NO:18. In a particular embodiment, said ComX protein is used when the *Lactococcus* strain in step a) is a *Lactococcus garvieae* strain.

In some embodiments, the ComX protein may have the amino acid sequence of SEQ ID NO:20, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:20 or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:20. In a particular embodiment, said ComX protein is used when the *Lactococcus* strain in step a) is a *Lactococcus fujiensis* strain.

In some embodiments, the ComX protein may have the amino acid sequence of SEQ ID NO:22, or an amino acid sequence having at least 90%, at least 91%, at least 92%, at least 93%, at least 94%, at least 95%, at least 96%, at least 97%, at least 98%, or at least 99% identity to the amino acid sequence of SEQ ID NO:22 or an amino acid sequence having at least 90%, at least 91%, at least 92%, at least 93%, at least 94%, at least 95%, at least 96%, at least 97%, at least 98%, or at least 99% similarity to the amino acid sequence of SEQ ID NO:22. In a particular embodiment, said ComX protein is used when the *Lactococcus* strain in step a) is a *Lactococcus chungangensis* strain.

According to the invention, when a ComX protein is defined by its amino acid sequence having a percentage of identity or percentage of similarity to a specific SEQ ID, said ComX protein is a functional ComX protein as defined herein.

By way of example and for the avoidance of doubt, in particular embodiments, where a ComX protein is specified as having a particular amino acid sequence, it is understood that the ComX protein comprises said amino acid sequence. In particular other embodiments, where a ComX protein is specified as having a particular amino acid sequence, it is understood that the ComX protein consists of said amino acid sequence.

In some embodiments, ComX proteins having percentage of identity or percentage of similarity as defined herein are selected from the list of protein sequences derived, after translation, from the list of DNA sequences disclosed in Table 1 above.

Preferably, reference to a sequence which has a percentage identity or similarity to any one of the SEQ ID NOs detailed herein refers to a sequence which has the stated percent identity or similarity with the SEQ ID NO referred to, over the entire length of the two sequences. Percentage (%) sequence identity is defined as the percentage of amino acids or nucleotides in a candidate sequence that are identical to the amino acids or nucleotides in a reference sequence, after aligning the sequences and introducing gaps, if necessary, to achieve the maximum percent sequence identity. Percentage (%) sequence similarity is defined as percentage of amino acids in a candidate sequence that are similar to the amino acids in a reference sequence, after aligning the sequences and introducing gaps, if necessary, to achieve the maximum percent sequence similarity. Similarity between amino acids is based on established amino acid substitution matrices such as the PAM series (Point Accepted Mutation; e.g. PAM30, PAM70, and PAM250) or the BLOSUM series (BLOck SUbstitution Matrix; e.g. BLOSUM45, BLOSUM50, BLOSUM62, BLOSUM80, and BLOSUM90). Alignment for purposes of determining percent sequence identity or similarity can be achieved in various ways that are within the skill in the art, for instance, using publicly available computer software such as CLUSTALW, CLUSTALX, CLUSTAL Omega, BLAST, BLAST-2, ALIGN, ALIGN-2 or Megalign (DNASTAR) software. In a particular embodiment, similarity between amino acids is determined using the BLASTp software with the BLOSUM62 matrix. Appropriate parameters for measuring alignment, including any algorithms needed to achieve maximal alignment over the full-length of the sequences being compared, or gap penalties to be introduced, can be determined by known methods.

In a particular embodiment, when the modulation in step b) results from an exogenous comX gene, said exogenous comX gene is (obtained) from a strain of the same species, in particular of the same subspecies, as the strain provided in step a). In any case, the exogenous comX gene needs to be functional, in particular needs to encode a functional ComX protein, as defined herein in the strain provided in step a).

Exogenous DNA Polynucleotide

The method of the present invention comprises the step of contacting the strain of step b) with an exogenous DNA polynucleotide in a medium and incubating the resulting mixture for integration of the exogenous DNA into the genome of said strain [step c].

As used herein the term "exogenous DNA polynucleotide" refers to a DNA polynucleotide that is brought into the cytoplasm of said strain, in order to be integrated into the genome of said strain (target sequence).

In a particular embodiment, the method comprises carrying out step (b) [ComX modulation] and then carrying out step (c) [contact with the exogenous DNA polynucleotide] [i.e., that step (c) is carried out on a strain obtained following step (b)]. Thus, the method comprising the steps of:

(a) providing a strain of the *Lactococcus* genus, wherein said strain is transformable through natural competence;
(b) modulating the production of a ComX protein in said strain;
(c) contacting said strain obtained in step (b) with an exogenous DNA polynucleotide in a medium and incubating the resulting mixture for integration of the exogenous DNA polynucleotide into the genome of said strain; and
(d) selecting a strain which has integrated the exogenous DNA polynucleotide into its genome.

In another embodiment, the method comprises carrying out simultaneously step (b) [ComX modulation] and step (c) [contact with the exogenous DNA polynucleotide]. This option is appropriate when the ComX modulation is the result of the expression of the endogenous comX gene or of the increase of the expression of the endogenous comX gene of said strain. Thus, the method comprising the steps of:

(a) providing a strain of the *Lactococcus* genus, wherein said strain is transformable through natural competence;
(b) modulating the production of a ComX protein in said strain;
(c) contacting said strain with an exogenous DNA polynucleotide in a medium and incubating the resulting mixture for integration of the exogenous DNA polynucleotide into the genome of said strain; and
(d) selecting a strain which has integrated the exogenous DNA polynucleotide into its genome;

wherein step (b) and step (c) are carried out simultaneously.

In a particular embodiment, the sequence of the exogenous DNA polynucleotide used in step c) share some similarities or identities with the genome of the *Lactococcus* strain to be transformed (of step a). In a particular embodiment, the exogenous DNA polynucleotide used in step c) is designed such that its 5' part and its 3' part are identical or highly similar to parts of the genome of the *Lactococcus* strain to be transformed (of step a), while its central part can be different from the genome of the *Lactococcus* strain to be transformed (of step a). The high similarity of the arms with the regions surrounding the target sequence can be determined by the person skilled in the art using common general knowledge, in particular by reference to homologous recombination.

Thus, to replace a target sequence by a mutated sequence or a truncated sequence or a supplementary sequence in the genome of the *Lactococcus* strain to be transformed (of step a), the exogenous DNA polynucleotide used in step c) is designed such that:

its 5' part is identical or highly similar to the region of the genome of the *Lactococcus* strain to be transformed which is on one side of the target sequence;
its central part contains the replacing sequence (i.e., the mutated sequence or the truncated sequence or the supplementary sequence); and
its 3' part is identical or highly similar to the region of the genome of the *Lactococcus* strain to be transformed which is on the other side of the target sequence.

The 5' part and 3' part are long enough to ensure efficient recombination. In a particular embodiment, each of the 5' part and 3' part is from 0.5 to 5 kb in length. The size of the arms can be determined by the person skilled in the art using common general knowledge, in particular by reference to homologous recombination.

In a particular embodiment, the exogenous DNA polynucleotide used in step c) is (obtained) from a strain of the *Lactococcus* genus.

In a particular embodiment, said exogenous DNA polynucleotide used in step (c) is (obtained) from a strain of the same species, in particular of the same subspecies, as the strain provided in step (a).

In a particular embodiment, the exogenous DNA polynucleotide used in step c) is from a strain of the *Lactococcus lactis* species. In a particular embodiment, the exogenous DNA polynucleotide used in step c) is from a strain of the same *Lactococcus lactis* subspecies as the strain provided in step a). In a particular embodiment, the exogenous DNA polynucleotide used in step c) is from a strain of a *Lactococcus lactis* subspecies which is different from the strain provided in step a).

In a particular embodiment, the exogenous DNA polynucleotide used in step c) is from a strain of the *Lactococcus raffinolactis* species The exogenous DNA polynucleotide may encode part of a gene sequence, a gene sequence, or a plurality of gene sequences. The gene sequence may be operably linked to transcription regulator(s). In a particular embodiment, the exogenous DNA polynucleotide is linear. The exogenous DNA polynucleotide may be designed to facilitate its incorporation within the genome of the *L. lactis* strain by homologous recombination (e.g. the exogenous DNA polynucleotide may comprise one or more recombination arms). The exogenous DNA polynucleotide may be a single stranded linear DNA.

The exogenous DNA polynucleotide, when incorporated into the genome of said *Lactococcus* strain leads to genetic modification of the strain such as gene replacement (to add or to remove a mutation), gene addition (to add a new gene or to duplicate an existing gene), gene deletion (to remove part or the totality of a gene), modification of non-coding region (to modulate expression of a gene). Typically, the exogenous DNA polynucleotide, when incorporated into the genome of said *Lactococcus* strain confers an interesting or useful phenotype, e.g. modified kinetic of acidification, improved resistance to bacteriophage, modified capability to grow in milk, modified texturing properties, improved safety of the strain. For example, improved bacteriophage resistance could be achieved by incorporating genes coding for a restriction/modification system into the strain genome or by introducing a mutation or a deletion into the pip gene.

As an example, growth of a *L. lactis* strain in milk could be improved by inserting into the chromosome the prtP and prtM genes that allow casein hydrolysis and better nitrogen nutrition; alternatively, these genes could be inactivated to reduced milk proteolysis in cheese. hisDC and tyrDC are genes known to be responsible for biogenic amine production (histamine and tyramine, respectively) in a diversity of lactic acid bacteria; disruption or mutation of these genes could help to prevent safety issues related to cheese consumption.

In a particular embodiment, the exogenous DNA polynucleotide has a minimal size selected from the group consisting of 100 bp, 200 bp, 500 bp, 1 kb, 2 kb and 5 kb, and a maximal size selected from the group consisting of 500 bp, 1 kb, 2 kb, 5 kb, 10 kb, 20 kb and 50 kb. In a particular embodiment, the size of the exogenous DNA polynucleotide may be between 100 bp and 50 kb, more preferably between 500 bp to 20 kb, even more preferably between 1 kb to 10 kb.

The concentration of exogenous DNA polynucleotide in the medium of step (c) may be between 0.5 mg/L and 1 g/L, preferably between 1 mg/L and 500 mg/L, more preferably between 5 mg/L and 100 mg/L, even more preferably between 10 mg/L and 50 mg/L of medium.

Selection of Transformed Strains

The method of the present invention comprises the step of selecting a strain which has integrated the exogenous DNA polynucleotide into its genome [step d)].

If needed, selection is carried out on some cells of colonies that have been previously obtained by multiplying, in the appropriate medium, cells obtained at the end of step c) (or at the end of the simultaneous steps b) and c), when appropriate).

Various methods for the selection of transformed bacteria are well known in the art (see, e.g. Sambrook et al.) and may be routinely applied by the person skilled in the art, such as PCR, DNA sequencing.

For example, when the exogenous DNA polynucleotide used in step c) provides a particular phenotype that the *Lactococcus* strain of step a) does not display (either a new phenotype or restoring a lost phenotype), it is possible to select strains which have integrated the exogenous DNA polynucleotide into their genome by selecting strains expressing the phenotype. This is the case for a strain having integrated in its genome an exogenous DNA polynucleotide mutated for the pip gene (that provides resistance to some bacteriophages).

For example, when the exogenous DNA polynucleotide used in step c) leads once integrated to a loss of a phenotype initially displayed by the *Lactococcus* strain of step a), it is possible to select strains which have integrated the exogenous DNA polynucleotide into their genome by selecting strains which do not display the phenotype any more. This is the case for an exogenous DNA polynucleotide bearing a mutated hisDC or tyrDC gene, which suppresses or decreases the production of histamine or tyramine, respectively.

As a particular example, the exogenous DNA polynucleotide may bear an antibiotic resistance gene. Accordingly, a *Lactococcus* strain which has integrated the exogenous DNA polynucleotide into its genome may be selected by plating onto a medium comprising said antibiotic. Only strains that express the appropriate antibiotic resistance gene, as a result of a successful transformation with the exogenous DNA polynucleotide, will multiply.

Growth Conditions

As described in Example 3, a positive effect on natural competence induction in *L. lactis* strains was observed when cells were pre-cultured in a complex medium before transferring the cells to a chemically defined medium (FIG. 3).

Accordingly, in some embodiments the medium of step (c) is a chemically defined medium. As used herein, the term "chemically defined medium" (CDM) refers to a medium for which the exact chemical composition is known. Preferably, the CDM may have the composition of the CDM set out in Sissler et al. (1999, Proc Natl Acad Sci USA 96:8985-8990). Thus, in an embodiment, the chemically defined medium (CDM) comprises 0.5 g/L $NH_4Cl$, 9.0 g/L $KH_2PO_4$, 7.5 g/L $K_2HPO_4$, 0.2 g/L $MgCl_2$, 5 mg/L $FeCl_2$, 50 mg/L $CaCl_2$, 5 mg/L $ZnSO_4$, 2.5 mg/L $CoCl_2$, 0.05 g/L tyrosine, 0.1 g/L asparagine, 0.1 g/L cysteine, 0.1 g/L glutamine, 0.1 g/L isoleucine, 0.1 g/L leucine, 0.1 g/L methionine, 0.1 g/L tryptophan, 0.1 g/L valine, 0.1 g/L histidine, 0.2 g/L arginine, 0.2 g/L glycine, 0.2 g/L lysine, 0.2 g/L phenylalanine, 0.2 g/L threonine, 0.3 g/L alanine, 0.3 g/L proline, 0.3 g/L serine, 10 mg/L paraaminobenzoic acid, 10 mg/L biotin, 1 mg/L folic acid, 1 mg/L nicotinic acid, 1 mg/L panthotenic acid, 1 mg/L riboflavin, 1 mg/L thiamine, 2 mg/L pyridoxine, 1 mg/L cyanocobalamin, 5 mg/L orotic acid, 5 mg/L 2-deoxythymidine, 5 mg/L inosine, 2.5 mg/L dl-6,8-thioctic acid, 5 mg/L pyridoxamine, 10 mg/L adenine, 10 mg/L guanine, 10 mg/L uracil, 10 mg/L xanthine, and 5 g/L glucose.

In some embodiments, prior to step (c) said strain is incubated in a pre-culture medium, preferably wherein the pre-culture medium is a complex medium, more preferably wherein the pre-culture medium is M17G (i.e., the M17 medium supplemented with glucose) or THBG (i.e., the THB medium supplemented with glucose).

The complex medium may be Todd Hewitt broth (THB) (Todd and Hewitt, 1932; Updyke and Nickle, 1954) or M17 broth (Terzaghi and Sandine, 1975). THB may comprise 500 g/L beef heart infusion, 20 g/L peptic digest of animal tissue, 2 g/L dextrose, 2 g/L sodium chloride, 0.4 g/L sodium phosphate, 2.5 g/L sodium carbonate. M17 broth may comprise: 0.5 g/L ascorbic acid, 5 g/L lactose, 0.25 g/L magnesium sulfate, 5 g/L meat extract, 2.5 g/L meat peptone (peptic), 19 g/L sodium glycerophosphate, 5 g/L soya peptone (papainic), 2.5 g/L tryptone, 2.5 g/L yeast extract.

Method for Identifying Strains Transformable by Natural Competence

In another aspect, the present invention relates to a method for identifying a strain of the *Lactococcus* genus which is transformable through natural competence. Said method comprises the following steps:
(a) providing a strain of the *Lactococcus* genus;
(b) transforming said strain with a plasmid expressing a comX gene having at least 90% identity, preferably having 100% identity, to the endogenous comX gene of said strain;
(c) contacting said strain obtained in step (b) with an exogenous marker DNA polynucleotide in a medium and incubating the resulting mixture for integration of the exogenous DNA polynucleotide into the genome of said strain; and
(d) determining the rate of recombination events;
wherein a rate of at least $1 \times 10^{-6}$ transformants per µg of DNA is indicative of a strain which is transformable through natural competence.

The term "rate of recombination events" may be used interchangeably with the term "transformation rate". The rate of recombination events is calculated by determining the ratio of the number of cells having integrated the exogenous marker DNA polynucleotide over the total number of viable cells. A rate of at least $10^{-6}$ was selected as a threshold, based on the observation that the level of spontaneous mutation in lactococci is less than $10^{-6}$, typically around $10^{-7}$ mutants per µg of DNA [spontaneous means with no comX expression or overexpression].

By "at least 90% identity to the endogenous comX gene of said strain", it is meant—as particular embodiments of the method—at least 91%, at least 92%, at least 93%, at least 94%, at least 95%, at least 96%, at least 97%, at least 98%, or at least 99% identity. In a particular embodiment, said comX gene has 100% identity to the endogenous comX gene of said strain.

In a particular embodiment, said method is implemented with a strain of the *Lactococcus* genus selected from the group consisting of *Lactococcus lactis, Lactococcus raffinolactis, Lactococcus plantarum, Lactococcus piscium, Lactococcus garivieae, Lactococcus fujiensis* and *Lactococcus chungangensis*.

In a particular embodiment, said method is implemented with a strain of the *Lactococcus lactis* species. Said method comprises the following steps:
(a) providing a strain of the *Lactococcus lactis* species;
(b) transforming said strain with a plasmid expressing a comX gene having at least 90% identity to the polynucleotide sequence of SEQ ID NO:1, 3 or 5;
(c) contacting said strain obtained in step (b) with an exogenous marker DNA polynucleotide in a medium and incubating the resulting mixture for integration of the exogenous DNA polynucleotide into the genome of said strain; and
(d) determining the rate of recombination events;
wherein a rate of at least $1 \times 10^{-6}$ transformants per µg of DNA is indicative of a strain of the *Lactococcus lactis* species which is transformable through natural competence.

In a particular embodiment, said method is implemented with a strain of the *Lactococcus* raffinolactis species. Said method comprises the following steps:

(a) providing a strain of the *Lactococcus raffinolactis* species;
(b) transforming said strain with a plasmid expressing a comX gene having at least 90% identity to the polynucleotide sequence of SEQ ID NO:7;
(c) contacting said strain obtained in step (b) with an exogenous marker DNA polynucleotide in a medium and incubating the resulting mixture for integration of the exogenous DNA polynucleotide into the genome of said strain; and
(d) determining the rate of recombination events;
wherein a rate of at least $1 \times 10^{-6}$ transformants per µg of DNA is indicative of a strain of the *Lactococcus lactis* species which is transformable through natural competence.

In some embodiments, the comX gene is from a strain of the same species, in particular of the same subspecies, as the strain provided in step a). In some embodiments, the comX gene is identical (100% identity) to the polynucleotide sequence of the endogenous comX gene of the strain of step a).

In some embodiments, when the strain of step a) is a *Lactococcus lactis* subsp. *lactis* strain, the comX gene has at least 90%, at least 91%, at least 92%, at least 93%, at least 94%, at least 95%, at least 96%, at least 97%, at least 98%, at least 99%, or 100% identity to the polynucleotide sequence of SEQ ID NO:1.

In some embodiments, when the strain of step a) is a *Lactococcus lactis* subsp. *cremoris* strain the comX gene has at least 90%, at least 91%, at least 92%, at least 93%, at least 94%, at least 95%, at least 96%, at least 97%, at least 98%, at least 99%, or 100% identity to the polynucleotide sequence of SEQ ID NO:3 or SEQ ID NO:5.

In some embodiments, when the strain of step a) is a *Lactococcus raffinolactis* strain the comX gene has at least 90%, at least 91%, at least 92%, at least 93%, at least 94%, at least 95%, at least 96%, at least 97%, at least 98%, at least 99%, or 100% identity to the polynucleotide sequence of SEQ ID NO:7.

In some embodiments, when the strain of step a) is a *Lactococcus plantarum* strain the comX gene has at least 90%, at least 91%, at least 92%, at least 93%, at least 94%, at least 95%, at least 96%, at least 97%, at least 98%, at least 99%, or 100% identity to the polynucleotide sequence of SEQ ID NO:9.

In some embodiments, when the strain of step a) is a *Lactococcus piscium* strain the comX gene has at least 90%, at least 91%, at least 92%, at least 93%, at least 94%, at least 95%, at least 96%, at least 97%, at least 98%, at least 99%, or 100% identity to the polynucleotide sequence of SEQ ID NO:11.

In some embodiments, when the strain of step a) is a *Lactococcus garvieae* strain the comX gene has at least 90%, at least 91%, at least 92%, at least 93%, at least 94%, at least 95%, at least 96%, at least 97%, at least 98%, at least 99%, or 100% identity to the polynucleotide sequence of SEQ ID NO:13, SEQ ID NO:15, or SEQ ID NO:17.

In some embodiments, when the strain of step a) is a *Lactococcus fujiensis* strain the comX gene has at least 90%, at least 91%, at least 92%, at least 93%, at least 94%, at least 95%, at least 96%, at least 97%, at least 98%, at least 99%, or 100% identity to the polynucleotide sequence of SEQ ID NO:19.

In some embodiments, when the strain of step a) is a *Lactococcus chungangensis* strain the comX gene has at least 90%, at least 91%, at least 92%, at least 93%, at least 94%, at least 95%, at least 96%, at least 97%, at least 98%, at least 99%, or 100% identity to the polynucleotide sequence of SEQ ID NO:21.

It is preferable to use, as an exogenous marker DNA polynucleotide, a polynucleotide bearing a gene which is initially not present in the *Lactococcus* strain of step a) [even as a mutated version]. This would avoid that during step c) the *Lactococcus* strain acquires a functional gene by other means than natural competence, e.g. by spontaneous mutation of its genome.

As an example, the exogenous marker DNA polynucleotide bears a gene encoding a luciferase gene. Accordingly, a *Lactococcus* strain which has integrated the exogenous DNA polynucleotide into its genome may be selected for expression of the luciferase. Only strains that express the luciferase gene (i.e., integrated) will be detectable by bioluminescence.

As another example, the exogenous marker DNA polynucleotide bears an antibiotic resistance gene. Accordingly, a *Lactococcus* strain which has integrated the exogenous DNA polynucleotide into its genome may be selected by plating the cells onto a medium comprising said antibiotic.

An example of a method for identifying a strain of the *Lactococcus* genus which is transformable through natural competence according to the present invention (Assay A) may be performed using the following steps:

i) Providing a strain of the *Lactococcus* genus, in particular of the *Lactococcus lactis* species.
ii) Transforming said strain with a plasmid expressing a comX gene having at least 90% identity, preferably having 100% identity to the endogenous comX gene of said strain (e.g. the pGhP32comX$_{MG}$ plasmid of Materials and Methods).
iii) Pre-culturing the transformed strain overnight in a complex medium supplemented with glucose (e.g. M17G) at 30° C.
iv) Diluting about 1.5 mL of the pre-culture in about 8.5 mL of fresh medium.
v) After about 2 hours further growth at 30° C., washing the cells twice with distilled water and adjusting the $OD_{600}$ to 0.05 in a chemically defined medium (e.g. CDM) containing 5 µg mL$^{-1}$ erythromycin and an osmo-stabilizer (e.g. 5% [v/v] glycerol or 5% [w/v] mannitol).
vi) Adding 5 µg of exogenous DNA polynucleotide bearing an antibiotic resistance gene to 300 µl of the culture medium (e.g. the 3.7 kb PCR product generated from the pGEMrpsL plasmid as described in Materials and Methods).
vii) Incubating the resulting culture for about 6 hours at 30° C.
viii) Plating the cells onto agar plates comprising the complex medium supplemented with glucose (e.g. M17G) and appropriate antibiotic (i.e. corresponding to the antibiotic resistance gene of the exogenous DNA polynucleotide) and incubating for about 48 hours.
ix) Counting the colony forming units (CFU) and determining the transformation rate, wherein a transformation rate of at least $1 \times 10^{-6}$ transformants per µg of DNA is indicative of a strain which is transformable through natural competence.

The transformation rate may be calculated as the number of antibiotic-resistance CFU mL$^{-1}$ divided by the total number of viable CFU mL$^{-1}$.

Various preferred features and embodiments of the present invention will now be described by way of non-limiting examples.

EXAMPLES

Example 1: Induction of the comGA Promoter by Constitutive comX Expression in Various Strains of the *Lactococcus* Species a) In *Lactococcus lactis* Subsp. *Cremoris* Strains (MG1363 and KW2)

To test the ability of ComX to induce the late competence genes in *Lactococcus lactis* subsp. *cremoris* strains, a constitutive comX expression plasmid (pGhP32comX$_{MG}$) was created by cloning the comX gene from strain MG1363, under the control of the lactococcal P$_{32}$ promoter on the thermosensitive plasmid pG$^+$host9. The latter was introduced in strain KW2 that contains a chromosomally-encoded P$_{comGA[MG]}$-luxAB transcriptional fusion (BLD101). The promoter of the late competence gene comGA (P$_{comGA}$) contains a putative ComX-binding motif and is used here as proxy for competence activation in the ComX$^+$ strain.

As alternative for more resistant strains to electro-transformation, and subsequently to chromosome integration, a portable luminescent reporter system was also constructed. This replicative plasmid carries the luminescent reporter P$_{comGA[MG]}$-luc with the P$_{32}$-comX$_{MG}$ cassette. The pGhP32comX$_{MG}$-P$_{comGA[MG]}$-luc plasmid was transformed in strain MG1363.

Specific P$_{comGA[MG]}$-luc/luxAB activities were monitored for the different strains constructed. The luminescent assays were performed in rich (M17G) and/or CDM media comparing the luciferase activity between the overexpressing comX strain and its related negative control (no additional comX copy).

In the KW2 strain containing the P$_{comGA[MG]}$-luxAB reporter as mono-copy in their chromosome, specific luciferase activity was observed for KW2 containing the P$_{32}$-comX cassette allowing the constitutive production of ComX. This confirms that comX expression can be carried out in various *L. lactis* subsp. *cremoris* strains using an exogenous comX gene obtained from the same strain or from a strain of the same subspecies. Eight recombinant clones of the KW2 ComX$^+$ reporter strain were randomly selected and their specific luciferase activity was monitored in CDM growth conditions. This medium was chosen because it was shown to be permissive for competence development in various streptococcal species. To ensure reproducibility of the assay, exponentially-growing cells in complex medium (M17 conditions) were washed and inoculated in fresh CDM before starting the experiment. As expected, all tested ComX$^+$ clones (cl01 to cl08) displayed between 10$^1$- and 10$^4$-fold higher specific luciferase (Lux) activity than the control strain carrying the empty vector (FIGS. 2A and 2B).

Similar results were obtained with the portable luminescent reporter systems in MG1363 (FIG. 2C).

These results strongly suggest that, in the *L. lactis* subsp. *cremoris* strains MG1363 and KW2, ComX induces the comG operon. Additionally, these observations validate these reporter fusions (both chromosomal and plasmid-borne) as a tool to identify conditions capable to activate the comG-operon which is essential to natural transformation.

b) In a *L. lactis* Subsp. *Lactis* Strain (IL1403)

A constitutive comX expression plasmid (pGhP32comX$_{IO}$) was created by cloning the comX gene from strain IO-1, under the control of the lactococcal P$_{32}$ promoter on the thermosensitive plasmid pG$^+$host9. A portable luminescent reporter system was also constructed; this replicative plasmid carries the luminescent reporter P$_{comGA[IO]}$-luc with the P$_2$-comX$_{IO}$ cassette. The promoter of the late competence gene comGA ($P_{comGA}$) contains a putative ComX-binding motif and is used here as proxy for competence activation in the ComX+ strain.

This replicative plasmid pGhP32comX$_{IO}$-P$_{comGA[IO]}$-luc was transformed in strain IL1403 and specific P$_{comGA[IO]}$-luc activities were monitored. One of the IL1403 transformants produced specific P$_{comGA[IO]}$-luc activities confirming that ComX induces the comG operon (FIG. 2D).

Example 2: Analysis of Essential Late Com Genes Present in L. lactis Genomes Among L. lactis strains, genomic variability was previously investigated for comX and dprA alleles (Wydau et al., 2006). While all strains (31/31) display a complete version of comX, the dprA content is variable among subspecies: 50% of the lactis strains (10/20) contain nonsense mutations in dprA while all cremoris strains (11/11) harbor an intact and potentially functional dprA gene.

Since dprA is hypothesized to be important in the natural competence mechanism, its integrity in L. lactis strains prompted us to further analyze the minimal set of late com genes (17 candidate genes including comX; FIG. 1) in the genomes of 3 subsp. cremoris strains and 1 subsp. lactis strain which are publicly available (strains MG1363, SK11, KW2 and IL1403). This in silico analysis reveals that the genome of SK11 contains a high number of pseudogenes in key competence genes (between 5 and 8 incomplete late com genes) due to transposon insertion or frameshifting events (nucleotide(s) insertion or deletion). In particular, the presence of transposable elements in comGA and/or comEC genes, which are respectively essential for pilus assembly and DNA transport, strongly suggests that natural transformation is no more functional in those strains. Although the set of full-length competence genes in the laboratory strain MG1363 is larger, mutations in comEC (nucleotide insertion) and coiA (nonsense mutation) probably impair its ability to transform DNA by competence (Wegmann et al., 2007). Those mutations were also found in the genome of its isogenic derivative NZ9000, which strongly suggests that they do not result from DNA sequencing errors. As far as the L. lactis subsp. lactis IL1403 strain is concerned, its dprA gene contains nonsense mutations probably impairing its ability to transform DNA by competence. In contrast, strain KW2 of plant origin (com fermentation) contains the whole set of known essential late genes required to fulfil natural DNA transformation, making it the best candidate to further study the functionality of competence in the cremoris subspecies. Two other strains from our collection, L. lactis subsp. lactis SL12651 and SL12653, were also found to contain the whole set of known essential late genes (FIG. 1).

Example 3: Effect of Growth Conditions on ComX Activation

We investigated the effect of pre-culturing and culturing conditions (M17G, THBG, and CDM) on the activation of the reporter fusion in the ComX+ strain. For this purpose, clone 02 (FIG. 2A) was selected since it exhibits the strongest Lux activity. Interestingly, more than a 20-fold variation in the maximum Lux activity was dependent on the pre- and culturing medium which was used (FIG. 3). Particularly, a positive impact of the transition of pre-culture cells from a complex medium to a defined medium was observed. The highest specific Lux activity (~3×10$^6$ RLU OD$_{600}$$^{-1}$) was obtained for a switch from M17G to CDM, followed by THBG to CDM, while all other combinations gave lower activities (between ~1.5× and 5.5×10' RLU OD$_{600}$$^{-1}$). This indicates that first a chemically defined medium is superior for maximizing activation of late com genes of L. lactis KW2 than complex rich media, but also that the switch from complex medium (e.g. M17G or THBG) to defined medium is critical.

Together, these results show that ComX is functional in strain KW2 when it is constitutively produced (i.e. expressed) and that growth conditions have a significant impact on the activation of late com genes.

Example 4: Constitutive comX Expression Induces Natural Transformation a) Acquisition of Single Mutations in the KW2 Genome from Exogenous DNA We first tested the transfer of single point mutations in the chromosome of the ComX+ KW2 strain. The transforming PCR fragments used encompass the mutated rpsL allele of a spontaneous streptomycin-resistant (Str$^r$) clone of L. lactis subsp. cremoris MG1363 (strA1 allele, also called rpsL*). This mutated allele bears an A→T substitution at position 167 [resulting in the altered ribosomal protein S12 with mutation K561] as compared to the sequence of the wild-type, streptomycin-sensitive MG1363. In addition to this mutation, the two rpsL alleles differ by a silent nucleotide substitution at position 39 (T→G). The sequence of the rpsL (wild-type) and rpsL* (conferring streptomycin resistance) alleles are disclosed respectively as SEQ ID NO:23 and NO:24 (FIG. 4A). Independently of these two substitutions located at positions 39 and 167, the rpsL alleles of KW2 and MG1363 differ by a nucleotide substitution at position 156 (A in MG1363, T in KW2). The rpsL allele of KW2 is disclosed as SEQ ID NO:25 (FIG. 4A). To ensure efficient recombination, the transforming PCR product also contains upstream and downstream recombination arms of ~1.85 kb surrounding the strA1 mutation. Transformation assays were performed with the eight previously selected clones of the ComX+ reporter strain (BLD101 [pGhP32comX$_{MG}$]) and the control strain (BLD101 [pG+host9], empty vector) using the standard protocol reported in Material and Methods. Validation of natural transformation is made by sequencing the rpsL region covering the point mutations from the donor DNA conferring streptomycin resistance using primers RpsL Univ UP and RpsL Univ DN.

Remarkably, the ComX+ clones 02 and 04 that displayed the highest P$_{comGA}$ activation (≥7×10$^5$ RLU OD$_{600}$$^{-1}$) yielded mutation frequencies ~15-fold higher than the background level of spontaneous mutation that was calculated in the absence of DNA (FIG. 4B). After subtraction of the background, a transformation rate of up to 4×10$^{-5}$ transformants per µg of DNA (~10$^4$ transformants ml$^{-1}$) was obtained for clone 02 which displays the highest P$_{comGA}$ activation. In contrast, the negative control strain had a spontaneous mutation rate of ~1×10$^{-7}$ transformants per µg of DNA.

The rpsL ORF of 10 Str$^r$-derivatives of cl02 was amplified by PCR and sequenced. In all cases, we observed the co-transfer of strA1 (mutation A→T at position 167 of the rpsL gene) and the closely-located T→A mutation at position 156. In some cases, the T→G mutation at position 39 was also co-transferred with strA1. The chimeric nature of rpsL in some Str$^r$ ComX+ derivatives of KW2 (i.e. presence of both mutations at positions 156 and 167 without the mutation at position 39) ultimately demonstrates that a recombination process occurred between the exogenous and chromosomal DNA (FIG. 4A). In contrast, this rearrangement was not observed in the rpsL gene of spontaneous Str$^r$ mutants obtained in the negative control experiments (i.e. assays performed in absence of exogenous DNA, or with the control strain carrying the empty vector in presence of exogenous DNA). These results show that exogenous DNA can enter KW2 cells and be integrated in their chromosome by homologous recombination when a certain threshold of comX expression is reached.

b) Construction of Deletion Mutants by Natural Competence in L. lactis Subsp. Cremoris KW2 Overexpressing comX The previous result (Example 4, section a) strongly suggests that DNA transfer occurs in L. lactis KW2. The 3 mutations transferred by natural transformation are grouped on a 128-bp fragment. If a longer DNA fragment could be similarly integrated in the L. lactis chromosome remains to be determined.

We wondered if overlap PCR as donor DNA could equivalently allow gene insertions or gene deletions. The idea was to replace the target gene by an antibiotic resistance cassette, i.e. the chloramphenicol resistance cassette $P_{32}$-cat. For this purpose, a DNA fragment was constructed by overlap PCR containing the $P_{32}$-cat cassette flanked by two homologous arms (minimum ~1.5 kb) containing the upstream and downstream regions of the targeted gene.

To this end, exogenous DNA polynucleotides containing $P_{32}$-cat surrounded by KW2-specific recombination arms (~1.5 kb) were assembled in vitro by overlapping PCR to target the comEC, mecA, ciaRH, covRS or clpC gene (see Materials and Methods for details) and transferred by natural transformation in the ComX$^+$ strain (cl02). Validation of natural transformation is made by sequencing the targeted region (comEC, mecA, ciaRH, covRS or clpC, which should contain the chloramphenicol resistance cassette $P_{32}$-cat) using primers listed in Table 3.

The transformation rate observed for overlap PCR products was ~1.2×10$^{-6}$ to 1.1×10$^{-4}$ transformants per µg of DNA for the different overlap DNA fragments that were tested (see FIG. 5). Compared to the transformation rate observed for the exchange of a homologous DNA fragment containing only three point mutations (rpsL* donor DNA; 8×10$^{-4}$ transformants per µg of DNA), these rates are relatively high for DNA double recombination deletion/replacement.

Example 5: A KW2 ΔcomEC Mutant is Unable of Natural Competence Transformation

To confirm that the observed horizontal DNA transfer in ComX$^+$ KW2 cells was indeed mediated by natural competence, and not by phage transduction or conjugation, we investigated the role of the ComEC protein, which is essential for the uptake of transforming DNA through the cell membrane (the comEA gene, together with the comFA, comGA, dprA, coiA, ssbA, radA, radC, recA and recX genes are preceded by a Com-box and have been found to be activated in KW2 following constitutive comX expression; data not shown).

To create the ΔcomEC strain, clone 02 of the ComX$^+$ reporter strain, which was tested above, was grown in CDM conditions in presence of PCR products encompassing the comEC gene disrupted by the insertion of the chloramphenicol resistance cassette $P_{32}$-cat (see Materials and Methods). Four mutants with disrupted comEC (BLD102 [pGhP32comX$_{MG}$] cl01 to cl04) were validated by PCR for $P_{32}$-cat insertion in comEC. Transformation assays with the mutated rpsL allele showed that the frequencies of appearance for Str$^r$ clones in all tested ΔcomEC derivatives were similar to the background level of spontaneous rpsL mutation frequencies (<10$^{-1}$) (FIG. 6). Although heterogeneity in $P_{comGA}$ activation was observed between clones as previously reported for the WT ComX$^+$ reporter strain, half of the ΔcomEC derivative clones (i.e. cl01 and cl03) displayed maximum specific Lux activity similar to the transformable WT strains (>1.0×10$^6$ RLU OD$_{600}$$^{-1}$) (FIG. 4B). This shows that the transformation defect in these ΔcomEC clones does not result from a too low production of ComX.

Taken together, these results demonstrate that natural DNA transformation could be activated by ComX overexpression in L. lactis subsp. lactis KW2. Moreover, to the best of our knowledge, these data provide the first ever experimental evidence of transformation of L. lactis by natural competence.

Example 6: Natural Competence in Two Strains of the L. Raffinolactis Species

Following the positive results obtained regarding natural competence in Lactococcus lactis strains, other strains of the Lactococcus genus were tested. Two strains of L. Raffinolactis were able to capture plasmid pGhost-Core (15 µg/300 µl) used as donor DNA: LMG13098 and LMG14164. These results suggest that these two strains of L. Raffinolactis are naturally competent for plasmid transformation and that, in these strains, natural competence is independent of artificial comX-overexpression.

The fact that another Lactococcus species could be transformed by competence opens additional possibilities for industrial applications.

Example 7: Transformation by Natural Competence in 2 Lactococcus lactis Subsp. Lactis Strains Two Lactococcus lactis subsp. lactis strains, SL12651 and SL12653, carrying all the essential late com genes (FIG. 1) were tested. As donor DNA, PCR fragments which encompass the mutated rpsL allele (rpsL*) of a spontaneous streptomycin-resistant (Str$^r$) clone of L. lactis subsp. lactis IL1403 was used. Cells were pre-cultured overnight in a complex medium supplemented with glucose (e.g. M17G) at 30° C. Cells were washed twice with distilled water and inoculated at an OD$_{600}$ of 0.05 in 200 µl M17G containing 25 µg mL$^{-1}$ donor DNA rpsL*. After 24 hours of culture at 30° C., cells incubated or not with donor DNA were spread onto agar plates comprising the complex medium supplemented with glucose (e.g. M17G) and appropriate antibiotic (i.e. streptomycin). CFUs were counted after 48 hours of incubation at 30° C. Remarkably, SL12651 and SL12653 yielded a transformation rate of up to 1×10$^{-6}$ of DNA when grown in M17G rich medium (FIG. 7A; +DNA). In contrast, the negative control in absence of donor DNA had a spontaneous mutation rate of 6×10$^{-9}$ (FIG. 7A; −DNA). The transformants were validated by sequencing the rpsL region covering the point mutation from the donor DNA conferring streptomycin resistance.

Then, the SL12653 strain was assayed in the same conditions with variable quantity of donor DNA (0.5, 2.5, 5 and 25 µg mL$^{-1}$). It has been shown that the transformation rate obtained is directly correlated to the initial quantity of donor DNA, yielding up to a transformation rate of 5×10$^{-6}$ (FIG. 7B).

Moreover, to confirm that the observed horizontal DNA transfer was mediated by natural competence, the comX gene of SL12653 was knocked-out (as described in example 5 above). Three mutants of SL12653 with disrupted comX gene were designed by inserting PCR products encompassing the comX gene disrupted by the insertion of the chloramphenicol resistance cassette $P_{32}$-cat and validated by PCR for $P_{32}$-cat insertion. Transformation assays with rpsL* as donor DNA in all ΔcomX clones (ComX⁻) showed that the frequencies of appearance of Str$^r$ clones were similar to the background level of spontaneous mutation frequencies (FIG. 7C). These results confirm that in SL12653, the transformation is dependent on the expression of the endogenous comX gene.

Finally, the transformability of the SL12653 strain was also assayed by overexpressing the comX gene. Thus, an inducible comX expression plasmid [pGhPxylTcomX$_{IO}$] was constructed by cloning the comX gene from strain *L. lactis* subsp. *lactis* IO-1 under the control of the $P_{XylT}$ promoter from strain IO-1 on the thermosensitive plasmid pG+host9. This plasmid is a variant of pGhPxylTcomX$_{MG}$ (pGIFPT001) described in David et al., 2017. The transformation procedure described in David et al (2017) was followed. In presence of xylose (1%), SL12653 [pGhPxylTcomX$_{IO}$] yielded a transformation rate at least 20-fold higher than in absence of xylose, confirming that the overexpression of comX in SL12653 increased its transformability by natural competence.

Materials and Methods

Bacterial Strains, Plasmids, and Growth Conditions

The bacterial strains and plasmids used in this application are listed in Table 2.

TABLE 2 list of used bacterial strains and plasmids

| Strain or plasmid | Characteristics [a] | Source or reference |
|---|---|---|
| *E. coli* | | |
| TG1 | supE hsdΔ5 thi Δ(lac-proAB) F'[traD36 proAB⁺ lacI$^q$ lacZΔM15] | Sambrook, J., E. F. Fritsch, and T. Maniatis. 1989. Cold Spring Harbor Laboratory, Cold Spring Harbor, N.Y. |
| EC1000 | Km$^r$, recA⁺; MC1000 containing a copy of the repA gene from pWV01 in its chromosome | Law, J., G. Buist, A. Haandrikman, J. Kok, G. Venema, and K. Leenhouts. 1995. J. Bacteriol. 177: 7011-7018. |
| *L. lactis* | | |
| MG1363 | Laboratory strain, dairy origin | Gasson, M. J. 1983. J. Bacteriol. 154: 1-9. |
| KW2 | Wild-type isolate from corn fermentation | Kelly, W. J., E. Altermann, S. C. Lambie, and S. C. Leahy. 2013. Front Microbiol. 4: 257. |
| IL1403 | Laboratory strain, dairy origin | Chopin, A., M. C. Chopin, A. Moillo-Batt, and P. Langella. 1984. Plasmid 11: 260-263 |
| IO-1 | Wild-type isolate from water in the drain pit of a kitchen sink | Ishizaki A, Osajima K, Nakamura K, Katsunori K, Hara T, and Ezaki T. 1990. J. Gen. Appl. Microbiol., 36, 1-6 |
| SL12651 | Wild-type isolate from plant material (maize) | DuPont/Danisco collection |
| SL12653 | | |
| BLD101 | KW2 kw2_0563::P$_{comGA[MG]}$-luxAB | This application |
| BLD102 | BLD101 comEC::P$_{32}$-cat | This application |
| BLD107 | BLD101 mecA::P$_{32}$-cat | This application |
| BLD108 | BLD101 ciaRH::P$_{32}$-cat | This application |
| BLD109 | BLD101 covRS::P$_{32}$-cat | This application |
| BLD105 | BLD101 clpC::P$_{32}$-cat | This application |
| *L. raffinolactis* | | |
| LMG13098 | Wild-type isolate from garden carrots | LMG collection |
| LMG14164 | Wild-type isolate from goose | LMG collection |
| Plasmids | | |
| pGEM ®-T easy | Ap$^r$; cloning vector | Promega |
| pG+host9 | Em$^r$ Ts | Maguin, E., H. Prevost, S. D. Ehrlich, and A. Gruss. 1996. J. Bacteriol. 178: 931-935 |
| pGhost-Core | Em$^r$ Ts; pG+host9 derivative containing the Core part of the resolution site IRS recognized by the TnpI from Tn4430 | This application |
| pMG36eT | Em$^r$; *E. coli-L. lactis* shuttle vector containing the P$_{32}$ constitutive promoter from *L. lactis* | Fontaine, L. and P. Hols. 2008. Appl. Environ. Microbiol. 74: 1102-1110. |
| pJIM4900 | Em$^r$ Ts; pG+host9 derivative containing the luxAB genes of *Photorhabdus luminescens* | E. Guédon, (laboratory collection) |
| pXL | Em$^r$; pTRKH2 derivative containing the luc reporter gene | Blomqvist T, Steinmoen H, Håvarstein L S. Appl Environ Microbiol. 2006. Oct; 72(10): 6751-6. |
| pSEUDOPusp45GFP | Em$^r$; suicide vector containing the llmg_pseudo_10(kw2_0563)::P$_{usp45}$-gfp⁺ insertion cassette | Overkamp, W., K. Beilharz, W. R. Detert Oude, A. Solopova, H. Karsens, A. Kovacs, J. Kok. O. P. Kuipers, and J. W. Veening. 2013. Appl. Environ. Microbiol. 79: 6481-6490. |
| pUC18Cm | Ap$^r$ Cm$^r$; pUC18 derivative containing the P32-cat cassette | Goffin, P., F. Lorquet, M. Kleerebezem, and P. Hols. 2004. J. Bacteriol. 186: 6661-6666. |

TABLE 2-continued list of used bacterial strains and plasmids

| Strain or plasmid | Characteristics [a] | Source or reference |
|---|---|---|
| pUC18Ery | Ap[r] Em[r]; pUC18 derivative containing an erythromycin resistance marker | van Kranenburg, R., J. D. Marugg, I. I. van Swam, N. J. Willem, and W. M. de Vos. 1997. Mol. Microbiol. 24: 387-397. |
| pNZ5319 | Em[r] Cm[r]; pACYC184 derivative containing the P32-cat cassette surrounded by lox sites | Lambert, J. M., R. S. Bongers, and M. Kleerebezem. 2007. Appl. Environ. Microbiol. 73: 1126-1135. |
| pGhPcomGAluxAB | Em[r] Ts; pG+host9 derivative containing the llmg_pseudo_10 (kw2_0563)::$P_{comGA[MG]}$-luxAB insertion cassette | This application |
| pGhP32comX$_{MG}$ | Em[r] Ts, pG+host9 derivative carrying comX of strain MG1363 under the control of the constitutive promoter $P_{32}$ | This application |
| pGhP32comX$_{IO}$ | Em[r] Ts, pG+host9 derivative carrying comX of strain IO-1 under the control of the constitutive promoter $P_{32}$ | This application |
| pGhP32comX$_{MG}$-P$_{comGA[MG]}$-luc | pGhP32comX$_{MG}$ derivative carrying a $P_{comGA[MG]}$-luc fusion | This application |
| pGhP32comX$_{IO}$-P$_{comGA[IO]}$-luc | pGhP32comX$_{IO}$ derivative carrying a $P_{comGA[IO]}$-luc fusion | This application |
| pGEMrpsL* | Ap[r], pGEM ®-T easy derivative carrying the rpsL* gene (strA1 allele) | This application |
| pUCcomECcat | Ap[r] Em[r] Cm[r], pUC18Ery derivative allowing the insertion of $P_{32}$-cat at the comEC locus | This application |
| pGhPxylTcomX$_{IO}$ | Em[r] Ts, pG+host9 derivative carrying comX of strain IO-1 under the control of the inducible promoter $P_{xylT}$ from IO-1 | This application |

[a] Em[r], Ap[r], Cm[r] and Ts: erythromycin, ampicillin, chloramphenicol resistance and thermo-sensitive RepA protein, respectively.

*Escherichia coli* was grown with shaking at 37° C. in Lysogeny-Broth (LB) broth. Plasmids derived from pMG36e and pG+host9 were constructed in *E. coli* strains TG1 and EC1000, respectively. *L. lactis* and *L. Raffinolactis* were cultivated in M17 (Becton, Dickinson, and Company), Todd Hewitt broth (THB) (Becton, Dickinson, and Company) or CDM at 30° C. without agitation. M17 and THB were supplemented with 0.5% (w/v) of glucose (M17G and THBG, respectively). Solid agar plates were prepared by adding 2% (w/v) agar to the medium. When required, 5 μg ml$^{-1}$ of erythromycin, 1 mg ml$^{-1}$ of streptomycin, and/or 10 μg ml$^{-1}$ of chloramphenicol were added to the medium for *L. lactis* and *L. Raffinolactis*; and 250 μg ml$^{-1}$ of erythromycin, 250 μg ml$^{-1}$ of ampicillin, 10 μg ml$^{-1}$ of chloramphenicol for *E. coli*.

Detection of Absorbance and Luminescence.

Growth (OD$_{600}$) and luciferase (Lux) activity were monitored at 10-minutes intervals in a Varioskan Flash multi-mode reader (ThermoFisher). The luciferase activity is expressed in relative light units (RLU) and the specific luciferase activity in RLU OD$_{600}$$^{-1}$.

DNA Techniques and Electrotransformation

General molecular biology techniques were performed according to the instructions given by Sambrook et al. (1989). Electrotransformation of *E. coli* and *L. lactis* was performed as previously described. The electrotransformed cells of *L. lactis* were immediately resuspended in 1 ml of M17G and incubated for 6 hours at 30° C. Chromosomal DNAs of *L. lactis* were prepared as previously described. PCRs were performed with Phusion DNA polymerase (NEB) in a GeneAmp PCR system 2400 (Applied Biosystems). The primers used in this application are listed in Table 3.

TABLE 3 list of primers

| Primer name | Sequence (5'-3') |
|---|---|
| Primers used for the construction of the constitutive comX expression plasmid pGhP32comX$_{MG/IO}$: | |
| BID_ComXSDLLCup | AAAAGAGCTCAATTATGAAAAAGAGG |
| BID_ComXSDLLCdown | AAAACTGC AGTTAATCATCATCTCG |
| BID_ComXSDLLLup | AAAAGAGCTCATAAAAGGAGAACTTTCC |
| BID_ComXSDLLLdown | AAAACTGCAGTCACTCTTCGTCTTC |

TABLE 3-continued list of primers

| Primer name | Sequence (5'-3') |
|---|---|
| BID_pMGP32UpMfeI | ATATCAATTGGTCCTCGGGATATGATAAG |
| BID_pMGTerDown | GACTTTGAACCTCAACTCC |

Primers used for the construction of the $P_{comGA[MG]}$-luxAB reporter strain BLD101:

| | |
|---|---|
| BID_LuxLLCf1 | ATAGTCTCGAGTTTAAGCAATTGAATCGCTAG |
| BID_LuxLLCr1 | GCAAAAAGTTTCCAAATTTCATACTAGAATATACGCAATTTG |
| BID_LuxLLCf2 | CAAATTGCGTATATTCTAGTATGAAATTTGGAAACTTTTTGC |
| BID_LuxLLCr2 | GCGAAAGGATCCCTATTAGGTATATTCCATGTGG |
| BID_P3pseudoLLC | GCTCCCTCGAGGGCGGCTCTGTTGGATTAATATATGG |

Primers used for the construction of portable luc reporter vectors:

| | |
|---|---|
| BID_LucLLCr1 | CTTTATGTTTTTGGCGGATCTCATACTAGAATATACGCAATTTG |
| BID_LucLLCf2 | CAAATTGCGTATATTCTAGTATGAGATCCGCCAAAAACATAAAG |
| BID_LucLLCr2 | GCGAAAGGATCCTTACAATTTGGGCTTTCCG |
| BID_PcomGALLCF1* | AAAACCCGGGTTTAAGCAATTGAATCGCTAG |
| BID_PcomGALLLF1* | 5' AAAACCCGGGAAATAAATGGCTACAAAATT |
| BID_lucR1* | AAAACGGCCGTTACAATTTGGGCTTTCCG |
| BID_luxLLLf1 | ATAGTCTCGAGAAATAAATGGCTACAAAATT |
| BID_lucLLLr1 | CTTTATGTTTTTGGCGGATCTCATACTAGACTATACGCAAATAATC |
| BID_lucLLLf2 | GATTATTTGCGTATAGTCTAGTATGAGATCCGCCAAAAACATAAAG |
| BID_lucLLLr2 | GCGAAAGGATCCTTACAATTTGGGCTTTCCG |

Primers used for the construction of pGhost-Core

| | |
|---|---|
| DD-pGhost-CoreUp | AGCTTCCTAATACAACACAATTAATATTGTGTTGTATTATTG |
| DD-pGhost-CoreDW | AATTCAATAATACAACACAATATTAATTGTGTTGTATTAGGA |

Primers used for rpsL sequencing:

| | |
|---|---|
| RpsL Univ UP | ATGCCTACAATTAACCAAT |
| RpsL Univ DN | CACCGTATTTAGAACGG |
| LR_RpsL Univ UP | ATGCCTACTATTAACCAAT |
| LR_RpsL Univ DN | TACCGTATTTAGAACGG |

Primers used for rpsL amplification:

| | |
|---|---|
| BID_LLcdacARpsL | AGTAGTATCAGCACTGACAGC |
| BID_LL1cfusARpsL | ACACCTTTGTTCTTGAAGG | primers used for the construction of the comEC disruption mutant:

| | |
|---|---|
| BID_ComECLLCUp | AAAGAGCTCAAAATAAAAATGAAATTATGG |
| BID_ComECLLCDown | AAAGCTAGCGGGAAAAAATTGTGAATTAC |
| BID_CatUpSpeI | AAAAACTAGTGCAGTTTAAATTCGGTCCTCGG |
| BID_CatDownSpeI | AAAAACTAGTGTACAGTCGGCATTATCTCAT |

Primers used for the construction and validation of the mecA deletion mutant:

| | |
|---|---|
| BID_fgt01FmecArec | CTTTAATGATGGAATGATTG |
| BID_fgt01RVmecArec | CTATTAATCTTATCATATCCCGAGGATCCATATAACTATATGAAACC |

TABLE 3-continued list of primers

| Primer name | Sequence (5'-3') |
|---|---|
| BID_fgt02Fcat | TCCTCGGGATATGATAAGATTAATAG |
| BID_fgt02RVcat | TCTCATATTATAAAAGCCAGTCATTAG |
| BID_fgt03FmecArec | CTAATGACTGGCTTTTATAATATGAGACTTAGAAAAATCTAAATATGGTTG |
| BID_fgt03RVmecArec | GAAGATTTTTAATTTCAAGTGTAG |
| BID_mecAKOF | TCAGTACCGAAAAACGAATG |
| BID_mecAKORV | ATTTACCAGTTCCGTTAGG |

Primers used for the construction and validation of the ciaRH deletion mutant:

| BID_ciaRHUPF | TAACAATGATACAGAAGATG |
|---|---|
| BID_ciaRHUPRVRec | CTATTAATCTTATCATATCCCGAGGATATTTTTGTCTTGTACTAGG |
| BID_fgt02Fcat | TCCTCGGGATATGATAAGATTAATAG |
| BID_fgt02RVcat | TCTCATATTATAAAAGCCAGTCATTAG |
| BID_ciaRHDownFRec | CTAATGACTGGCTTTTATAATATGAGAGAGAGAAAAAAATTACTGAC |
| BID_ciaRHDownRV | AAAATCTGTTAGAACTGTTG |
| BID_ciaRHKODiagF | AAGATAAGGCAGTTGAAATG |
| BID_ciaRHKODiagRv | TCACCATGTGAATAAAGTCC |

Primers used for the construction and validation of the covRSdeletion mutant:

| BID_covRSfgt01F | CAAAAATGTGAAGCTTATC |
|---|---|
| BID_covRSfgt01RVRec | CTATTAATCTTATCATATCCCGAGGATGCATAATTCGATTTC |
| BID_fgt02Fcat | TCCTCGGGATATGATAAGATTAATAG |
| BID_fgt02RVcat | TCTCATATTATAAAAGCCAGTCATTAG |
| BID_covRSfgt03FRec | TAATGACTGGCTTTTATAATATGAGACTATTTATCTGCTCATTTC |
| BID_covRSfgt03RV | GAGCTTTTTTCAAATCTTC |
| BID_covRSKOFdiag | GAAGTGATGAATGAGATG |
| BID_covRSKORVdiag | CTTTCTCATCAATTGAGAC |

Primers used for the construction and validation of the clpC deletion mutant:

| BID_clpCUPF | CTTTGGGTTCTAATTTATC |
|---|---|
| BID_clpCUPRVRec | CTATTAATCTTATCATATCCCGAGGACGTTGGTGTATATTTTAC |
| BID_fgt02Fcat | TCCTCGGGATATGATAAGATTAATAG |
| BID_fgt02RVcat | TCTCATATTATAAAAGCCAGTCATTAG |
| BID_clpCDownFRec | CTAATGACTGGCTTTTATAATATGAGATAGAAATAAAGGAAAGGAC |
| BID_clpCDownRV | TTGCTTTAAGGATAGTTTC |
| BID_clpCFdiag | AGAAGCCAATAATGACGATG |
| BID_clpCRVdiag | AGAATTCTGATGATGCACAGTC |

Primers used for the construction of the inducible comX expression plasmid pGhPxylTcomX$_{IO}$:

| FT_pGhPxylcomXIOsacIIrv | AGCGCCGCGGTGGGATCCTCTAGAGTC |
|---|---|
| FT_pGhPxylcomX | CTGCAGGCATGCACATCATCAACTTGAAGGG |
| FT_PxylTIOsacIIfw | CCCACCGCGGTGGAGATACGAACAAATTAG |

TABLE 3-continued list of primers

| Primer name | Sequence (5'-3') |
|---|---|
| FT_PxylTIOrv | GATAGTAACTCCTTAATTTTTATTTGC |
| FT_comXIOrecfw | GCAAATAAAAATTAAGGAGTTACTATCATGACATATTACTTGGAAGAAGAGGATTTTG |
| FT_comXIOrecrv | CCTTCAAGTTGATGATGTGCATGCCTGCAGTCACTCTTCGTCTTC |

Primers used for the construction and validation of the SL12653-comX deletion mutant

| FT_comXlocusfw | TGACCATGTTACACAAGCCTATATCCT |
|---|---|
| FT_comXrecrv | CGCCCTTATGGGATTTATCTTCCTTACTTCGTTTCTTTGCATAACTTCGTCTTAAT |
| Uplox66 | TAAGGAAGATAAATCCCATAAGG |
| Dnlox71 | TTCACGTTACTAAAGGGAATGTA |
| FT_comXrecfw | TCTACATTCCCTTTAGTAACGTGAACCATGACCATTTTATAGGTTTAGATGTTTATG |
| AR_comxDNspecR | CGGTGTTCCTCCATATATCTACGC |
| FT_PxylcomXfw | CGCTAAACTCAACAGGTGATCCGATTG |

Construction of Plasmid pGhP32comX$_{MG}$

As a representative of the *cremoris* subspecies, the comX gene from the laboratory strain MG1363 was initially chosen. ComX proteins of this subspecies are highly conserved with at least 98% of identity. The comX gene was amplified by PCR using primers BID_ComXSDLLCup/BID_ComXSDLLCdown and inserted into plasmid pMG36eT under the control of the constitutive $P_{32}$ promoter by SacI/PstI cloning, yielding plasmid pMGP32comX$_{MG}$. The $P_{32}$-comX$_{MG}$ fusion from pMGP32comX$_{MG}$ was amplified by PCR with primers BID_pMGP32UpMfeI/BID_pMGTerDown, digested by MfeI/KpnI, and cloned in the EcoRI/KpnI-digested thermosensitive pG+host9 vector. The resulting plasmid was named pGhP32comX$_{MG}$.

Construction of Plasmid pGhP32comX$_{IO}$

As a representative of the *lactis* subspecies, the comX gene from the IO-1 strain was chosen. The comX gene was amplified by PCR using primers BID_ComXSDLLLup/BID_ComXSDLLLdown and inserted into plasmid pMG36eT under the control of the constitutive $P_{32}$ promoter by SacI/PstI cloning, yielding plasmid pMGP32comX$_{IO}$. The $P_{32}$-comX$_{IO}$ fusion from pMGP32comX$_{IO}$ was amplified by PCR with primers BID_pMGP32UpMfeI/BID_pMGTerDown, digested by MfeI/KpnI, and cloned in the EcoRI/KpnI-digested thermosensitive pG+host9 vector. The resulting plasmid was named pGhP32comX$_{IO}$.

Construction of Plasmid pGhost-Core

The Core part of the resolution site (IRS) recognized by the TnpI recombinase from Tn4430 was assembled by using the complementary primers DD-pGhost-CoreUp/DD-pGhost-CoreDW. The resulting DNA fragment was cloned between HindIII and EcoRI sites in plasmid pG+host9. The resulting plasmid, named pGhost-Core, was transformed in *E. coli* harbouring plasmid pGIV004 (TnpI+) for obtaining multimeric forms (Vanhooff V, Galloy C, Agaisse H, Lereclus D, Révet B, Hallet B. *Mol Microbiol*. 2006 May; 60(3):617-29).

Construction of $P_{comGA[MG]}$-luXAB Reporter Strain BLD101

The $P_{comGA[MG]}$ promoter was amplified by PCR from chromosomal DNA of *L. lactis* MG1363 (identical nucleotide sequence between MG1363 and KW2) with primers BID_LuxLLCf1/BID_LuxLLCr1 (PCR1 product). The luxABgenes were amplified by PCR from plasmid pJIM4900 with primers BID_LuxLLCf2/BID_LuxLLCr2 (PCR2 product). The $P_{comGA[MG]}$-luXAB fusion was created by overlapping PCR using PCR1 and PCR2 products and primers BID_LuxLLCf1/BID_LuxLLCr2. The resulting fusion was cloned in plasmid pSEUDOPusp45GFP using restriction enzymes XhoI and BamHI, yielding plasmid pSEUDOPusp45PcomGAluxAB. In order to remove the $P_{usp45}$ promoter, the entire vector except the $P_{usp45}$ promoter was amplified by inverse PCR with primers BID_P3pseudoLLC/BID_LuxLLCf1 and self-ligated after XhoI digestion, leading to plasmid pSEUDOPcomGAluxAB. The insertion cassette I/mg pseudo 10::$P_{comGA[MG]}$-luxAB was excised from plasmid pSEUDOPcomGAluxAB and cloned into the pG+host9 thermosensitive vector using restriction enzymes KpnI/EagI. The resulting plasmid pGhPcomGAluxAB was then electro-transformed in strain KW2 and used to integrate the $P_{comGA[MG]}$-luXAB cassette at locus kw2_0563 (llmg_pseudo_10 in MG1363) by double homologous recombination, resulting in the reporter strain KW2 kw2_0563::$P_{comGA[MG]}$-luxAB (strain BLD101).

Construction of Portable Luc Reporter Systems

The $P_{comGA[MG]}$ promoter was amplified by PCR from chromosomal DNA of *L. lactis* MG1363 with primers BID_LuxLLCf1/BID_LucLLCr1 (PCR1 product). The luc gene was amplified by PCR from plasmid pXL with primers BID_LucLLCf2/BID_LucLLCr2 (PCR2 product). The $P_{comGA[MG]}$-luc fusion was created by overlapping PCR using PCR1 and PCR2 products and primers BID_LuxLLCf1/BID_LucLLCr2. The resulting fusion was cloned in plasmid pSEUDOPusp45GFP using restriction enzymes XhoI and BamHI, yielding plasmid pSEUDOPusp45PcomGAluc. In order to remove the $P_{usp45}$ promoter, the entire vector except the $P_{udp45}$ promoter was amplified by inverse PCR with primers BID_P3pseudoLLC/BID_LuxLLCf1 and self-ligated after XhoI digestion, leading to plasmid pSEUDOPcomGAluc. The reporter cassette $P_{comGA[MG]}$-luc was amplified by PCR from pSEUDOPcomGAluc (primers BID_PcomGALLCF1*/BID_lucR1*) and cloned between XmaI and EagI into the pGhP32comX$_{MG}$ plasmid. The resulting reporter plasmid was named pGhP32comX$_{MG}$-P$_{comGA[MG]}$-luc.

The $P_{comGA[IO]}$ promoter was amplified from the IO-1 chromosome (primers BID_luxLLLf1/BID_lucLLLr1) and the luciferase gene (luc) was amplified from plasmid pXL (primers BID_lucLLLf2/BID_lucLLLr2). The cassette $P_{comGA}$[IO]-luc was created by overlapping PCR with primers BID_luxLLLf1/BID_lucLLLr2. The cassette $P_{comGA[IO]}$-luc was then amplified from the overlapping PCR product with primers BID_PcomGALLLF1*/BID_lucR1* for XmaI/EagI cloning into pGhP32comX$_{IO}$. The resulting reporter plasmid was named pGhP32comX$_{IO}$-P$_{comGA[IO]}$-luc.

Isolation of a rpsL Mutant Conferring Resistance to Streptomycin

Spontaneous streptomycin-resistant MG1363 clones were isolated on 1 mg ml$^{-1}$ streptomycin-containing plates. After the sequencing of the rpsL gene with primers RpsL Univ UP/RpsL Univ DN, one spontaneous mutant resulting in a mutation (K56I) into the ribosomal protein S12 that was previously shown to confer resistance to streptomycin was selected (FIG. 6). A 3.7-kb fragment containing the rpsL mutated gene (strA1 allele) was amplified by PCR with primers BID_LLcdacARpsL/BID_LLlcfusARpsL and cloned into the pGEM®-T easy vector (Promega), yielding plasmid pGEMrpsL*. This plasmid was used as template to generate the 3.7-kb PCR product with primers BID_LLcdacARpsL/BID_LLlcfusARpsL that was used as donor DNA in natural transformation assays of strain KW2.

Standard Natural Transformation Assay

The BLD101 reporter strain carrying the pGhP32comX$_{MG}$ plasmid (BLD101 [pGhP32comX$_{MG}$]) was grown overnight in M17G at 30° C. Then, 1.5 ml of the pre-culture was diluted in 8.5 ml of fresh M17G medium to restart the culture. After 2 hours of growth, cells were washed twice in distilled water and OD$_{600}$ was adjusted to 0.05 in CDM containing erythromycin (5 µg ml$^{-1}$) and supplemented with either 5% (v/v) glycerol or 5% (w/v) mannitol used as potential osmo-stabilizers. Typically, 5 µg of DNA was added in 300 µl of inoculated medium and the culture was further incubated during 6 hours at 30° C. Cells were then spread on M17G agar plates supplemented with appropriate antibiotics and CFUs were counted after 48 hours of incubation. The transformation frequency was calculated as the number of antibiotic-resistant CFU ml$^{-1}$ divided by the total number of viable CFU ml$^{-1}$. In the case of streptomycin-resistant transformants, antibiotic-resistant CFU ml$^{-1}$ corresponds to the number of transformants obtained in presence of DNA less the number of spontaneous transformants obtained in conditions where no DNA is added in the culture. The transfer of the mutation conferring streptomycin resistance was confirmed by DNA sequencing of the rpsL gene after its amplification by PCR using primers RpsL Univ UP/RpsL Univ DN.

Disruption of comEC by Natural Transformation

A comEC-containing DNA fragment of ~3.2 kb was amplified by PCR with primers BID_ComECLLCUp/BID_ComECLLCDown. Then, the PCR product was digested by SacI/NheI and cloned into the SacI/XbaI-digested suicide plasmid pUC18Ery (van Kranenburg et al., 1997), yielding plasmid pUCcomEC. To generate a comEC disruption cassette that allows the selection of double crossing-over recombinants, the $P_{32}$-cat fusion conferring resistance to chloramphenicol was cloned in the middle of the comEC gene. For this purpose, the $P_{32}$-catcassette was amplified by PCR from plasmid pNZ5319 (Lambert et al., 2007, Appl. Environ. Microbiol. 73:1126-1135) with primers BID_CatUpSpeI/BID_CatDownSpeI. The amplification product was digested by SpeI and cloned into the XbaI-digested pUCcomEC, yielding plasmid pUCcomECcat. This suicide plasmid was used to generate high quantity of donor DNA by PCR amplification for comEC disruption by natural transformation. The insertion of the $P_{32}$-cat cassette in the comEC gene of KW2 transformants was validated by PCR (primers in Table 3).

Deletion of mecA, ciaRH, covRS, and clpC Genes by Natural Transformation

The mecA, ciaRH, covRS, and clpC genes were similarly inactivated by the exchange of their ORFs by the $P_{32}$-cat cassette using double crossing-over events. For this purpose, overlapping PCR products containing the $P_{32}$-cat cassette flanked by two recombination arms of ~1.5 kb (upstream and downstream homologous regions) were generated as previously reported. Briefly, upstream, downstream, and $P_{32}$-cat fragments were separately amplified by PCR, purified, mixed in equimolar concentration, and assembled by overlapping PCR by using the most external primers (see list of primers in Table 3). 5 µg of the obtained overlapping PCR product was used as donor DNA for natural transformation of strain BLD101 [pGhP32comX$_{MG}$]. The correct insertion of the $P_{32}$-cat cassette in each targeted locus of the KW2 transformants was validated by PCR (see list of primers in Table 3). To obtain the final mutant strains, the thermosensitive vector pGhP32comX$_{MG}$ was cured by growing the strains overnight at 37° C. without erythromycin. The cultures were subsequently diluted and plated on M17G agar without erythromycin at 30° C. The resulting colonies were streaked in parallel on M17G plates with and without erythromycin. Absence of plasmid pGhP32comX$_{MG}$ in Ery$^S$ clones was validated by PCR.

Induction of Natural Competence in *Lactococcus raffinolactis*

Wild-type *Lactococcus raffinolactis* (i.e., *L. raffinolactis* strains which have not been previously engineered for the overproduction of the comX gene) were grown overnight in M17G at 30° C. 1.5 ml of the pre-culture was diluted in 8.5 ml of fresh M17G medium to restart the culture. After 2 hours of growth, cells were washed twice in distilled water and OD$_{600}$ was adjusted to 0.05 in CDM supplemented with either 5% (v/v) glycerol or 5% (w/v) mannitol used as potential osmo-stabilizers. 15 µg of plasmid pGhost-Core was added in 300 µl of inoculated medium and the culture was further incubated during 6 hours at 30° C. Cells were then spread on M17G agar plates supplemented with appropriate antibiotics and CFUs were counted after 48 hours of incubation. The transformation frequency was calculated as the number of antibiotic-resistant CFU ml$^{-1}$ divided by the total number of viable CFU ml$^{-1}$.

Natural Competence in *Lactococcus lactis* Subsp *Lactis* SL12651 and SL12653 Strains The *L. lactis* subsp. *lactis* SL12653 and 12651 strains were grown overnight at 30° C. Cells were washed twice in distilled water and OD$_{600}$ was adjusted to 0.05 in M17G. Typically, 5 µg of donor DNA was added in 200 µl of inoculated medium (25 µg/ml) and the culture was further incubated during 24 hours at 30° C. Cells were then spread on M17G agar plates supplemented with appropriate antibiotics and CFUs were counted after 48 hours of incubation at 30° C. The transformation frequency calculated exactly as described above (see Standard natural transformation assay).

The same experiments were done in SL12653 with various concentrations of donor DNA (0.5, 2.5, 5 and 25 µg/ml)

Construction of Plasmid pGhPxyvTcomXIO

As a representative of the *lactis* subspecies, the comX gene and the promoter of the xy/T gene from the IO-1 strain were chosen. The comX gene was amplified by PCR using primers FT_comXIOrecfw and FT_comXIOrecrv (PCR1), both containing overlapping sequences. The xy/T promoter region was amplified by PCR using primers FT_PxylTIOsacIIfw and FT_PxylTIOrv (PCR2). The carrying vector was amplified from plasmid pGhP32comX$_{MG}$ and amplified by PCR using primers FT pGhPxylcomXIOsacIIrv and FT pGhPxylcomX (PCR3). The three PCR products were purified, mixed in an equimolar concentration and assembled by overlapping PCR using the most external primers, containing a SacII restriction site. The amplification product was digested by SacII and self-ligated. The resulting plasmid was named pGhPxylTcomX$_{IO}$.

Transformation Assay in SL12653 Mutants Deleted for the comX Gene

The comX gene of SL12653 was inactivated by exchange of their ORF by the P$_{32}$-cat cassette using double crossing-over events. For this purpose, overlapping PCR products containing the P$_{32}$-cat cassette flanked by two recombination arms of ~1.5 kb (upstream and downstream homologous regions) were generated as previously reported. Briefly, upstream, downstream, and the P$_{32}$-cat fragments were separately amplified by PCR, purified and mixed in equimolar concentration, and assembled by overlapping PCR by using the most external primers (see primers in Table 3). 5 µg of the obtained PCR product was used as donor DNA for natural transformation of strain SL12653 [pGhPxylTcomX$_{IO}$] (ComX$^+$). The correct insertion of the P$_{32}$-cat cassette in the targeted locus of SL12653 transformants was validated by PCR (see primers in Table 3). To obtain the final mutant strains, the thermosensitive vector pGhPxylTcomX$_{IO}$ was cured by growing the strains overnight at 37° C. without erythromycin. The cultures were subsequently diluted and plated on M17G agar without erythromycin at 30° C. The resulting colonies were streaked in parallel on M17G plates with and without erythromycin. Absence of plasmid pGhPxylTcomX$_{IO}$ in Ery$^S$ clones was validated by PCR. Thus, 3 ΔcomX clones of SL12653 were obtained.

Xylose-Induced Natural Transformation in SL12653.

The *L. lactis* subsp. *lactis* SL12653 [pGhPxylTcomX$_{IO}$] was grown overnight at 30° C. Cells were washed twice in distilled water and OD600 was adjusted to 0.05 in M17 supplemented with 1% (w/v) xylose. Typically, 5 µg of DNA was added in 200 µl of inoculated medium and the culture was further incubated during 24 hours at 30° C. Cells were then spread on M17G agar plates supplemented with appropriate antibiotics and CFUs were counted after 48 hours of incubation at 30° C. The transformation frequency was calculated exactly as described above (see Standard natural transformation assay).

All publications mentioned in the above specification are herein incorporated by reference. Various modifications and variations of the described present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in molecular biology, biochemistry, microbiology, bacteriology, or related fields are intended to be within the scope of the following claims.

REFERENCES

Bachmann, H., W. L. de, M. Kleerebezem, and J. E. van Hylckama Vlieg. 2010. Time-resolved genetic responses of *Lactococcus lactis* to a dairy environment. *Environ. Microbiol.* 12:1260-1270.

Campbell, E. A., S. Y. Choi, and H. R. Masure. 1998. A competence regulon in *Streptococcus pneumoniae* revealed by genomic analysis. *Mol. Microbiol.* 27:929-939 David, B., Radziejwoski, A., Toussaint, F., Fontaine, L., Henry de Frahan, M., Patout, C., van Dillen, S., Boyaval, P., Horvath, P., Fremaux, C. and P. Hols. 2017. Natural DNA transformation is functional in *Lactococcus lactis* subsp. *cremoris* KW2. *Appl. Environ. Microbiol.* 83(16): 1-17 Ercan, O., M. Wels, E. J. Smid, and M. Kleerebezem. 2015. Genome-wide transcriptional responses to carbon starvation in nongrowing *Lactococcus lactis*. *Appl. Environ. Microbiol.* 81:2554-2561.

Fontaine, L., C. Boutry, M. H. de Frahan, B. Delplace, C. Fremaux, P. Horvath, P. Boyaval, and P. Hols. 2010. A novel pheromone quorum-sensing system controls the development of natural competence in *Streptococcus thermophilus* and *Streptococcus salivarius*. *J. Bacteriol.* 192:1444-1454.

Lee, M. S. and D. A. Morrison. 1999. Identification of a new regulator in *Streptococcus pneumoniae* linking quorum sensing to competence for genetic transformation. *J. Bacteriol.* 181:5004-5016.

Luo, P. and D. A. Morrison. 2003. Transient association of an alternative sigma factor, ComX, with RNA polymerase during the period of competence for genetic transformation in *Streptococcus pneumoniae*. *J. Bacteriol.* 185:349-358

Martin-Galiano and de la Campa 2003. High-Efficiency Generation of Antibiotic-Resistant Strains of *Streptococcus pneumoniae* by PCR and Transformation. Antimicrob Agents Chemother. 47(4):1257-1261

Peterson, S. N., C. K. Sung, R. Cline, B. V. Desai, E. C. Snesrud, P. Luo, J. Walling, H. Li, M. Mintz, G. Tsegaye, P. C. Burr, Y. Do, S. Ahn, J. Gilbert, R. D. Fleischmann, and D. A. Morrison. 2004. Identification of competence pheromone responsive genes in *Streptococcus pneumoniae* by use of DNA microarrays. *Mol. Microbiol.* 51:1051-1070

Terzaghi and Sandine 1975. Improved Medium for Lactic Streptococci and Their Bacteriophages. *Applied Microbiology* 29(6): 807-813

Todd, E. W., and L. F. Hewitt. 1932. A new culture medium for the production of antigenic streptococcal haemolysin. *J. Pathol.* Bacteriol. 35:973-975

Updyke, E. L., and M. I. Nickle. 1954. A dehydrated medium for the preparation of type specific extracts of group A streptococci. *Appl. Microbiol.* 2:117-118

Sambrook, J., E. F. Fritsch, and T. Maniatis. 1989. Molecular cloning: a laboratory manual.

Sissler, M., Delorme, C., Bond, J., Dusko Ehrlich, S., Renault, P. and C. Francklyn. 1999. An aminoacyl-tRNA synthetase paralog with a catalytic role in histidine biosynthesis. *Proc. Natl. Acad. Sci.* 96:8985-8990 van Kranenburg, R., J. D. Marugg, I. I. van Swam, N. J. Willem, and W. M. de Vos. 1997. Molecular characterization of the plasmid-encoded eps gene cluster essential for exopolysaccharide biosynthesis in *Lactococcus lactis*. *Mol. Microbiol.* 24:387-397.

Ward, L. J., J. C. Brown, and G. P. Davey. 1998. Two methods for the genetic differentiation of *Lactococcus lactis* ssp. *lactis* and *cremoris* based on differences in the 16S rRNA gene sequence. *FEMS Microbiol Lett.* 166:15-20

Wegmann, U., M. O'Connell-Motherway, A. Zomer, G. Buist, C. Shearman, C. Canchaya, M. Ventura, A. Goesmann, M. J. Gasson, O. P. Kuipers, S. D. van, and J. Kok. 2007. Complete genome sequence of the prototype lactic acid bacterium *Lactococcus lactis* subsp. *cremoris* MG1363. *J. Bacteriol.* 189:3256-3270.

Wydau, S., R. Dervyn, J. Anba, E. S. Dusko, and E. Maguin. 2006. Conservation of key elements of natural competence in *Lactococcus lactis* ssp. *FEMS Microbiol. Lett.* 257:32-42.

---

The invention claimed is:

1. A method for transforming a strain of the *Lactococcus lactis* species with an exogenous DNA polynucleotide comprising the steps of:
   (a) providing a strain of the *Lactococcus lactis* species, wherein said strain is transformable through natural competence;
   (b) modulating the production of a ComX protein in said strain, by expressing a comX gene in said strain or increasing the expression of a comX gene in said strain;
   (c) contacting said strain of step (b) with an exogenous DNA polynucleotide in a medium and incubating the resulting mixture for integration of the exogenous DNA polynucleotide into the genome of said strain; and
   (d) selecting a strain which has integrated the exogenous DNA polynucleotide into its genome.

2. A method according to claim 1, wherein said comX gene is an exogenous comX gene.

3. A method according to claim 2, wherein said exogenous comX gene is transferred into said strain by conjugation, transduction, or transformation.

4. A method according to claim 1, wherein said comX gene is the endogenous comX gene of said strain.

5. A method according to claim 4, wherein the method comprises carrying out step (b) and then carrying out step (c) or comprises carrying out step (b) and step (c) simultaneously.

6. A method according to claim 1, wherein said ComX protein has the amino acid sequence of SEQ ID NO: 2, SEQ ID NO:4, SEQ ID NO:6, SEQ ID NO: 8, SEQ ID NO:10, SEQ ID NO: 12, SEQ ID NO: 14, SEQ ID NO: 16, SEQ ID NO: 18, SEQ ID NO:20 or SEQ ID NO:22 or an amino acid sequence having at least 90%, at least 95%, at least 97%, or at least 99% identity to the amino acid sequence of SEQ ID NO: 2, SEQ ID NO:4, SEQ ID NO:6, SEQ ID NO:8, SEQ ID NO: 10, SEQ ID NO: 12, SEQ ID NO: 14, SEQ ID NO: 16, SEQ ID NO: 18, SEQ ID NO:20 or SEQ ID NO: 22 or an amino acid sequence having at least 90%, at least 95%, at least 97%, or at NO:22.

7. A method according to claim 1, wherein said comX gene has the nucleotide sequence of SEQ ID NO:1, SEQ ID NO:3, SEQ ID NO:5, SEQ ID NO:7, SEQ ID NO:9, SEQ ID NO: 11, SEQ ID NO: 13, SEQ ID NO: 15, SEQ ID NO: 17, SEQ ID NO: 19, SEQ ID NO:21 or a nucleotide sequence having at least 90%, at least 95%, at least 97% or at least 99% identity to the nucleotide sequence of SEQ ID NO: 1, SEQ ID NO: 3, SEQ ID NO:5, SEQ ID NO:7, SEQ ID NO:9, SEQ ID NO: 11, SEQ ID NO: 13, SEQ ID NO:15, SEQ ID NO:17, SEQ ID NO:19, SEQ ID NO:21.

8. A method according to claim 1, wherein said medium of step (c) is a chemically defined medium.

9. A method according to claim 1, wherein prior to step (c) said strain is incubated in a pre-culture medium.

10. A method according to claim 1, wherein said strain is incubated with the exogenous DNA polynucleotide for around 4-8 hours at around 30° C. and said medium of step (c) is supplemented with an osmo-stabilizer.

11. A method according to claim 1, wherein said exogenous DNA polynucleotide used in step (c) is from a strain of the same species.

12. The method according to claim 10, wherein the osmo-stabilizer is glycerol or mannitol.

* * * * *